United States Patent
Andrews et al.

(10) Patent No.: US 9,163,021 B2
(45) Date of Patent: Oct. 20, 2015

(54) PYRROLO[3,2-C]PYRIDINE TROPOMYOSIN-RELATED KINASE INHIBITORS

(71) Applicant: Pfizer Limited, Sandwich, Kent (GB)

(72) Inventors: Mark David Andrews, Sandwich (GB); Sharanjeet Kaur Bagal, Great Abington (GB); David Graham Brown, Sandwich (GB); Karl Richard Gibson, Sandwich (GB); Wolfgang Klute, Sandwich (GB); Inaki Morao, Sandwich (GB); Kiyoyuki Omoto, Great Abington (GB); Thomas Ryckmans, Sandwich (GB); Yogesh Sabnis, Sandwich (GB); Sarah Elizabeth Skerratt, Great Abington (GB); Paul Anthony Stupple, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 14/430,286

(22) PCT Filed: Sep. 26, 2013

(86) PCT No.: PCT/IB2013/058895
§ 371 (c)(1),
(2) Date: Mar. 23, 2015

(87) PCT Pub. No.: WO2014/053968
PCT Pub. Date: Apr. 10, 2014

(65) Prior Publication Data
US 2015/0246912 A1   Sep. 3, 2015

Related U.S. Application Data

(60) Provisional application No. 61/709,497, filed on Oct. 4, 2012.

(51) Int. Cl.
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC .................... C07D 471/04 (2013.01)

(58) Field of Classification Search
CPC .. C07D 401/02; C07D 401/10; A61K 31/437; A61K 31/4353
USPC .......................................... 546/113; 514/300
See application file for complete search history.

(56) References Cited

U.S. PATENT DOCUMENTS

| 6,613,932 B1 | 9/2003 | Sato et al. |
| 7,241,890 B2 | 7/2007 | Kasibhatla et al. |
| 7,417,063 B2 | 8/2008 | Smallheer et al. |
| 7,595,325 B2 | 9/2009 | Marx et al. |
| 2002/0002183 A1 | 1/2002 | Zhu et al. |
| 2003/0119793 A1 | 6/2003 | Ledford et al. |
| 2006/0035912 A1 | 2/2006 | Marx et al. |
| 2007/0032519 A1 | 2/2007 | Zhang et al. |
| 2009/0076046 A1 | 3/2009 | Zhang et al. |
| 2009/0286782 A1 | 11/2009 | Ibrahim et al. |
| 2009/0286783 A1 | 11/2009 | Ibrahim et al. |
| 2009/0318441 A1 | 12/2009 | Brian et al. |
| 2011/0230482 A1 | 9/2011 | Zhang et al. |
| 2011/0319403 A1 | 12/2011 | Zhou et al. |

FOREIGN PATENT DOCUMENTS

| JP | 2003321472 | 11/2003 |
| WO | 0119798 | 3/2001 |
| WO | 0164642 | 9/2001 |
| WO | 0164643 | 9/2001 |
| WO | 02098876 | 12/2002 |
| WO | 03037860 | 5/2003 |
| WO | 2004056830 | 7/2004 |
| WO | 2005028434 | 3/2005 |
| WO | 2005099709 | 10/2005 |
| WO | 2006050053 | 5/2006 |
| WO | 2006060535 | 6/2006 |
| WO | 2006074041 | 7/2006 |
| WO | 2007002325 | 1/2007 |
| WO | 2007002433 | 1/2007 |
| WO | 2007013896 | 2/2007 |

(Continued)

OTHER PUBLICATIONS

Zhang et al., Journal of Organic Chemistry (2002), 67(17), 6226-6227.*

(Continued)

*Primary Examiner* — Niloofar Rahmani
(74) *Attorney, Agent, or Firm* — Richard V. Zanzalari

(57) ABSTRACT

The present invention relates to compounds of Formula (I)

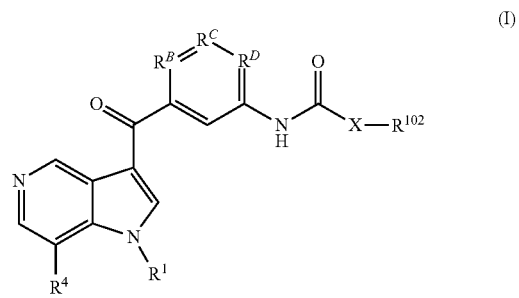

and their pharmaceutically acceptable salts, wherein the substituents are as described herein, and their use in medicine, in particular as Trk antagonists.

10 Claims, No Drawings

(56) References Cited

FOREIGN PATENT DOCUMENTS

| | | |
|---|---|---|
| WO | 2007047207 | 4/2007 |
| WO | 2007061882 | 5/2007 |
| WO | 2007075572 | 7/2007 |
| WO | 2007126841 | 11/2007 |
| WO | 2007134169 | 11/2007 |
| WO | 2007140222 | 12/2007 |
| WO | 2008063888 | 5/2008 |
| WO | 2008064255 | 5/2008 |
| WO | 2008064265 | 5/2008 |
| WO | 2009012283 | 1/2009 |
| WO | 2009121033 | 10/2009 |
| WO | 2009143018 | 11/2009 |
| WO | 2009143024 | 11/2009 |
| WO | 2010045542 | 4/2010 |
| WO | 2010107765 | 9/2010 |
| WO | 2010107768 | 9/2010 |
| WO | 2010111527 | 9/2010 |
| WO | 2011093672 | 8/2011 |
| WO | 2012048058 | 4/2012 |

OTHER PUBLICATIONS

International Patent application No. PCT/IB2013/058895 Search Report and Written Opinion mailed Feb. 10, 2014, 7 pages.
Wang, Tao, et al., "Trk kinase inhibitors as new treatments for cancer and pain", Expert Opinion Therapeutic Patents, 2009, pp. 305-319, 19(3).

* cited by examiner

PYRROLO[3,2-C]PYRIDINE TROPOMYOSIN-RELATED KINASE INHIBITORS

This application is a national stage application under 35 U.S.C. 371 of PCT/IB2013/058895, filed on Sep. 26, 2013, which claims the benefit of U.S. Provisional Patent Application No. 61/709,497, filed on Oct. 4, 2012, the disclosures of which are hereby incorporated by reference in their entirety.

The invention described herein relates to certain pyrrolo[3,2-c]pyridine compounds and the pharmaceutically acceptable salts of such compounds. The invention also relates to the processes for the preparation of the compounds, compositions containing the compounds, and the uses of such compounds and salts in treating diseases or conditions associated with tropomyosin-related kinase (Trk), activity. More specifically the invention relates to the compounds and their salts useful as inhibitors of Trk.

BACKGROUND

Tropomyosin-related kinases (Trks) are a family of receptor tyrosine kinases activated by neurotrophins. Trks play important roles in pain sensation as well as tumour cell growth and survival signaling. Thus, inhibitors of Trk receptor kinases might provide targeted treatments for conditions such as pain and cancer. Recent developments in this field have been reviewed by Wang et al in Expert Opin. Ther. Patents (2009) 19(3): 305-319 and an extract is reproduced below.

"1.1 Trk Receptors

As one of the largest family of proteins encoded by the human genome, protein kinases are the central regulators of signal transduction as well as control of various complex cell processes. Receptor tyrosine kinases (RTKs) are a subfamily of protein kinases (up to 100 members) bound to the cell membrane that specifically act on the tyrosine residues of proteins. One small group within this subfamily is the Trk kinases, with three highly homologous isoforms: TrkA, TrkB, and TrkC. All three isoforms are activated by high affinity growth factors named neurotrophins (NT): i) nerve growth factor (NGF), which activates TrkA; ii) brain-derived neurotrophic factor (BDNF) and NT-4/5, which activate TrkB; and iii) NT-3, which activates TrkC. The binding of neurotrophins to the extracellular domain of Trks causes the Trk kinase to autophosphorylate at several intracellular tyrosine sites and triggers downstream signal transduction pathways. Trks and neurotrophins are well known for their effects on neuronal growth and survival.

1.2 Trks and Cancer

Originally isolated from neuronal tissues, Trks were thought to mainly affect the maintenance and survival of neuronal cells. However, in the past 20 years, increasing evidence has suggested that Trks play key roles in malignant transformation, chemotaxis, metastasis, and survival signaling in human tumors. The association between Trks and cancer focused on prostate cancer in earlier years and the topic has been reviewed. For example, it was reported that malignant prostate epithelial cells secrete a series of neurotrophins and at least one Trks. In pancreatic cancer, it was proposed that paracrine and/or autocrine neurotrophin-Trk interactions may influence the invasive behavior of the cancer. TrkB was also reported to be overexpressed in metastatic human pancreatic cancer cells. Recently, there have been a number of new findings in other cancer settings. For example, a translocation leads to expression of a fusion protein derived from the N-terminus of the ETV6 transcription factor and the C-terminal kinase domain of TrkC. The resulting ETV6-TrkC fusions are oncogenic in vitro and appear causative in secretory breast carcinoma and some acute myelogenous leukemias (AML). Constitutively active TrkA fusions occurred in a subset of papillary thyroid cancers and colon carcinomas. In neuroblastoma, TrkB expression was reported to be a strong predictor of aggressive tumor growth and poor prognosis, and TrkB overexpression was also associated with increased resistance to chemotherapy in neuroblastoma tumor cells in vitro. One report showed that a novel splice variant of TrkA called TrkAIII signaled in the absence of neurotrophins through the inositol phosphate-AKT pathway in a subset of neuroblastoma. Also, mutational analysis of the tyrosine kinome revealed that Trk mutations occurred in colorectal and lung cancers. In summary, Trks have been linked to a variety of human cancers, and discovering a Trk inhibitor and testing it clinically might provide further insight to the biological and medical hypothesis of treating cancer with targeted therapies.

1.3 Trks and Pain

Besides the newly developed association with cancer, Trks are also being recognized as an important mediator of pain sensation. Congenital insensitivity to pain with anhidrosis (CIPA) is a disorder of the peripheral nerves (and normally innervated sweat glands) that prevents the patient from either being able to adequately perceive painful stimuli or to sweat. TrkA defects have been shown to cause CIPA in various ethnic groups.

Currently, non-steroidal anti-inflammatory drugs (NSAIDs) and opiates have low efficacy and/or side effects (e.g., gastrointestinal/renal and psychotropic side effects, respectively) against neuropathic pain and therefore development of novel pain treatments is highly desired. It has been recognized that NGF levels are elevated in response to chronic pain, injury and inflammation and the administration of exogenous NGF increases pain hypersensitivity. In addition, inhibition of NGF function with either anti-NGF antibodies or non-selective small molecule Trk inhibitors has been shown to have effects on pain in animal models. It appears that a selective Trk inhibitor (inhibiting at least NGF's target, the TrkA receptor) might provide clinical benefit for the treatment of pain. Excellent earlier reviews have covered targeting NGF/BDNF for the treatment of pain so this review will only focus on small molecule Trk kinase inhibitors claimed against cancer and pain. However, it is notable that the NGF antibody tanezumab was very recently reported to show good efficacy in a Phase II trial against osteoarthritic knee pain."

International Patent Application publication number WO2009/012283 refers to various fluorophenyl compounds as Trk inhibitors; International Patent Application publication numbers WO2009/152087, WO2008/080015 and WO2008/08001 and WO2009/152083 refer to various fused pyrroles as kinase modulators; International Patent Application publication numbers WO2009/143024 and WO2009/143018 refer to various pyrrolo[2,3-d]pyrimidines substituted as Trk inhibitors; International Patent Application publication numbers WO2004/056830 and WO2005/116035 describe various 4-amino-pyrrolo[2,3-d]pyrimidines as Trk inhibitors. International Patent Application publication number WO2011/133637 describes various pyrrolo[2,3-d]pyrimidines and pyrrolo[2,3-b]pyridines as inhibitors of various kinases. International Patent Application publication number WO2005/099709 describes bicyclic heterocycles as serine protease inhibitors. International Patent Application publication number WO2007/047207 describes bicyclic heterocycles as FLAP modulators.

US provisional application U.S. 61/471,758 was filed 5 Apr. 2011. Convention applications U.S. Ser. No. 13/439,131 (filed 4 Apr. 2012) and PCT/IB2012/051363 (filed 22 Mar. 2012) claiming priority thereto. The whole contents of those application in their entirety are herewith included by reference thereto.

Thus Trk inhibitors have a wide variety of potential medical uses. There is a need to provide new Trk inhibitors that are good drug candidates. In particular, compounds should preferably bind potently to the Trk receptors in a selective manner compared to other receptors, whilst showing little affinity for other receptors, including other kinase and/or GPC receptors, and show functional activity as Trk receptor antagonists. They should be non-toxic and demonstrate few side-effects. Furthermore, the ideal drug candidate will exist in a physical form that is stable, non-hygroscopic and easily formulated. They should preferably be e.g. well absorbed from the gastrointestinal tract, and/or be injectable directly into the bloodstream, muscle, or subcutaneously, and/or be metabolically stable and possess favourable pharmacokinetic properties.

Among the aims of this invention are to provide orally-active, efficacious, compounds and salts which can be used as active drug substances, particularly Trk antagonists, i.e. that block the intracellular kinase activity of the Trk, e.g. TrkA (NGF) receptor. Other desirable features include good HLM/hepatocyte stability, oral bioavailability, metabolic stability, absorption, selectivity over other types of kinase, dofetilide selectivity. Preferable compounds and salts will show a lack of CYP inhibition/induction, and be CNS-sparing.

SUMMARY

The present invention provides compounds of Formula I:

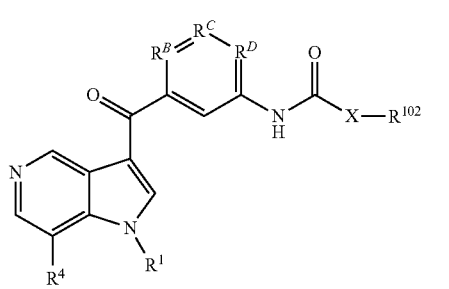

(I)

Wherein
$R^4$ is H or F;
One of $R^B$, $R^C$ and $R^D$ is N and the others are CH, CCN or C($C_{1-4}$ alkoxy);
X is a bond or $CH_2$;
$R^1$ is selected from $C_{2-4}$ alkyl optionally substituted by OH, and oxetanyl; and
$R^{102}$ is 5- or 6-membered unsaturated ring optionally substituted by 1 or 2 substituents independently selected from halo, =O, CN, $C_{1-4}$ alkyl optionally substituted by one or more F or OH or $C_{1-3}$ alkoxy optionally substituted by one or more F, and $C_{3-6}$ cycloalkyl,
and pharmaceutically acceptable salts thereof.

The invention also comprises pharmaceutical compositions comprising a therapeutically effective amount of a compound of formula I as defined herein, or a pharmaceutically acceptable salt thereof, and a pharmaceutically acceptable carrier.

The invention is also directed to a method of treating a disease or condition indicated for treatment with a Trk antagonist, in a subject, by administering to a subject in need thereof a therapeutically effective amount of one or more of the compounds herein, or a pharmaceutically acceptable salt thereof.

Other aspects of the invention will be apparent from the remaining description and claims.

Preferably, the compounds of the present invention are potent antagonists at Trk receptors, and have a suitable PK profile to enable once daily dosing.

The compounds of the present invention are potentially useful in the treatment of a range of disorders where a Trk antagonist is indicated, particularly pain indications. Depending on the disease and condition of the patient, the term "treatment" as used herein may include one or more of curative, palliative and prophylactic treatment.

According to the invention a compound of the present invention may be useful to treat any physiological pain such as inflammatory pain, nociceptive pain, neuropathic pain, acute pain, chronic pain, musculo-skeletal pain, on-going pain, central pain, heart and vascular pain, head pain, orofacial pain. Other pain conditions which may be treated include intense acute pain and chronic pain conditions which may involve the same pain pathways driven by pathophysiological processes and as such cease to provide a protective mechanism and instead contribute to debilitating symptoms associated with a wide range of disease states.

Pain is a feature of many trauma and disease states. When a substantial injury, via disease or trauma, to body tissue occurs the characteristics of nociceptor activation are altered, this leads to hypersensitivity at the site of damage and in nearby normal tissue. In acute pain the sensitivity returns to normal once the injury has healed. However, in many chronic pain states, the hypersensitivity far outlasts the healing process and is normally due to nervous system injury due to maladaptation of the afferent fibres (Woolf & Salter 2000 Science 288: 1765-1768). Clinical pain is present when discomfort and abnormal sensitivity feature among the patient's symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Pain can be divided into a number of different areas because of differing pathophysiology, these include nociceptive, inflammatory, neuropathic pain among others. It should be noted that some types of pain have multiple aetiologies and thus can be classified in more than one area, e.g. Back pain, Cancer pain have both nociceptive and neuropathic components.

Nociceptive Pain

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmit rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertabral discs or abnormalities of the lumbar facet joints, sacroiliac joints, paraspinal muscles or the posterior longitudinal ligament.

Neuropathic Pain

According to the invention a compound of the present invention can potentially be used to treat neuropathic pain and the symptoms of neuropathic pain including hyperalgesia, allodynia and ongoing pain. Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

Intense Acute Pain and Chronic Pain

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) exaggerated pain responses to noxious stimuli (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies.

Chronic Pain

Chronic pain comprises one or more of, chronic nociceptive pain, chronic neuropathic pain, chronic inflammatory pain, breakthrough pain, persistent pain hyperalgesia, allodynia, central sensitisation, peripheral sensitisation, disinhibition and augmented facilitation.

Chronic pain includes cancer pain, e.g. cancer pain arising from malignancy, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumour s, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Cancer pain also comprises visceral pain, e.g. visceral pain which arises from pancreatic cancer and/or metastases in the abdomen, somatic pain, e.g. somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

Inflammatory Pain

Inflammatory conditions include acute inflammation, persistent acute inflammation, chronic inflammation, and combined acute and chronic inflammation.

Inflammatory pain includes acute inflammatory pain and/or chronic inflammatory pain wherein the chronic inflammatory pain can be pain involving both peripheral and central sensitisation and/or mixed etiology pain involving both inflammatory pain and neuropathic pain or nociceptive pain components. Inflammatory pain also comprises hyperalgesia, e.g. primary and/or secondary hyperalgesia. Additionally or alternatively the inflammatory pain can include allodynia. Inflammatory pain also comprises pain that persists beyond resolution of an underlying disorder or inflammatory condition or healing of an injury.

Inflammatory pain is pain resulting an inflammatory condition. e.g. in response to acute tissue injury due to trauma, disease e.g. an inflammatory disease, immune reaction, the presence of foreign substances, chemicals or infective particles for example micro-organisms. Inflammatory conditions can be either acute or chronic inflammation or both.

Inflammatory pain can result from an inflammatory condition due to an inflammatory disease such as inflammatory joint diseases, inflammatory connective tissue diseases, inflammatory autoimmune diseases, inflammatory myopathies, inflammatory digestive system diseases, inflammatory air way diseases, cellular immune inflammation diseases, hypersensitivities and allergies, vasular inflammation diseases, non-immune inflammatory disease, synovitis, villonodular synovitis, arthralgias, ankylosing spondylitis, spondyloarthritis, spondyloarthropathy, gout, Pagets disease, periarticular disorders such as bursitis, rheumatoid disease, rheumatoid arthritis and osteoarthritis, rheumatoid arthritis or osteoarthritis. Rheumatoid arthritis in particular, represents ongoing inflammation associated with severe pain. Arthritic pain is a form of inflammatory pain and arises from inflammation in a joint which causes both peripheral sensitization and central sensitization. Under inflammatory conditions the nociceptive system is activated by normally innocuous and nonpainful mechanical stimuli. Additionally when the joint is at rest pain is present and appears as spontaneous pain and hyperalgesia (augmented pain response on noxious stimulation and pain on normally nonpainful stimulation). Inflammatory processes in peripheral tissues lead to central sensitization in the spinal cord, which contributes to hyperalgesia and allodynia typically associated with inflammatory pain. Other types of inflammatory pain include inflammatory bowel diseases (IBD).

Other Types of Pain

Other types of pain include but are not limited to:

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis;

Central pain or 'thalamic pain' as defined by pain caused by lesion or dysfunction of the nervous system including but not limited to central post-stroke pain, multiple sclerosis, spinal cord injury, Parkinson's disease and epilepsy;

Heart and vascular pain including but not limited to angina, myocardical infarction, mitral stenosis, pericarditis, Raynaud's phenomenon, scleredoma, scleredoma, skeletal muscle ischemia;

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis;

Head pain including but not limited to migraine, migraine with aura, migraine without aura cluster headache, tension-type headache. Orofacial pain including but not limited to dental pain, temporomandibular myofascial pain, tinnitus, hot flushes, restless leg syndrome and blocking development of abuse potential. Further pain conditions may include, back pain (e.g. chronic lower back pain), cancer pain, complex regional syndrome, HIV-related neuropathic pain, post-operative induced neuropathic pain, post-stroke pain, spinal cord injury pain, traumatic nerve injury pain, diabetic peripheral neuropathy, moderate/severe interstitial cystitis pain, irritable bowel syndrome pain, moderate/severe endometriosis pain, moderate/severe pelvic pain, moderate/severe prostatitis pain, moderate/severe osteoarthritis pain, post-herpetic neuralgia, rheumatoid arthritis pain, dysmenorrhea pain, pre-emptive post-operative pain, trigeminal neuralgia, bursitis, dental pain, fibromyalgia or myofacial pain, menstrual pain, migraine, neuropathic pain (including painful diabetic neuropathy), pain associated with post-herpetic neuralgia, post-operative pain, referred pain, trigeminal neuralgia, visceral pain (including interstitial cystitis and IBS) and pain associated with AIDS, allodynia, burns, cancer, hyperalgesia, hypersensitisation, spinal trauma and/or degeneration and stroke.

DETAILED DESCRIPTION

Embodiment 1 of the invention is a compound of Formula I:

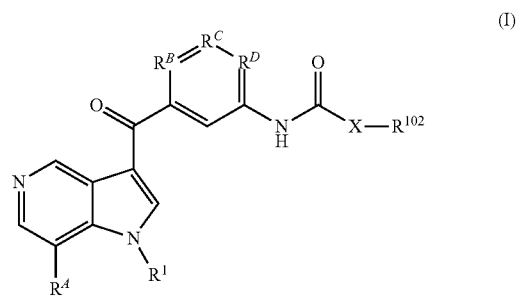

or a pharmaceutically acceptable salt thereof, wherein $R^A$ is H or F;

One of $R^B$, $R^C$ and $R^D$ is N and the others are CH, CCN or $C(C_{1-4}$ alkoxy);

X is a bond or $CH_2$;

$R^1$ is selected from $C_{2-4}$ alkyl optionally substituted by OH, or oxetanyl; and $R^{102}$ is 5- or 6-membered unsaturated ring optionally substituted by 1 or 2 substituents independently selected from halo, =O, CN, $C_{1-4}$ alkyl optionally substituted by one or more F, OH or $C_{1-3}$ alkoxy optionally substituted by one or more F, and $C_{1-4}$ cycloalkyl.

Embodiment 2: A compound or salt according to embodiment 1 wherein $R^1$ is selected

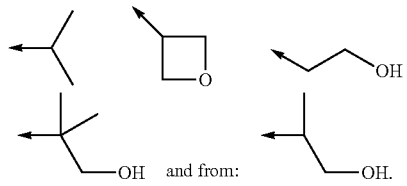

Embodiment 3: A compound or salt according to embodiment 1 or 2 wherein $R^{102}$ is a ring system which ring is selected from:

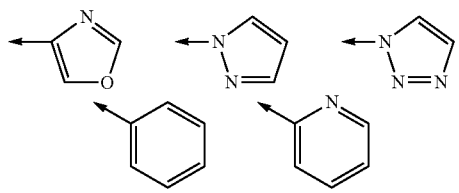

and which ring is optionally substituted by 1 or 2 substituents independently selected from F, Cl, =O, CN, $CF_3$, $OCF_3$, $CH_3$, isopropyl, $OCH_3$, cyclopropyl, and

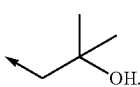

Embodiment 4: A compound or salt according to embodiment 1, 2 or 3 wherein $R^B$ and $R^D$ are CH and $R^C$ is N.

Embodiment 5: A compound or salt according to embodiment 1, 2, 3 or 4 wherein X is $CH_2$.

Embodiment 6: A compound or salt according to embodiment 1, 2, 3, 4 or 5 wherein $R^1$ is 1-hydroxy-2-methylpropan-2-yl.

Embodiment 7: A compound or salt of Formula:

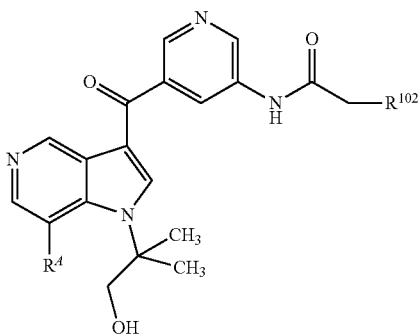

or a pharmaceutically acceptable salt thereof, wherein $R^4$ is H or F;
and $R^{102}$ is selected from phenyl, pyridyl and pyrazolyl, each of which is substituted by 1 or 2 substituents independently selected from cyclopropyl, methyl, $CF_3$ and Cl.

Embodiment 8: A compound or salt according to embodiment 1, 2, 3, 4, 5, 6 or 7 wherein $R^{102}$ is selected from phenyl, pyridin-2-yl and pyrazol-1-yl, each of which is substituted by 1 or 2 substituents independently selected from cyclopropyl, methyl, $CF_3$ and Cl.

Embodiment 9: A compound or salt according to embodiment 1, 2, 3, 4, 5, 6, 7 or 8 wherein $R^{102}$ is selected from 4-chlorophenyl, 3-$CF_3$-phenyl, 4-$CF_3$-phenyl, 5-chloropyridin-2-yl, 4-$CF_3$-pyrazol-1-yl, 3-cyclopropylpyrazol-1-yl and 5-methyl-3-$CF_3$-pyrazol-1-yl.

Embodiment 10: A compound or salt according to embodiment 1 selected from:
N-{5-[7-Fluoro-1-(2-hydroxy-1,1-dimethyl-ethyl)-1H-pyrrolo[3,2-c]pyridine-3-carbonyl]-pyridin-3-yl}-2-(5-methyl-3-trifluoromethyl-pyrazol-1-yl)-acetamide;
2-(3-Cyclopropyl-pyrazol-1-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
2-(5-Chloro-pyridin-2-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-pyrazol-1-yl)-acetamide;
N-{5-[7-Fluoro-1-(2-hydroxy-1,1-dimethyl-ethyl)-1H-pyrrolo[3,2-c]pyridine-3-carbonyl]-pyridin-3-yl}-2-(3-trifluoromethyl-phenyl)-acetamide;
2-(4-Chloro-phenyl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-phenyl)-acetamide; and
2-(5-Chloro-pyridin-2-yl)-N-{5-[1-(2-hydroxy-1,1-dimethyl-ethyl)-1H-pyrrolo[3,2-c]pyridine-3-carbonyl]-pyridin-3-yl}-acetamide,
or a pharmaceutically acceptable salt thereof.

Embodiment 11: A pharmaceutical composition comprising a compound of the formula (I) or a pharmaceutically acceptable salt thereof, as defined in any one of the preceding embodiments 1 to 10, and a pharmaceutically acceptable carrier.

Embodiment 12: A compound of the formula (I) or a pharmaceutically acceptable salt thereof, as defined in any one of embodiments 1 to 10, for use as a medicament.

Embodiment 13: A compound of formula (I) or a pharmaceutically acceptable salt thereof, as defined in any one of embodiments 1 to 10 for use in the treatment of a disease for which an Trk receptor antagonist is indicated.

Embodiment 14: A compound of formula (I) or a pharmaceutically acceptable salt thereof, as defined in any one of embodiments 1 to 10 for use in the treatment of pain or cancer.

Embodiment 15: The use of a compound of the formula (I) or a pharmaceutically acceptable salt or composition thereof, as defined in any one of embodiments 1 to 10, for the manufacture of a medicament to treat a disease for which an Trk receptor antagonist is indicated Embodiment 16: The use of a compound of the formula (I) or a pharmaceutically acceptable salt or composition thereof, as defined in any one of embodiments 1 to 10, for the manufacture of a medicament to treat pain or cancer.

Embodiment 17: A method of treatment of a mammal, to treat a disease for which an Trk receptor antagonist is indicated, comprising treating said mammal with an effective amount of a compound of the formula (I) or a pharmaceutically acceptable salt thereof, as defined in any one of embodiments 1 to 10.

Embodiment 18: A method of treatment of pain or cancer in a mammal, comprising treating said mammal with an effective amount of a compound of the formula (I) or a pharmaceutically acceptable salt thereof, as defined in any one of embodiments 1 to 10.

Embodiment 19: A compound or salt according to any one of embodiments 1 to 10 for use in a medical treatment in combination with a further drug substance.

Further embodiments include:
A compound or salt according to any one of embodiments wherein $R^4$ has the value of $R^4$ in any of the Examples;
A compound or salt according to any one of embodiments wherein $R^{102}$ has the value of $R^{102}$ in any of the Examples;
A compound or salt according to any one of embodiments wherein $R^1$ has the value of $R^1$ in any of the Examples;
A compound or salt according to any one of embodiments wherein $R^{B,C,D}$ has the value of $R^{B,C,D}$ in any of the Examples;
A compound or salt according to any one of embodiments wherein X has the value of X in any of the Examples;
A compound selected from any of the Examples herein described, or a pharmaceutically acceptable salt thereof;
Any novel genus of intermediates described in the Schemes below;
Any novel specific intermediate described in the Preparations below;
Any novel process described herein.

"Halogen" means a fluoro, chloro, bromo or iodo group.
"Alkyl" groups, containing the requisite number of carbon atoms, can be unbranched or branched. Examples of alkyl include methyl, ethyl, n-propyl, i-propyl, n-butyl, i-butyl, sec-butyl and t-butyl.

"Pharmaceutically acceptable salts" of the compounds of formula I include the acid addition and base addition salts (including disalts, hemisalts, etc.) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base addition salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

The compounds of the invention include compounds of formula I and salts thereof as hereinbefore defined, polymorphs, and isomers thereof (including optical, geometric and tautomeric isomers) as hereinafter defined and isotopically-labelled compounds of formula I.

Unless otherwise specified, compounds of formula (I) containing one or more asymmetric carbon atoms can exist as two or more stereoisomers. Where a compound of formula (I) contains for example, a keto or guanidine group or an aromatic moiety, tautomeric isomerism ('tautomerism') can occur. It follows that a single compound may exhibit more than one type of isomerism.

Included within the scope of the claimed compounds of the present invention are all stereoisomers, geometric isomers and tautomeric forms of the compounds of formula (I), including compounds exhibiting more than one type of isomerism, and mixtures of one or more thereof. Also included are acid addition or base addition salts wherein the counterion is optically active, for example, D-lactate or L-lysine, or racemic, for example, DL-tartrate or DL-arginine.

Examples of types of potential tautomerisms shown by the compounds of the invention include hydroxypyridine ⇔ pyridone; amide ⇔ hydroxyl-imine and keto ⇔ enol tautomersims:

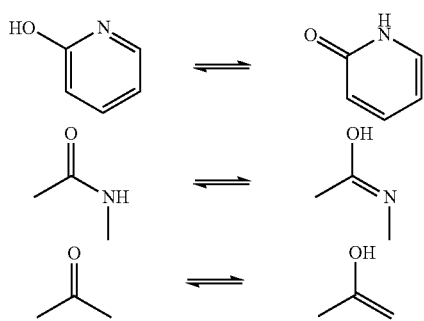

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or other derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$O, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the general synthetic methods below, unless otherwise specified, the substituents are as defined above with reference to the compounds of formula (I) above.

Where ratios of solvents are given, the ratios are by volume.

According to a first process, compounds of formula (I) may be prepared by the process illustrated in Scheme 1.

Typical conditions employed involve stirring the amine of general formula (II) and the acid of general formula (III) together with a suitable coupling reagent such as HATU, EDCI/HOBt or 1-propylphosphonic acid cyclic anhydride, if necessary adding a suitable base such as NMM, DIPEA or TEA in a suitable solvent such as pyridine, THF, DMF or DMA at a temperature from room temperature up to 70° C. A suitable alternative is to use an additive (such as 4-dimethylaminopyridine) as well as a base. Any suitable solvent may be used in place of those mentioned above. At least one equivalent of the acid (III) and at least one equivalent of the coupling reagent should be used and an excess of one or both may be used if desired.

Where $R^1$ contains a suitable hydroxyl protecting group in intermediate (II), removal of the protecting group (PG) can be done in situ or as an additional step, adding a suitable acid and organic solvent to the crude residue after the amide formation has taken place. Common protecting groups to use include TBDMS, which is readily removed by treatment with an acid such as aqueous hydrogen chloride or aqueous citric acid in an organic solvent such as THF or by treatment with a fluoride source such as tetrabutylammonium fluoride in an organic solvent such as THF, and THP. Preferred conditions comprise 4M/10% HCl in 1,4-dioxane at room temperature.

Intermediates of general formula (III) are either commercially available or will be well-known to those skilled in the art with reference to literature precedents and/or the preparations herein.

Compounds of general formula (II) are described in Scheme 3, 4 and 5.

According to a second process, Compounds of formula (I) wherein $R^{102}$ is 5-cyanopyridine (IB) may be prepared from compounds of formula (I) wherein $R^{102}$ is 5-halopyridine (IA), by the process illustrated in Scheme 2.

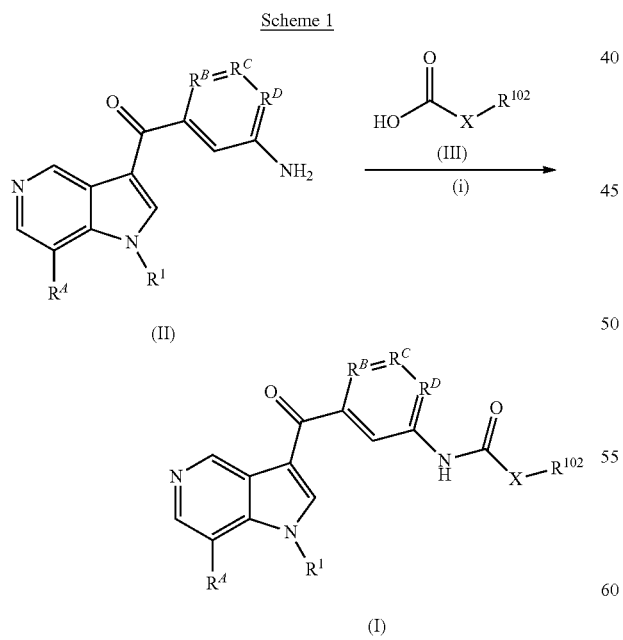

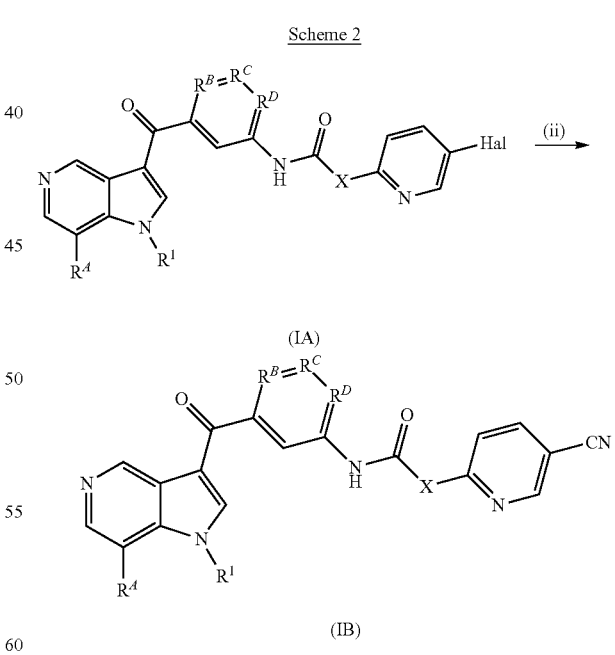

Compounds of formula (I) may be prepared from compounds of formula (II) according to process step (i), an amide bond formation step, if necessary adding a suitable base (such as DIPEA) and/or additive (such as DMAP).

Compounds of formula (IB) may be prepared from compounds of formula (IA) wherein Hal is Cl, Br or I; according to process step (ii), a palladium catalysed cyanation step. Typical conditions comprise zinc cyanide with tris(dibenzylideneacetone)dipalladium (0) and DPPF in DMF at 100° C.

Compounds of formula (IA) may be prepared as described in Scheme 1.

According to a third process, compounds of formula (II) may be prepared by the process illustrated in Scheme 3.

According to a fourth process, compounds of formula (II) may be prepared by the process illustrated in Scheme 4.

preparations herein. Compounds of formula (VA), (VB), and (VC) described in Scheme 8 may be used in Scheme 3.

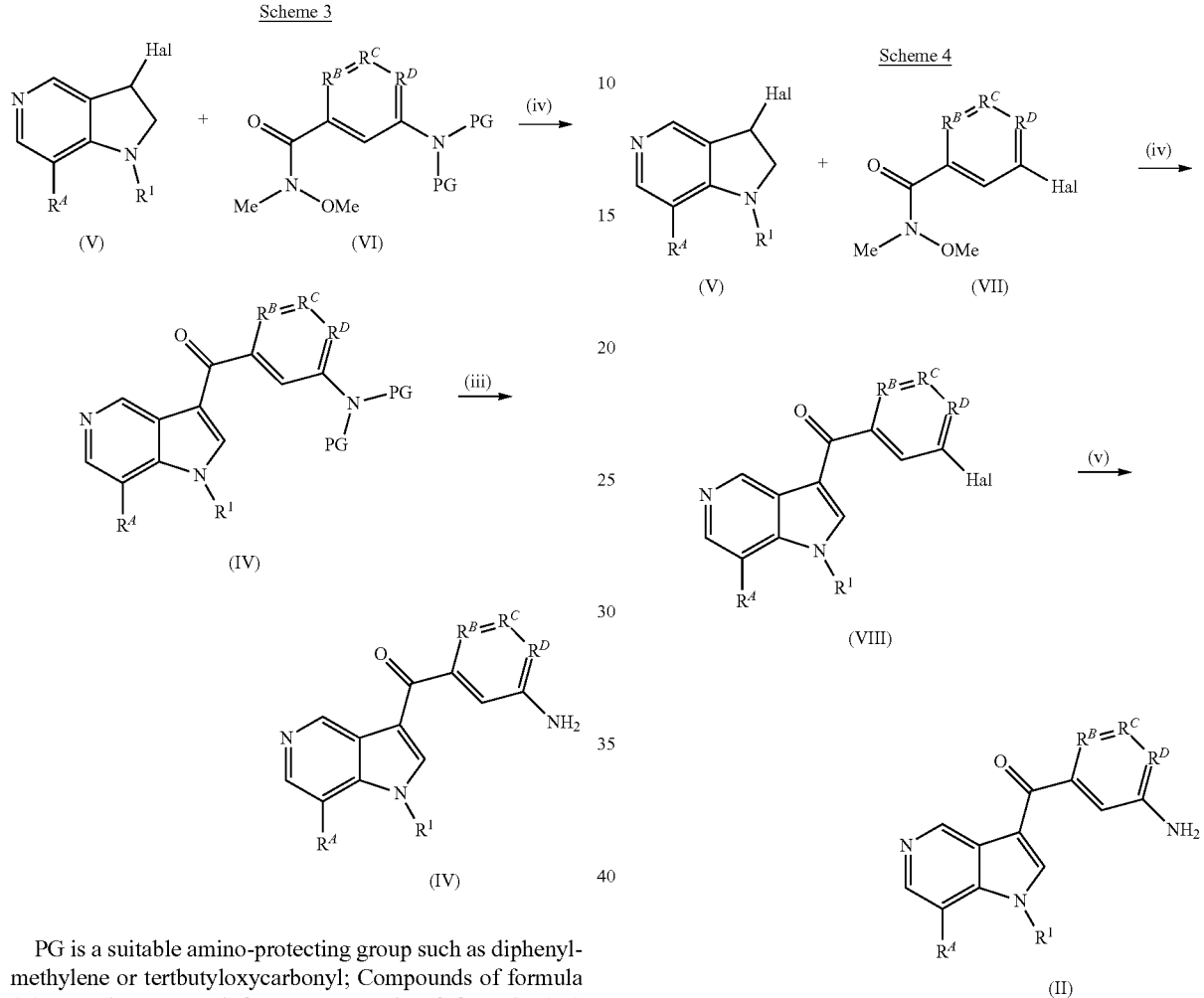

PG is a suitable amino-protecting group such as diphenylmethylene or tertbutyloxycarbonyl; Compounds of formula (II) may be prepared from compounds of formula (IV) according to process step (iii), a deprotection step conveniently mediated under acidic conditions using acids such as HCl, TFA or citric acid. Wherein PG is tertbutyloxycarbonyl, preferred conditions comprise TFA in DCM at room temperature. Wherein PG is diphenylmethylene, preferred conditions comprise a 1M aqueous solution of citric acid in THF at room temperature, TFA in DCM at room temperature or 0.5M HCl in THF at room temperature.

Compounds of formula (IV) may be prepared from compounds of formula (V) and (VI) according to process step (iv), a metallation of intermediate halide (V) (using a suitable organometallic reagent such as butyllithium or isopropylmagnesium chloride) and reacting with the Weinreb amide intermediate (VI) at a temperature from −78° C. up to room temperature in a suitable solvent such as THF.

Preferred conditions comprise nBuLi in THF at −78° C. or iPrMgCl in THF at 0° C. Compounds of formula (V) are described in Scheme 7. Compounds of formula (VI) are either commercially available or will be well-known to those skilled in the art with reference to literature precedents and/or the Compounds of formula (II) may be prepared from compounds of formula (VIII) according to process step (v), a direct amination of the halide using standard literature conditions. For example, amine (II) is typically prepared using ammonia with a suitable copper catalyst such as copper (II) sulphate or copper (I) oxide in suitable solvent such as NMP in a sealed vessel at a temperature between room temperature and 140° C. Compounds of formula (VIII) may be prepared from compounds of formula (V) and (VII) according to process step (iv) as described in Scheme 3 from the suitable Weinreb reagent.

Compounds of formula (VII) are either commercially available or will be well-known to those skilled in the art with reference to literature precedents and/or the preparations herein.

Compounds of formula (V) are described in Scheme 7.

According to a fifth process, compounds of formula (II) may be prepared by the process illustrated in Scheme 5.

Scheme 5

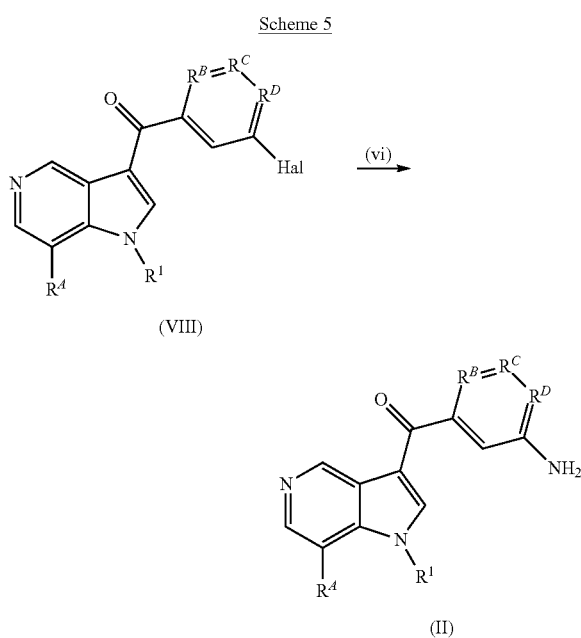

Compounds of formula (II) may be prepared from compounds of formula (VIII) according to process step (vi), a palladium catalysed amination reaction followed by an acid mediated deprotection reaction, as previously described with regard to Scheme 3. Typical conditions comprise using benzophenone imine with a suitable base such as sodium tert-butoxide in the presence of a ligand such as tBuXphos, catalysed by a palladium species such as tris(dibenzylideneacetone)dipalladium in toluene at room temperature followed by TFA in DCM at room temperature.

Compounds of formula (VIII) may be prepared as described in Scheme 4.

According to a sixth process, compounds of formula (VIII) may be prepared by the process illustrated in Scheme 6.

Scheme 6

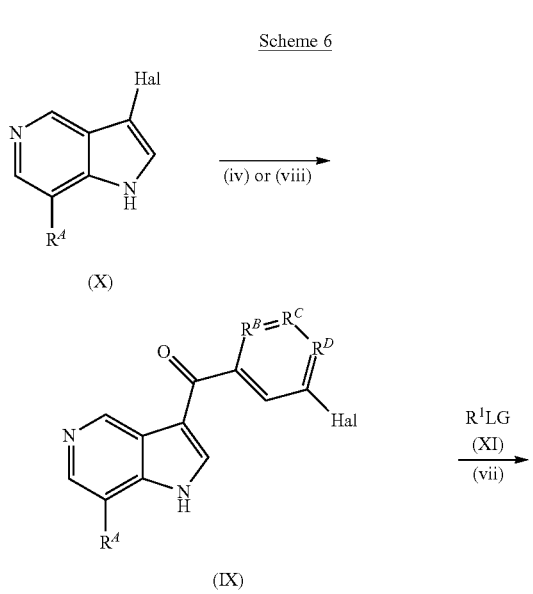

Compounds of formula (VIII) may be prepared from compounds of formula (IX) according to process step (vii), an alkylation step with compounds of formula (XI) wherein LG can be halogen or tosylate, mesylate or triflate. Preferred conditions comprise an inorganic base such as cesium carbonate in DMF at room temperature. Compounds of formula (XI) are either commercially available or the preparation is described herein.

Compounds of formula (IX) may be prepared from compounds of formula (X) according to process step (iv) as described in Scheme 3 or according to process step (viii), a Friedal-Crafts acylation reaction. Typical conditions comprise aluminium trichloride with 2-chloroisonicotinylchloride in DCE at 70° C.

Compounds of formula (X) are described in Scheme 7.

According to a seventh process, compounds of formula (V) may be prepared by the process illustrated in Scheme 7.

Scheme 7

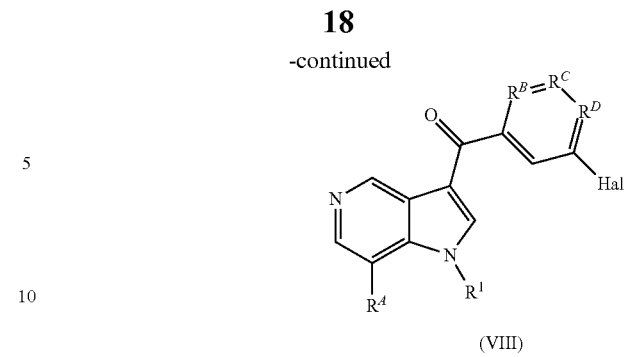

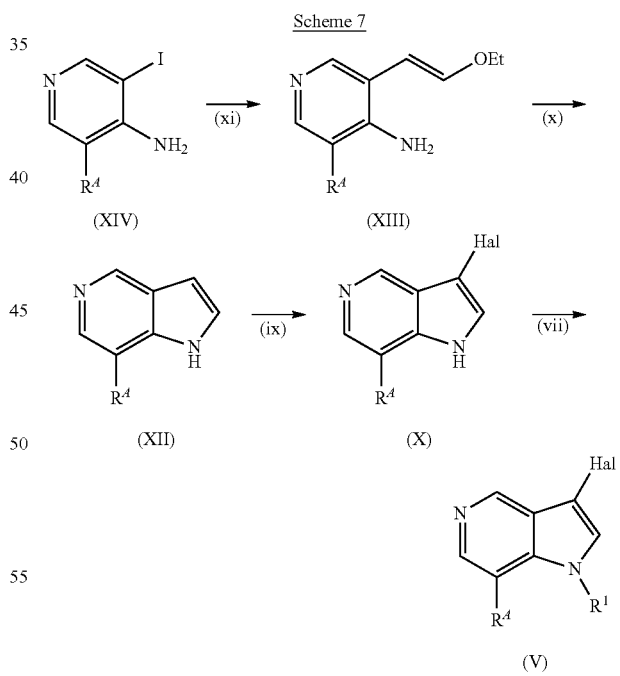

Compounds of formula (V) may be prepared from compounds of formula (X) according to process step (vii), an alkylation step as described in Scheme 6.

Compounds of formula (X) may be prepared from compounds of formula (XII) according to process step (ix), an electrophilic halogenation reaction. Typical conditions comprise either NIS or NBS in DMF at room temperature.

Compounds of formula (XII) may be prepared from compounds of formula (XIII) according to process step (x), a cyclisation reaction mediated by acid. Preferred conditions comprise cHCl in ethanol at reflux.

Compounds of formula (XIII) may be prepared from compounds of formula (XIV) according to process step (xi), a Suzuki cross coupling reaction. The vinyl ether can be introduced by reacting intermediate (XIV) with a suitable boronic ester and a suitable base, such as sodium hydroxide and a suitable catalyst such as tetrakis(triphenylphosphine)palladium (0) in a solvent such as THF at a temperature from room temperature up to 70° C.

Compounds of formula (XIV) are either commercially available or the preparation is described herein.

According to an eighth process, compounds of formula (VA) and (VB) may be prepared by the process illustrated in Scheme 8.

potassium tertbutoxide in THF at room temperature with an suitable alkylating agent such as methyl iodide.

Compounds of formula (XVI) may be prepared from compounds of formula (X) according to process step (vii), an alkylation step as described in Scheme 6.

Compounds of formula (X) may be prepared as described in Scheme 7.

According to a further embodiment the present invention provides novel intermediate compounds.

Pharmaceutically acceptable salts of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

Scheme 8

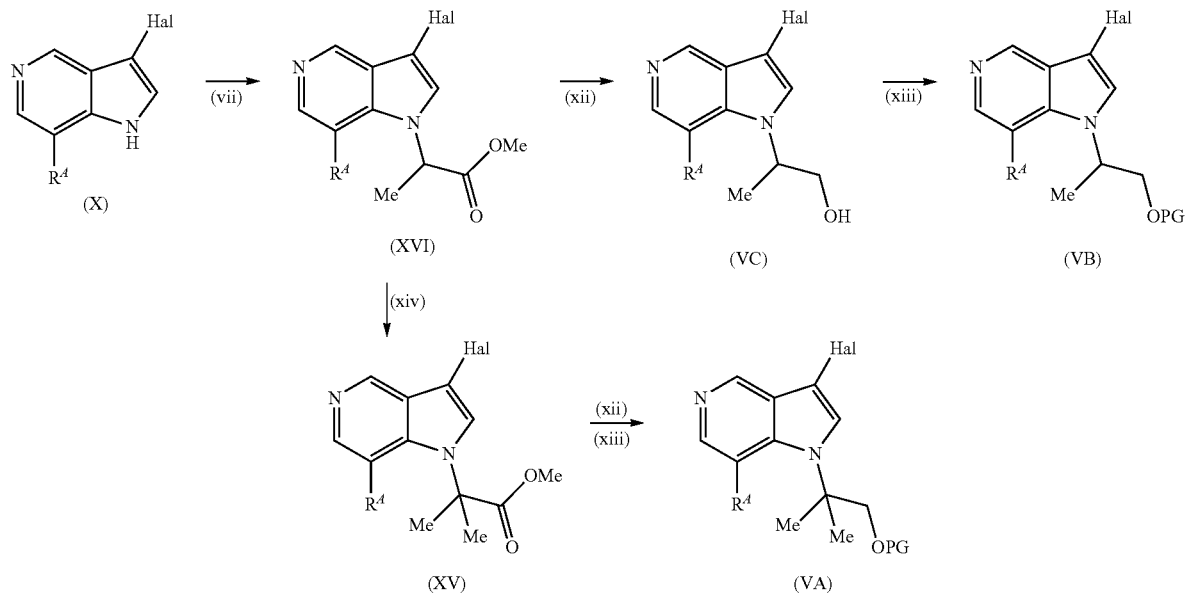

Compounds of formula (VB) may be prepared from compounds of formula (VC) using process step (xiii), a protection step. As previously mentioned in Scheme 1 the hydroxy group can be protected with a suitable oxygen protecting group (PG), where the preferred protecting groups are TBDMS, TBS and THP. Typical conditions comprise TBDMSCl in DCM at 0° C. with imidazole.

Compounds of formula (VC) may be prepared from compounds of formula (XVI) according to process step (xii), a reduction step. Reduction of the ester intermediate (XVI) can be effected by using a suitable reducing reagent such as lithium borohydride, lithium aluminium hydride or diisobutylalumnium hydride in a suitable solvent such as ethanol or THF. Preferred conditions comprise lithium borohydride in THF at 0° C. or sodium borohydride in EtOH at room temperature.

Compounds of formula (VA) may be prepared from compounds of formula (XV) according to process steps (xii) and (xiii) as described above.

Compounds of formula (XV) may be prepared from compounds of formula (XVI) according to process step (xiv), a further alkylation step. Typical conditions comprise 1M The compounds of the invention intended for pharmaceutical use may be administered alone or in combination with one or more other compounds of the invention or in combination with one or more other drug agent (or as any combination thereof). Generally, they will be administered as a formulation in association with one or more pharmaceutically acceptable excipients. The term "excipient" is used herein to describe any biologically inactive ingredient other than the compounds and salts of the invention. The choice of excipient will to a large extent depend on factors such as the particular mode of administration, the effect of the excipient on solubility and stability, and the nature of the dosage form. For example, a compound of the formula I, or a pharmaceutically acceptable salt or solvate thereof, as defined above, may be administered simultaneously (e.g. as a fixed dose combination), sequentially or separately in combination with one or more other drug agent.

Exemplary additional agents could be selected from one or more of:
 a Nav1.7 channel modulator, such as a compound disclosed in WO 2009/012242 or WO2010/079443;
 an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);

an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagoinsist;

a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)]-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5\text{-}HT_{1B/1D}$ agonist such as eletriptan, sumatriptan, naratriptan, zolmitriptan or rizatriptan;

a $5\text{-}HT_{2A}$ receptor antagonist such as R(+)-alpha-(2,3-dimethoxy-phenyl)-1-[2-(4-fluorophenylethyl)]-4-piperidinemethanol (MDL-100907);

a $5\text{-}HT_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2′,1′:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-Nyrimidin-2-yl methyl) pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl]phenoxy-methyl]-1-methyl-2-quinolone (ZD-2138), or 2,3,5-trimethyl-6-(3-pyridylmethyl), 1,4-benzoquinone (CV-6504).

Pharmaceutical compositions suitable for the delivery of compounds and salts of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Compounds and salts of the invention intended for pharmaceutical use may be prepared and administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. [Make sure these specific ranges are relevant]

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed above may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds and salts of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) and salts used in the preparation of parenteral solutions may be increased by the use of appropriate formulation techniques, such as the incorporation of solubility-enhancing agents.

Formulations for parenteral administration may be formulated to be immediate and/or modified release. Thus, compounds and salts of the invention may be formulated as a solid, semi-solid, or thixotropic liquid for administration as an implanted depot providing modified release of the active compound. An example of such formulations include drug-coated stents.

Topical Administration

The compounds and salts of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, Finnin and Morgan, J Pharm Sci, 88 (10), 955-958 (October 1999).] Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds and salts of the invention may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

A pressurised container, pump, spray, atomizer, or nebuliser may contain a solution or suspension of the compound(s) or salt(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound or salt of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound or salt of the invention per actuation and the actuation volume may vary from 1 µl to 100 µl. A typical formulation may comprise a compound of formula (I) or salt thereof, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 1 to 5000 μg of the compound or salt. The overall daily dose will typically be in the range 1 μg to 20 mg which may be administered in a single dose or, more usually, as divided doses throughout the day.

Rectal/Intravaginal Administration

The compounds and salts of the invention may be administered rectally or vaginally, for example, in the form of a suppository, pessary, or enema. Cocoa butter is a traditional suppository base, but various well known alternatives may be used as appropriate.

Ocular and Aural Administration

The compounds and salts of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis.

Other Technologies

The compounds and salts of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds and salts of the invention is typically in the range 0.1 mg to 200 mg depending, of course, on the mode of administration, preferred in the range 1 mg to 100 mg and more preferred in the range 1 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the above-mentioned therapeutic uses, the dosage administered will, of course, vary with the compound or salt employed, the mode of administration, the treatment desired and the disorder indicated. The total daily dosage of the compound of formula (0/salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions.

The pharmaceutical composition may, for example, be in a form suitable for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

For parenteral dosages, this may conveniently be prepared as a solution or as a dry powder requiring dissolution by a pharmacist, medical practitioner or the patient. It may be provided in a bottle or sterile syringe. For example it may be provided as a powder in a multicompartment syringe which allows the dry powder and solvent to be mixed just prior to administration (to aid long-term stability and storage). Syringes could be used which allow multiple doses to be administered from a single device.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems.

Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The precise dosage administered of each active ingredient will vary depending upon any number of factors, including but not limited to, the type of animal and type of disease state being treated, the age of the animal, and the route(s) of administration.

The following non-limiting Preparations and Examples illustrate the preparation of compounds and salts of the present invention.

GENERAL EXPERIMENTAL

The Preparations and Examples that follow illustrate the invention but do not limit the invention in any way. All starting materials are available commercially or described in the literature. All temperature are in ° C. Flash column chromatography was carried out using Merck silica gel 60 (9385) or Redisep silica. NMR was carried out using a Varian Mercury 400 MHz NMR spectrometer or a Jeol ECX 400 MHz NMR. Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

Where singleton compounds have been analysed by LCMS, there are several methods used. These are illustrated below.

The invention is illustrated by the following non-limiting Examples in which the following abbreviations and definitions are used:

AcOH—acetic acid; APCI—atmospheric pressure chemical ionization; Arbocel is a filter agent; br s—broad singlet; BINAP—2,2'-bis(diphenylphosphino)-1,1'-binapthyl; nBuLi—n-Butyllithium; $CDCl_3$—deuterated chloroform; $Cs_2CO_3$ is caesium carbonate; CuI is copper (I) iodide; $Cu(OAc)_2$ is copper (II) acetate; δ—chemical shift; d—doublet; DAD—diode array detector; DCE—1,2-dichloroethane DCM—dichloromethane; DEA—diethylamine; DIBAL—Diisobutylaluminium hydride; DIPEA—diisopropylethylamine; DMAP—4-dimethylaminopyridine; DME—dimethoxyethane; DMF—N,N-dimethylformamide; DMF-DMA—N,N-dimethylformamide-dimethylacetal; DMSO—dimethylsulphoxide DPPF—1,1'-bis(diphenylphosphino)ferrocene; ELSD—evaporative light scattering detector; ESI—electrospray ionization; $Et_2O$—diethylether; EtOAc/EA—ethyl acetate; EtOH—ethanol; g—gram; HATU—2-(7-azabenzotriazol-1-yl)-1,1,3,3-tetramethyluronium hexafluorophosphate; HBTU is O-benzotriazol-1-yl-N,N,N',N'-tetramethyluronium hexafluorophosphate; HCl is hydrochloric acid; HOBT is N-hydroxybenzotriazole hydrate; HPLC—high pressure liquid chromatography; IPA—isopropyl alcohol; $K_2OC_3$ is potassium carbonate; $KHSO_4$ is potassium hydrogen sulphate; KOAc is potassium acetate; KOH is potassium hydroxide; $K_3PO_4$ is potassium phosphate tribasic; KF—potassium fluoride; L is liter; LCMS—liquid chromatography mass spectrometry; LiHMDS—Lithium hexamethyldisilazide; m—multiplet; mg—milligram; mL—milliliter; M/Z—Mass Spectrum Peak; MeCN—acetonitrile; MeOH—methanol; 2-MeTHF—2-methyltetrahydrofuran; $MgSO_4$ is magnesium sulphate; $MnO_2$—manganese dioxide; $NaClO_2$—sodium chlorite; NaH—sodium hydride; $NaHCO_3$—sodium hydrogencarbonate; $Na_2CO_3$—sodium carbonate; $NaH_2PO_4$—sodium phosphate; $NaHSO_3$—sodium bisulphite; $NaHSO_4$—sodium hydrogensulphate; NaOH—sodium hydroxide; $Na_2SO_4$—sodium sulphate; $NH_3$—ammonia; $NH_4Cl$—ammonium chloride; NMM—N-MethylMorpholine; NMR—nuclear magnetic resonance; Pd/C—palladium on carbon; $PdCl_2$—palladium dichloride; $Pd_2(dba)_3$ is tris(dibenzylideneacetone)dipalladium(0); $Pd(PPh_3)_4$—palladium tetrakis(triphenylphosphine); $Pd(OAc)_2$—palladium acetate; PTSA—para-toluenesulfonic acid; Prep—preparation; $R_t$—retention time; q—quartet; s—singlet; TBDMS—tertbutyldimethylsilyl; TBME—tert-butyldimethylether; TCP—1-propylphosphonic acid cyclic anhydride; TEA—triethylamine; TFA—trifluoroacetic acid; THF—tetrahydrofuran; TLC—thin layer chromatography; (R,S)—racemic mixture; WSCDI—1-(3-dimethylaminopropyl)-3-ethylcarbodiimide hydrochloride.

For the avoidance of doubt, named compounds used herein have been named using IUAPC, Chemdraw and/or Name Pro ACD Labs Name Software v7.11™ or using other standard nomenclature. NMR spectra were measured in deuterated solvents and were consistent with the names/structures given below.

"CommAv" means a commercially available intermediate/reagent.

The mass spectra were obtained using:
Waters ZQ ESCI
Applied Biosystem's API-2000 5 min LC-MS
Waters Alliance 2795 with ZQ2000 (ESI)
Aglient 110 HPLC 5 min (System 5)
Waters ZQ ESCI 8 min LC-MS
Waters Alliance 2695 with ZQ2000 (ESI) 25 min
HP 1100 HPLC with Waters Micromass ZQ mass detector 12.5 min LC-MS
UPLC mass spectra were obtained using a Waters Acquity ZQD (ESI) 1.5 min LC-MS
WATERS ACQUITY UPLC/WATERS 3100 MSD/PL-ELS 2100 ICE ELSD Where singleton compounds have been analysed by LCMS, several methods were used. These are illustrated below.

System 2
2 minute LC-MS gradient and instrument conditions
A: 0.1% formic acid in water
B: 0.1% formic acid in acetonitrile
Column: C18 phase Phenomenex 20×4.0 mm with 3 micron particle size
Gradient: 70-2% A over 1.5 min, 0.3 min hold, 0.2 re-equilibration, 1.8 mL/min flow rate
UV: 210 nm—450 nm DAD
Temperature: 75° C.

System 3
5 minute LC-MS gradient and instrument conditions
A: 0.1% formic acid in water
B: 0.1% formic acid in acetonitrile
Column: C18 phase Waters Sunfire 50×4.6 mm with 5 micron particle size
Gradient: 95-5% A over 3 min, 1 min hold, 1 min re-equilibration, 1.5 mL/min flow rate
UV: 225 nm—ELSD-MS
Temperature: ambient System 4
5 minute LC-MS gradient and instrument conditions
A: 0.1% ammonium hydroxide in water
B: 0.1% ammonium hydroxide in acetonitrile
Column: C18 phase XTerra 50×4.6 mm with 5 micron particle size
Gradient: 95-5% A over 3 min, 1 min hold, 1 min re-equilibration, 1.5 mL/min flow rate
UV: 225 nm—ELSD-MS
Temperature: ambient System 5
5 minute LC-MS gradient and instrument conditions
A: 0.0375% TFA in water B: 0.01875% TFA in acetonitrile
Column: C18 phase Welch XB 50×2.1 mm with 5 micron particle size
Gradient: 99-0% A over 4 min, 0.70 min re-equilibration, 0.8 mL/min flow rate
UV: 225 nm—ELSD-MS
Temperature: 50° C.
System 6
5 minute LC-MS gradient and instrument conditions
A: 0.0375% TFA in water
B: 0.01875% TFA in acetonitrile
Column: C18 phase Welch XB 50×2.1 mm with 5 micron particle size
Gradient: 90-0% A over 4 min, 0.70 min re-equilibration, 0.8 mL/min flow rate
UV: 225 nm—ELSD-MS
Temperature: 50° C.
System 9
5 minute LC-MS gradient and instrument conditions
A: 0.05% formic acid in water
B: acetonitrile
Column: C18 phase XBridge 50×4.6 mm with 5 micron particle size
Gradient: 90-10% A over 3 min, 1 min hold, 1min re-equilibration, 1.2 mL/min flow rate
UV: 200 nm—260 nm DAD
Temperature: 25° C.
System 10
5 minute LC-MS gradient and instrument conditions
A: 10 mM ammonium acetate in water
B: acetonitrile
Column: C18 phase Gemini NX 50×4.6 mm with 5 micron particle size
Gradient: 90-10% A over 3 min, 1 min hold, 1min re-equilibration, 1.2 mL/min flow rate
UV: 200 nm—260 nm DAD
Temperature: 25° C.
LCMS QC conditions for library protocol 4/5
3 minute LC-MS gradient and instrument conditions
A: 0.05% formic acid in water
B: Acetonitrile
Column: RESTEK C18 30×2.1 mm 3 micron particle size
Gradient: Initial: 98% A; 2% B; 0.75 mins 98% A, 2% B; 1 min 90% A, 10% B; 2 mins 2% A,
98% B; 2.25 mins 2% A, 98% B; 2.90 mins 98% A, 2% B; 3 mins 98% a, 2% B.
Flow rate: 1.50 mL/min
UV: 215 nm—ELSD-MS
Temperature: 50° C.
12 min runtime LCMS conditions
A: 0.05% formic acid in water/10 mM ammonium acetate in water
B: acetonitrile
  Column (Name, Size, type):
  1. Gemini NX C18 4.6×50 mm, 5 micron
  2. Xbridge C18 4.6×50 mm, 5 micron
  3. Reprosil 4.6×50 mm, 5 micron
  4. Zorbax Extend C18 4.6×50 mm, 5 micron
  LC-MS gradient:
  Gradient held for 1 min at 95% [Buffer] and 5% [CH$_3$CN] with a gradual change to 50% [Buffer] and 50% [CH$_3$CN] in 7 min, further to 10% [Buffer] and 90% [CH3CN] in 10 min, held this mobile phase composition to 11 min and finally back to initial condition in 12 min.
  Flow rate: mL/min: 1.0 ml/min

| TIME | MODULE | % A (Buffer) | % B (CH3CN) |
|---|---|---|---|
| 0.01 | Pumps | 95 | 5 |
| 1.00 | Pumps | 95 | 5 |
| 7.00 | Pumps | 50 | 50 |
| 10.00 | Pumps | 10 | 90 |
| 11.00 | Pumps | 10 | 90 |
| 12.00 | Pumps | 95 | 5 |
| 12.10 | System Controller | Stop | |

UV: 220 nm and 260 nm
Temperature: 25° C.
Where singleton compounds have been purified by High Performance Liquid Chromatography, unless otherwise stated, one of four methods were used, and these are shown below.
Waters Purification Systems with mass spec or UV detection
Prep System 1
10 minute prep LC-MS gradient and instrument conditions
A: 0.1% formic acid in water
B: 0.1% formic acid in acetonitrile
Column: C18 phase Sunfire 100×19.0 mm
Gradient: 95-2% A over 7 min, 2 min hold, 1 min re-equilibration, 18 mL/min flow rate
Temperature: ambient
Prep System 2
10 minute prep LC-MS gradient and instrument conditions
A: 0.1% DEA in water
B: 0.1% DEA in acetonitrile
Column: C18 phase Xterra 100×19.0 mm
Gradient: 95-2% A over 7 min, 2 min hold, 1 min re-equilibration, 18 mL/min flow rate
Temperature: ambient
Prep System 3
7 minute prep LC-MS gradient and instrument conditions
A: 0.05% ammonia in water
B: acetonitrile
Column: C18 phase Xbridge 50×19.0 mm
Gradient: 90-20% A over 7 min, 20 mL/min flow rate
Temperature: ambient
Prep System 4
8 minute prep LC-MS gradient and instrument conditions
A: 0.1% TFA in water
B: acetonitrile
Column: C18 phase Sepax BR 100×21.2 mm
Gradient: 96-33% A over 8 min, 30 mL/min flow rate
Temperature: ambient
Method: 1
Mobile phase:—A: 5 mM NH$_4$OAc in H$_2$O; B: Acetonitrile
Column name:—X Bridge Prep C$_{18}$ 5µ OBD (19×250 mm)
Gradient: 90-10% A over 16 min, 4 min hold, 3 min re-equilibration, 14.0 mL/min flow rate
Temperature: ambient
Waters auto purification instrument with PDA
Method: 2
Mobile phase:—A: 0.05% HCOOH in H$_2$O; B: Acetonitrile
Column name:—X terra Prep RP18 10µ (19×250 mm)
Gradient: 90-10% A over 16 min, 4 min hold, 3 min re-equilibration. 14.0 mL/min flow rate
Temperature: ambient
Waters auto purification instrument with PDA
Method: 3
Mobile phase:—A: 0.1% NH$_3$ in H$_2$O; B: Acetonitrile
Column name:—Gemini-NX 5µ C18 110 A (100×30 mm)
Gradient: 90-10% A over 10 min, 2 min hold, 1 min re-equilibration. 30.0 mL/min flow rate
Temperature: ambient
Waters auto purification instrument with PDA

Example 1

N-{5-[7-Fluoro-1-(2-hydroxy-1,1-dimethyl-ethyl)-1H-pyrrolo[3,2-c]pyridine-3-carbonyl]-pyridin-3-yl}-2-(5-methyl-3-trifluoromethyl-pyrazol-1-yl)-acetamide

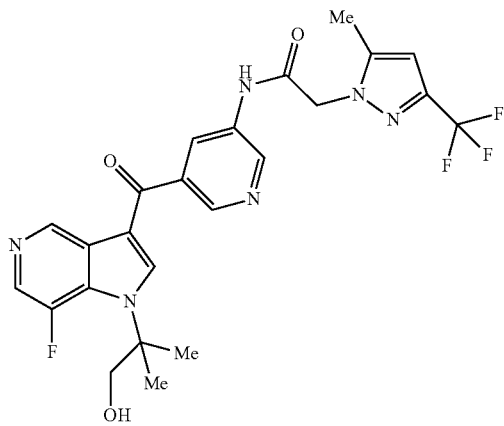 [SMILES: Cc1cc(C(F)(F)F)nn1CC(=O)Nc1cncc(C(=O)c2cn(C(C)(C)CO)c3c(F)cncc23)c1]

Method Y a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(5-methyl-3-trifluoromethyl-pyrazol-1-yl)-acetamide (Preparation 7, 37 mg, 58 µmol) in THF (5 mL) 4M dioxane-HCl (0.5 mL) was added and stirred at room temperature for 18 hours. The reaction was evaporated in vacuo and triturated with pentane-ether to afford the title compound as an off white solid in 86% yield, 26 mg.

$^1$H NMR (400 MHz, DMSO-d$_6$): δ ppm 1.61 (s, 6H), 2.29 (s, 3H), 3.75 (s, 2H), 5.16 (s, 2H), 6.53 (s, 1H), 8.25 (s, 1H), 8.46 (s, 1H), 8.61 (d, 1H), 8.75 (s, 1H), 8.96 (s, 1H), 9.40 (s, 1H).

LCMS: R$_t$=2.92 minutes m/z 519 [M+H]$^+$

Example 2

2-(3-Cyclopropyl-pyrazol-1-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide

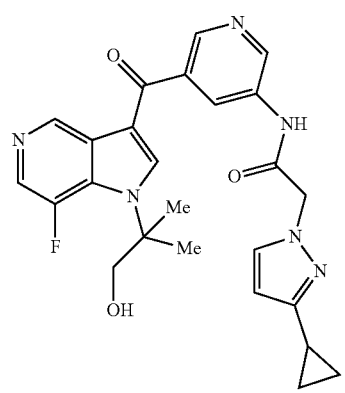 [SMILES: CC(C)(CO)n1cc(C(=O)c2cncc(NC(=O)Cn3ccc(C4CC4)n3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(3-cyclopropyl-pyrazol-1-yl)-acetamide (Preparation 6, 40 mg, 67 µmol) in THF (5 mL) 4M dioxane-HCl (1 mL) was added and stirred at room temperature for 18 hours. The reaction was evaporated in vacuo and triturated with pentane-ether to afford the title compound as an off white solid in 92% yield, 30 mg.

$^1$H NMR (400 MHz, DMSO-d$_6$): δ ppm 0.60 (d, 2H), 0.81 (m, 2H), 1.66 (s, 6H), 1.84 (m, 1H), 3.85 (s, 2H), 5.00 (s, 2H), 5.96 (d, 1H), 7.62 (d, 1H), 8.36 (s, 1H), 8.52 (s, 1H), 8.76 (m, 2H), 9.03 (d, 1H), 9.48 (s, 1H), 10.97 (s, 1H).

LCMS: R$_t$=2.82 minutes m/z 477 [M+H]$^+$

Example 3

2-(5-Chloro-pyridin-2-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide

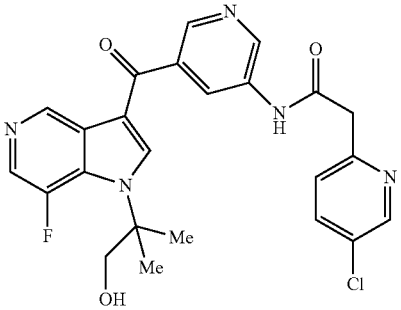 [SMILES: CC(C)(CO)n1cc(C(=O)c2cncc(NC(=O)Cc3ccc(Cl)cn3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(5-chloro-pyridin-2-yl)-acetamide (Preparation 5, 30 mg, 62 µmol) in THF (5 mL) 4M dioxane-HCl (0.5 mL) was added and stirred at room temperature for 4 hours. The reaction was evaporated in vacuo and triturated with pentane-ether to afford the title compound as a white solid in 100% yield, 24.3 mg.

$^1$H NMR (400 MHz, DMSO-d$_6$): δ ppm 1.65 (s, 6H), 3.84 (s, 2H), 3.97 (s, 2H), 7.49 (d, 1H), 7.92 (d, 1H), 8.31 (s, 1H), 8.54 (s, 1H), 8.69 (d, 1H), 8.76 (s, 1H), 9.00 (s, 1H), 9.46 (s, 1H), 10.87 (s, 1H).

LCMS: R$_t$=2.75 minutes; m/z 482 [M+H]$^+$

Example 4

N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-pyrazol-1-yl)-acetamide

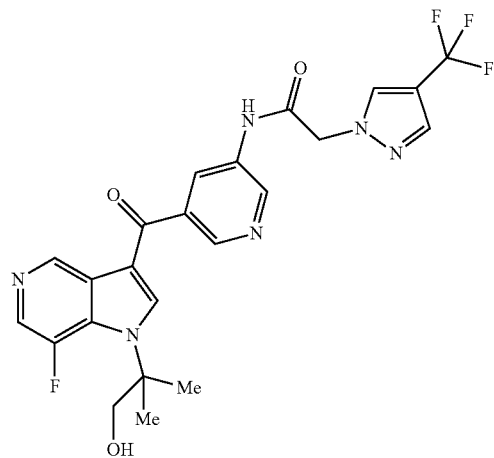 [SMILES: CC(C)(CO)n1cc(C(=O)c2cncc(NC(=O)Cn3cc(C(F)(F)F)cn3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-trifluoromethyl-pyrazol-1-yl)-acetamide (Preparation 4, 35 mg, 56 μmol) in THF (2 mL) 4M dioxane-HCl (0.5 mL) was added and stirred at room temperature for 18 hours. The reaction was evaporated in vacuo and triturated with pentane-ether to afford the title compound as an off white solid in 100% yield, 28.54 mg.

$^1$H NMR (400 MHz, DMSO-d$_6$): δ ppm 1.61 (s, 6H), 3.81 (s, 2H), 5.19 (s, 2H), 7.91 (s, 1H), 8.25 (s, 1H), 8.42 (d, 2H), 8.62 (d, 1H), 8.75 (s, 1H), 8.97 (s, 1H), 9.41 (s, 1H), 11.01 (s, 1H).

LCMS: R$_t$=2.87 minutes; m/z 505 [M+H]$^+$

Example 5

N-{5-[7-Fluoro-1-(2-hydroxy-1,1-dimethyl-ethyl)-1H-pyrrolo[3,2-c]pyridine-3-carbonyl]-pyridin-3-yl}-2-(3-trifluoromethyl-phenyl)-acetamide

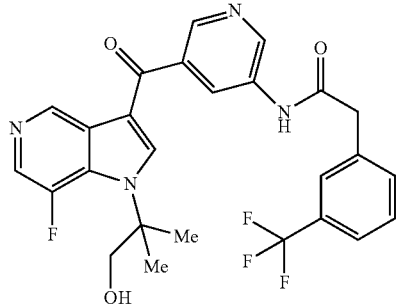 [SMILES: CC(C)(CO)n1cc(C(=O)c2cncc(NC(=O)Cc3cccc(C(F)(F)F)c3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(3-trifluoromethyl-phenyl)-acetamide (Preparation 3, 40 mg, 63 μmol) in THF (5 mL) 4M dioxane-HCl (0.5 mL) was added and stirred at room temperature for 2 hours. The reaction was evaporated in vacuo and triturated with pentane-ether to afford the title compound as a yellow solid in 86% yield, 28 mg.

$^1$H NMR (400 MHz, DMSO-d$_6$): δ ppm 1.65 (s, 6H), 3.84 (s, 2H), 3.90 (s, 2H), 7.58 (t, 1H), 7.63 (d, 2H), 8.30 (s, 1H), 8.59 (s, 1H), 8.67 (d, 1H), 8.75 (s, 1H), 9.00 (d, 1H), 9.45 (s, 1H), 10.89 (s, 1H).

LCMS: R$_t$=3.03 minutes; m/z 515 [M+H]$^+$

Example 6

2-(4-Chloro-phenyl)-N-{5-[7-fluoro-1-(2-hydroxy-1,1-dimethyl-ethyl)-1H-pyrrolo[3,2-c]pyridine-3-carbonyl]-pyridin-3-yl}-acetamide

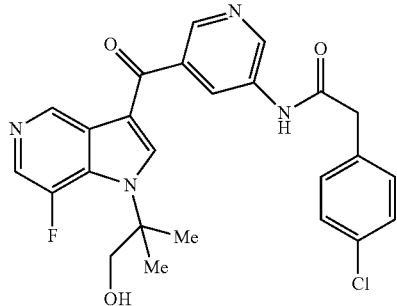 [SMILES: CC(C)(CO)n1cc(C(=O)c2cncc(NC(=O)Cc3ccc(Cl)cc3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-chloro-phenyl)-acetamide (Preparation 2, 35 mg, 70 μmol) in THF (2 mL) 4M dioxane-HCl (0.2 mL) was added and stirred at room temperature for 4 hours. The reaction was evaporated in vacuo and triturated with pentane-ether to afford the title compound as a white solid in 88% yield, 25 mg.

$^1$H NMR (400 MHz, DMSO-d$_6$): δ ppm 1.64 (s, 6H), 3.75 (s, 2H), 3.83 (s, 2H), 7.39 (s, 4H), 8.22 (s, 1H), 8.56 (m, 1H), 8.72 (s, 1H), 8.96 (s, 1H), 9.41 (s, 1H), 10.73 (s, 1H).

LCMS: R$_t$=2.87 minutes; m/z 480 [M+H]+

Example 7

N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-phenyl)-acetamide

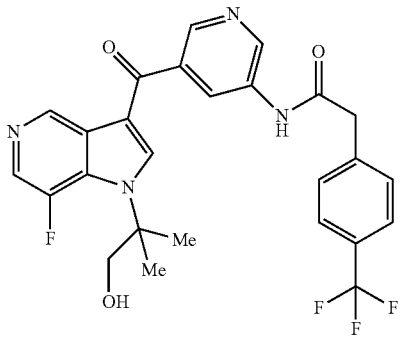 [SMILES: CC(C)(CO)n1cc(C(=O)c2cncc(NC(=O)Cc3ccc(C(F)(F)F)cc3)c2)c2cncc(F)c21]

To a solution of N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-trifluoromethyl-phenyl)-acetamide (Preparation 1, 45 mg, 49 μmol) in THF (5 mL) 4M dioxane-HCl (0.5 mL) was added and stirred at room temperature for 2 hours. The reaction was evaporated in vacuo and triturated with pentane-ether to afford the title compound as a yellow solid in 83% yield, 30 mg.

$^1$H NMR (400 MHz, DMSO-d$_6$): δ ppm 1.65 (s, 6H), 3.84 (s, 2H), 3.88 (s, 2H), 7.58 (d, 2H), 7.70 (d, 2H), 8.29 (s, 1H), 8.54 (s, 1H), 8.68 (m, 1H), 8.75 (d, 1H), 9.01 (s, 1H), 9.45 (s, 1H), 10.90 (s, 1H).

LCMS: R$_t$=3.06 minutes; m/z 515 [M+H]$^+$

Example 8

2-(5-Chloro-pyridin-2-yl)-N-{5-[1-(2-hydroxy-1,1-dimethyl-ethyl)-1H-pyrrolo[3,2-c]pyridine-3-carbonyl]-pyridin-3-yl}-acetamide

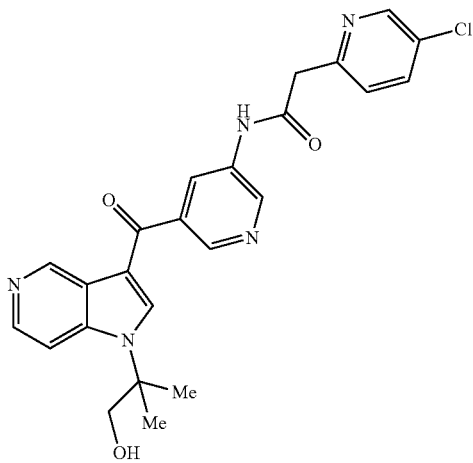 [SMILES: CC(C)(CO)n1cc(C(=O)c2cncc(NC(=O)Cc3ccc(Cl)cn3)c2)c2cnccc21]

To a solution of N-(5-{1-[2-(tert-Butyl-dimethyl-silanyloxy)-1,1-dimethyl-ethyl]-1H-pyrrolo[3,2-c]pyridine-3-carbonyl}-pyridin-3-yl)-2-(5-chloro-pyridin-2-yl)-acetamide (Preparation 8, 45 mg, 0.077 mmol) in THF (3 mL), 4M dioxane-HCl (0.4 mL) was added and stirred at room temperature for 18 hours. The reaction was evaporated in vacuo and purified by column chromatography on silica gel (gradient of MeOH: DCM 0:100 to 3:100) to afford the title compound as a yellow solid in 69% yield, 25 mg.

$^1$H NMR (400 MHz, DMSO-$d_6$): δ ppm 1.65 (s, 2H), 3.82 (d, 2H), 3.95 (s, 2H), 5.20 (m, 1H), 7.48 (d, 1H), 7.88-7.93 (m, 2H), 8.04 (s, 1H), 8.34 (d, 1H), 8.45 (m, 1H), 8.56 (d, 1H), 8.68 (d, 1H), 8.94 (d, 1H), 9.45 (s, 1H), 10.73 (s, 1H).

LCMS: $R_t$=2.56 minutes; m/z 464 [M+H]$^+$

Example 9

2-(4-cyanophenyl)-N-(2-{[1-(1-hydroxy-2-methylpropan-2-yl)-1H-pyrrolo[3,2-c]pyridin-3-yl]carbonyl}pyridin-4-yl)acetamide Prepared according to the method described for Example 8 using N-(2-{[1-(2-{[tert-butyl (dimethyl)silyl]oxy}-1,1-dimethylethyl)-1H-pyrrolo[3,2-c]pyridin-3-yl]carbonyl}pyridin-4-yl)-2-(4-cyanophenyl)acetamide (Preparation 9). Purified using preparative HPLC. LCMS (5 minute run) Rt=2.87 minutes MS m/z 454 [M+H]$^+$ Example 10

N-(2-{[1-(1-hydroxy-2-methylpropan-2-yl)-1H-pyrrolo[3,2-c]pyridin-3-yl]carbonyl}pyridin-4-yl)-2-[3-(trifluoromethyl)-1H-pyrazol-1-yl]acetamide Prepared according to the method described for Example 8 using N-(2-{[1-(2-{[tert-butyl (dimethyl)silyl]oxy}-1,1-dimethylethyl)-1H-pyrrolo[3,2-c]pyridin-3-yl]carbonyl}pyridin-4-yl)-2-[3-(trifluoromethyl)-1H-pyrazol-1-yl]acetamide (Preparation 10). Purified using preparative HPLC.

LCMS (5 minute run) Rt=2.83 minutes MS m/z 487 [M+H]$^+$

Example 11

N-(2-{[1-(1-hydroxy-2-methylpropan-2-yl)-1H-pyrrolo[3,2-c]pyridin-3-yl]carbonyl}pyridin-4-yl)-2-[4-(trifluoromethyl)-1H-1,2,3-triazol-1-yl]acetamide Prepared according to the method described for Example 8 using N-(2-{[1-(2-{[tert-butyl(dimethyl)silyl]oxy}-1,1-dimethylethyl)-1H-pyrrolo[3,2-c]pyridin-3-yl]carbonyl}pyridin-4-yl)-2-[4-(trifluoromethyl)-1H-1,2,3-triazol-1-yl]acetamide (Preparation 11). Purified using preparative HPLC.

LCMS (5 minute run) Rt=2.79 minutes MS m/z 488 [M−H]$^+$

Example 12

2-(4-cyanophenyl)-N-(5-{[1-(1-hydroxy-2-methylpropan-2-yl)-1H-pyrrolo[3,2-c]pyridin-3-yl]carbonyl}pyridin-3-yl)acetamide Prepared according to Method Y using N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-cyanophenyl)acetamide (Preparation 12).

LCMS (5 minute run) Rt=2.62 minutes MS m/z 454 [M−H]$^+$

Example 13

N-(5-{[1-(1-hydroxy-2-methylpropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide Prepared according to Method Y using N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-[4-(trifluoromethyl)-1H-1,2,3-triazol-1-yl]acetamide (Preparation 13).

LCMS (5 minute run) Rt=2.74 minutes MS m/z 488 [M+H]$^+$

Example 14

N-(5-{[1-(1-hydroxy-2-methylpropan-2-yl)-1H-pyrrolo[3,2-c]pyridin-3-yl]carbonyl}pyridin-3-yl)-2-[4-(propan-2-yl)-1H-1,2,3-triazol-1-yl]acetamide Prepared according to Method Y using N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-isopropyl-1H-1,2,3-triazol-1-yl)acetamide (Preparation 14).

LCMS (5 minute run) Rt=2.52 minutes MS m/z 462 [M+H]+

Example 15

2-(4-cyclopropyl-1H-1,2,3-triazol-1-yl)-N-(5-{[1-(1-hydroxy-2-methylpropan-2-yl)-1H-pyrrolo[3,2-c]pyridin-3-yl]carbonyl}pyridin-3-yl)acetamide Prepared according to Method Y using N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-cyclopropyl-1H-1,2,3-triazol-1-yl)acetamide (Preparation 15).

LCMS (5 minute run) Rt=2.49 minutes MS m/z 460 [M−H]$^+$

Example 16

2-(5-fluoropyridin-2-yl)-N-(5-{[1-(1-hydroxy-2-methylpropan-2-yl)-1H-pyrrolo[3,2-c]pyridin-3-yl]carbonyl}pyridin-3-yl)acetamide Prepared according to Method Y using N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(5-fluoropyridin-2-yl)acetamide (Preparation 16).

LCMS (5 minute run) Rt=2.52 minutes MS m/z 448 [M+H]$^+$

Example 17

Enantiomer 2

2-(5-chloropyridin-2-yl)-N-(2-{[1-(1-hydroxypropan-2-yl)-1H-pyrrolo[3,2-c]pyridin-3-yl]carbonyl}pyridin-4-yl)acetamide Prepared according to Method Y using N-(2-{[1-(2-{[tert-butyl(dimethyl)silyl]oxy}-1-methylethyl)-1H-pyrrolo[3,2-c]pyridin-3-yl]carbonyl}pyridin-4-yl)-2-(5-chloropyridin-2-yl)acetamide (Preparation 17).

LCMS (5 minute run) Rt=2.76 minutes MS m/z 450 [M+H]$^+$

Example 18

Enantiomer 1

2-(3-trifluoromethylphenyl)-N-(2-{[1-(1-hydroxypropan-2-yl)-1H-pyrrolo[3,2-c]pyridin-3-yl]carbonyl}pyridin-4-yl)acetamide Prepared according to Method Y using N-(2-{1-(2-{[tert-butyl(dimethyl)silyl]oxy}-1-methylethyl)-1H-pyrrolo[3,2-c]pyridin-3-yl]carbonyl}pyridin-4-yl)-2-[3-(trifluoromethyl)phenyl]acetamide (Preparation 18).

LCMS (5 minute run) Rt=3.01 minutes MS m/z 483 [M+H]$^+$

Example 19

2-(2-cyclopropyl-5-methyl-1,3-oxazol-4-yl)-N-(5-{[1-(propan-2-yl)-1H-pyrrolo[3,2-c]pyridin-3-yl]carbonyl}pyridin-3-yl)acetamide Method 1

To a mixture of (5-aminopyridin-3-yl)(1-isopropyl-1H-pyrrolo[3,2-c]pyridin-3-yl)methanone (Preparation 19, 80 mg, 0.285 mmol) and (2-cyclopropyl-5-methyl-1,3-oxazol-4-yl)acetic acid (Preparation 87, 52 mg, 0.285 mmol) in THF (5 mL) was added triethylamine (138 uL, 0.997 mmol) and propylphosphonic anhydride (429 uL, 0.712 mmol). The reaction was stirred at room temperature for 18 hours. The reaction was concentrated to dryness and purified using preparative HPLC to afford the title compound as a white solid (50 mg, 39%).

LCMS (5 minute run) Rt=1.98 minutes MS m/z 444 [M+H]$^+$

The following examples were prepared according to Method 1 using the appropriate amine and acid as referred to. Where necessary the crude reaction was also partitioned between EtOAc and saturated aqueous NaHCO$_3$ solution, the organic layer collected, washed with brine and dried over sodium sulphate before concentrating in vacuo and purifying by preparative HPLC.

| Example No. | Name | Data |
| --- | --- | --- |
| 20 | 2-(2,5-dicyclopropyl-1,3-oxazol-4-yl)-N-(5-{[1-(propan-2-yl)-1H-pyrrolo[3,2-c]pyridin-3-yl]carbonyl}pyridin-3-yl)acetamide | MS m/z 470 [M + H]$^+$ |
| 21 | N-(5-{[1-(propan-2-yl)-1H-pyrrolo[3,2-c]pyridin-3-yl]carbonyl}pyridin-3-yl)-2-[3-(trifluoromethyl)-1H-pyrazol-1-yl]acetamide | MS m/z 457 [M + H]$^+$ |
| 22 | 2-(5-chloropyridin-2-yl)-N-(5-{[1-(propan-2-yl)-1H-pyrrolo[3,2-c]pyridin-3-yl]carbonyl}pyridin-3-yl)acetamide | MS m/z 434 [M + H]$^+$ |
| 23 | 2-(5-fluoropyridin-2-yl)-N-(5-{[1-(propan-2-yl)-1H-pyrrolo[3,2-c]pyridin-3-yl]carbonyl}pyridin-3-yl)acetamide | MS m/z 418 [M + H]$^+$ |
| 24 | 2-(5-cyclopropyl-2-methyl-1,3-oxazol-4-yl)-N-(5-{[1-(propan-2-yl)-1H-pyrrolo[3,2-c]pyridin-3-yl]carbonyl}pyridin-3-yl)acetamide | MS m/z 444 [M + H]$^+$ |
| 25 | 2-(4-methyl-1H-pyrazol-1-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 26 | 2-(3-cyclopropyl-1H-pyrazol-1-yl)-N-(5-{[1-(propan-2-yl)-1H-pyrrolo[3,2-c]pyridin-3-yl]carbonyl}pyridin-3-yl)acetamide | MS m/z 429 [M + H]$^+$ |
| 27 | N-(2-{[1-(propan-2-yl)-1H-pyrrolo[3,2-c]pyridin-3-yl]carbonyl}pyridin-4-yl)-2[3-(trifluoromethyl)-1H-pyrazol-1-yl]acetamide | MS m/z 457 [M + H]$^+$ |
| 28 | 2-[5-methyl-3-(trifluoromethyl)-1H-pyrazol-1-yl]-N-(2-{[1-(propan-2-yl)-1H-pyrrolo[3,2-c]pyridin-3-yl]carbonyl}pyridin-4-yl)acetamide | MS m/z 471 [M + H]$^+$ |
| 29 | 2-(3-cyclopropyl-1H-pyrazol-1-yl)-N-(2-{[1-(propan-2-yl)-1H-pyrrolo[3,2-c]pyridin-3-yl]carbonyl}pyridin-4-yl)acetamide | MS m/z 429 [M + H]$^+$ |
| 30 | N-(2-{[1-(propan-2-yl)-1H-pyrrolo[3,2-c]pyridin-3-yl]carbonyl}pyridin-4-yl)-2[4-(trifluoromethyl)-1H-pyrazol-1-yl]acetamide | MS m/z 457 [M + H]$^+$ |
| 31 | N-(5-{[7-fluoro-1-(propan-2-yl)-1H-pyrrolo[3,2-c]pyridin-3-yl]carbonyl}pyridin-3-yl)-2[4-(trifluoromethyl)-1H-pyrazol-1-yl]acetamide | MS m/z 475 [M + H]$^+$ |
| 32 | N-(5-{[7-fluoro-1-(propan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide | MS m/z 489 [M + H]$^+$ |
| 33 | N-(5-{[1-(1-hydroxy-2-methylpropan-2-yl)-1H-pyrrolo[3,2-c]pyridin-3-yl]carbonyl}pyridin-3-yl)-2-[4-(trifluoromethyl)phenyl]acetamide | MS m/z 497 [M + H]$^+$ |
| 34 | N-(5-{[1-(1-hydroxypropan-2-yl)-1H-pyrrolo[3,2-c]pyridin-3-yl]carbonyl}pyridin-3-yl)-2-[3-(trifluoromethyl)phenyl]acetamide Enantiomer 1 | MS m/z 483 [M + H]$^+$ |
| 35 | N-(5-{[1-(1-hydroxypropan-2-yl)-1H-pyrrolo[3,2-c]pyridin-3-yl]carbonyl}pyridin-3-yl)-2-[4-(trifluoromethyl)phenyl]acetamide Enantiomer 2 | MS m/z 483 [M + H]$^+$ |
| 36 | N-(5-{[1-(1-hydroxypropan-2-yl)-1H-pyrrolo[3,2-c]pyridin-3-yl]carbonyl}pyridin-3-yl)-2-[3-(trifluoromethyl)phenyl]acetamide Enantiomer 2 | MS m/z 483 [M + H]$^+$ |
| 37 | 2-[4-cyano-3-(trifluoromethyl)phenyl]-N-(5-{[1-(propan-2-yl)-1H-pyrrolo[3,2-c]pyridin-3-yl]carbonyl}pyridin-3-yl)acetamide | MS m/z 492 [M + H]$^+$ |

-continued

| Example No. | Name | Data |
|---|---|---|
| 38 | N-(5-{[1-(propan-2-yl)-1H-pyrrolo[3,2-c]pyridin-3-yl]carbonyl}pyridin-3-yl)-2[4-(trifluoromethyl)-1H-1,2,3-triazol-1-yl]acetamide | MS m/z 458 [M + H]$^+$ |
| 39 | 2-[5-cyclopropyl-2-(methoxymethyl)-1,3-oxazol-4-yl]-N-(5-{[1-(propan-2-yl)-1H-pyrrolo[3,2-c]pyridin-3-yl]carbonyl}pyridin-3-yl)acetamide | MS m/z 474 [M + H]$^+$ |
| 40 | 2-(4-methyl-1,2,5-oxadiazol-3-yl)-N-(5-{[1-(propan-2-yl)-1H-pyrrolo[3,2-c]pyridin-3-yl]carbonyl}pyridin-3-yl)acetamide | MS m/z 405 [M + H]$^+$ |
| 41 | 2-(1-methyl-1H-imidazol-4-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 42 | 2-(3-tert-butyl-1-methyl-1H-1,2,4-triazol-5-yl)-N-(5-{[1-(propan-2-yl)-1H-pyrrolo[3,2-c]pyridin-3-yl]carbonyl}pyridin-3-yl)acetamide | MS m/z 460 [M + H]$^+$ |
| 43 | 2-(2-cyclopropyl-1,3-oxazol-4-yl)-N-(5-{[1-(propan-2-yl)-1H-pyrrolo[3,2-c]pyridin-3-yl]carbonyl}pyridin-3-yl)acetamide | MS m/z 430 [M + H]$^+$ |
| 44 | 2-[3-tert-butyl-1-(2-methoxyethyl)-1H-1,2,4-triazol-5-yl]-N-(5-{[1-(propan-2-yl)-1H-pyrrolo[3,2-c]pyridin-3-yl]carbonyl}pyridin-3-yl)acetamide | MS m/z 504 [M + H]$^+$ |
| 45 | 2-(1-methyl-1H-imidazol-5-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 46 | 2-(1-methyl-1H-imidazol-2-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 47 | 2-(4-cyanophenyl)-N-(2-methoxy-5-{[1-(propan-2-yl)-1H-pyrrolo[3,2-c]pyridin-3-yl]carbonyl}pyridin-3-yl)acetamide | MS m/z 454 [M + H]$^+$ |
| 48 | N-(2-methoxy-5-{[1-(propan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide | $^1$HNMR (400 MHz, DMSO-d$_6$): δ ppm 1.50 (d, 6H), 2.30 (s, 3H), 4.10 (s, 3H), 4.86-4.89 (m, 1H), 5.27 (s, 2H), 6.54 (s, 1H), 7.73 (d, 1H), 8.29 (s, 1H), 8.38 (d, 1H), 8.47 (d, 1H), 8.78 (d, 1H), 9.38 (s, 1H), 10.16 (s, 1H). |
| 49 | 2-(4-cyanophenyl)-N-(5-{[1-(propan-2-yl)-1H-pyrrolo[3,2-c]pyridin-3-yl]carbonyl}pyridin-3-yl)acetamide | MS m/z 424 [M + H]$^+$ |
| 50 | N-(5-{[1-(propan-2-yl)-1H-pyrrolo[3,2-c]pyridin-3-yl]carbonyl}pyridin-3-yl)-2-[1-(propan-2-yl)-3-(trifluoromethyl)-1H-pyrazol-4-yl]acetamide | MS m/z 499 [M + H]$^+$ |
| 51 | 2-(4-cyclopropyl-1H-1,2,3-triazol-1-yl)-N-(5-{[1-(propan-2-yl)-1H-pyrrolo[3,2-c]pyridin-3-yl]carbonyl}pyridin-3-yl)acetamide | MS m/z 430 [M + H]$^+$ |
| 52 | 2-(4-cyclopropyl-1H-1,2,3-triazol-1-yl)-N-(2-{[1-(propan-2-yl)-1H-pyrrolo[3,2-c]pyridin-3-yl]carbonyl}pyridin-4-yl)acetamide | MS m/z 430 [M + H]$^+$ |
| 53 | N-(2-{[1-(propan-2-yl)-1H-pyrrolo[3,2-c]pyridin-3-yl]carbonyl}pyridin-4-yl)-2-[4-(trifluoromethyl)-1H-1,2,3-triazol-1-yl]acetamide | MS m/z 458 [M + H]$^+$ |
| 54 | 2-(4-cyanophenyl)-N-(2-{[1-(propan-2-yl)-1H-pyrrolo[3,2-c]pyridin-3-yl]carbonyl}pyridin-4-yl)acetamide | MS m/z 424 [M + H]$^+$ |
| 55 | 2-(5-chloropyridin-2-yl)-N-(2-{[1-(propan-2-yl)-1H-pyrrolo[3,2-c]pyridin-3-yl]carbonyl}pyridin-4-yl)acetamide | MS m/z 434 [M + H]$^+$ |
| 56 | 2-[1-cyclopropyl-5-(trifluoromethyl)-1H-pyrazol-4-yl]-N-(2-{[1-(propan-2-yl)-1H-pyrrolo[3,2-c]pyridin-3-yl]carbonyl}pyridin-4-yl)acetamide | MS m/z 497 [M + H]$^+$ |
| 57 | 2-[1-cyclopropyl-3-(trifluoromethyl)-1H-pyrazol-4-yl]-N-(2-{[{1-(propan-2-yl)-1H-pyrrolo[3,2-c]pyridin-3-yl]carbonyl}pyridin-4-yl)acetamide | MS m/z 497 [M + H]$^+$ |
| 58 | 2-(1,3-dimethyl-1H-pyrazol-4-yl)-N-(2-{[1-(propan-2-yl)-1H-pyrrolo[3,2-c]pyridin-3-yl]carbonyl}pyridin-4-yl)acetamide | MS m/z 417 [M + H]$^+$ |
| 59 | N-(5-{[1-(1-hydroxypropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide Enantiomer 1 | MS m/z 474 [M + H]$^+$ |
| 60 | N-(5-{[1-(1-hydroxypropan-2-yl)-1H-pyrrolo[3,2-c]pyridin-3-yl]carbonyl}pyridin-3-yl)-2-[3-(trifluoromethyl)-1H-pyrazol-1-yl]acetamide Enantiomer 1 | MS m/z 473 [M + H]$^+$ |
| 61 | 2-(4-cyclopropyl-1H-1,2,3-triazol-1-yl)-N-(5-{[1-(1-hydroxypropan-2-yl)-1H-pyrrolo[3,2-c]pyridin-3- | MS m/z 446 [M + H]$^+$ |

-continued

| Example No. | Name | Data |
|---|---|---|
| | yl]carbonyl}pyridin-3-yl)acetamide Enantiomer 1 | |
| 62 | N-(5-{[1-(1-hydroxypropan-2-yl)-1H-pyrrolo[3,2-c]pyridin-3-yl]carbonyl}pyridin-3-yl)-2-[4-(propan-2-yl)-1H-1,2,3-triazol-1-yl]acetamide Enantiomer 1 | MS m/z 448 [M + H]+ |
| 63 | N-(5-{[1-(1-hydroxypropan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide Enantiomer 1 | MS m/z 487 [M + H]+ |
| 64 | N-(5-{[1-(1-hydroxypropan-2-yl)-1H-pyrrolo[3,2-c]pyridin-3-yl]carbonyl}pyridin-3-yl)-2-[1-(propan-2-yl)-5-(trifluoromethyl)-1H-pyrazol-4-yl]acetamide Enantiomer 1 | MS m/z 515 [M + H]+ |
| 65 | N-(5-{[1-(1-hydroxypropan-2-yl)-1H-pyrrolo[3,2-c]pyridin-3-yl]carbonyl}pyridin-3-yl)-2-[4-(trifluoromethyl)phenyl]acetamide Enantiomer 1 | MS m/z 483 [M + H]+ |
| 66 | 2-(5-chloropyridin-2-yl)-N-(5-{[1-(1-hydroxypropan-2-yl)-1H-pyrrolo[3,2-c]pyridin-3-yl]carbonyl}pyridin-3-yl)acetamide Enantiomer 1 | MS m/z 450 [M + H]+ |
| 67 | 2-(4-cyanophenyl)-N-(5-{1-(1-hydroxypropan-2-yl)-1H-pyrrolo[3,2-c]pyridin-3-yl]carbonyl}pyridin-3-yl)acetamide Enantiomer 1 | MS m/z 440 [M + H]+ |
| 68 | 2-(5-fluoropyridin-2-yl)-N-(5-{[1-(1-hydroxypropan-2-yl)-1H-pyrrolo[3,2-c]pyridin-3-yl]carbonyl}pyridin-3-yl)acetamide Enantiomer 1 | MS m/z 434 [M + H]+ |
| 69 | N-(5-{[1-(1-hydroxypropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide Enantiomer 2 | MS m/z 474 [M + H]+ |
| 70 | N-(5-{[1-(1-hydroxypropan-2-yl)-1H-pyrrolo[3,2-c]pyridin-3-yl]carbonyl}pyridin-3-yl)-2-[4-(propan-2-yl)-1H-1,2,3-triazol-1-yl]acetamide Enantiomer 2 | MS m/z 448 [M + H]+ |
| 71 | N-(5-{[1-(1-hydroxypropan-2-yl)-1H-pyrrolo[3,2-c]pyridin-3-yl]carbonyl}pyridin-3-yl)-2-[1-(propan-2-yl)-5-(trifluoromethyl)-1H-pyrazol-4-yl]acetamide Enantiomer 2 | MS m/z 515 [M + H]+ |
| 72 | 2-(4-cyanophenyl)-N-(5-{[1-(1-hydroxypropan-2-yl)-1H-pyrrolo[3,2-c]pyridin-3-yl]carbonyl}pyridin-3-yl)acetamide Enantiomer 2 | MS m/z 440 [M + H]+ |
| 73 | 2-(5-chloropyridin-2-yl)-N-(5-{[1-(1-hydroxypropan-2-yl)-1H-pyrrolo[3,2-c]pyridin-3-yl]carbonyl}pyridin-3-yl)acetamide Enantiomer 2 | MS m/z 450 [M + H]+ |
| 74 | 2-(5-fluoropyridin-2-yl)-N-(5-{[1-(1-hydroxypropan-2-yl)-1H-pyrrolo[3,2-c]pyridin-3-yl]carbonyl}pyridin-3-yl)acetamide Enantiomer 2 | MS m/z 434 [M + H]+ |
| 75 | N-(5-{[1-(1-hydroxypropan-2-yl)-1H-pyrrolo[3,2-c]pyridin-3-yl]carbonyl}pyridin-3-yl)-2-[3-(trifluoromethyl)-1H-pyrazol-1-yl]acetamide Enantiomer 2 | MS m/z 473 [M + H]+ |
| 76 | 2-(4-cyclopropyl-1H-1,2,3-triazol-1-yl)-N-(5-{[1-(1-hydroxypropan-2-yl)-1H-pyrrolo[3,2-c]pyridin-3-yl]carbonyl}pyridin-3-yl)acetamide Enantiomer 2 | MS m/z 446 [M + H]+ |
| 77 | N-(5-{[1-(1-hydroxypropan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide Enantiomer 2 | MS m/z 487 [M + H]+ |
| 78 | 2-(2-cyclopropyl-5-methyl-1,3-oxazol-4-yl)-N-(4-{[1-(propan-2-yl)-1H-pyrrolo[3,2-c]pyridin-3-yl]carbonyl}pyridin-2-yl)acetamide | MS m/z 444 [M + H]+ |
| 79 | 2-(2,5-dicyclopropyl-1,3-oxazol-4-yl)-N-(4-{[1-(propan-2-yl)-1H-pyrrolo[3,2-c]pyridin-3-yl]carbonyl}pyridin-2-yl)acetamide | MS m/z 470 [M + H]+ |
| 80 | 2-[5-cyclopropyl-2-(methoxymethyl)-1,3-oxazol-4-yl]-N-(4-{[1-(propan-2-yl)-1H-pyrrolo[3,2-c]pyridin-3-yl]carbonyl}pyridin-2-yl)acetamide | MS m/z 474[M + H]+ |
| 81 | 2-(5-fluoropyridin-2-yl)-N-(4-{[1-(propan-2-yl)-1H-pyrrolo[3,2-c]pyridin-3-yl]carbonyl}pyridin-2-yl)acetamide | MS m/z 418 [M + H]+ |
| 82 | 2-(5-chloropyridin-2-yl)-N-(4-{[1-(propan-2-yl)-1H-pyrrolo[3,2-c]pyridin-3-yl]carbonyl}pyridin-2-yl)acetamide | MS m/z 434 [M + H]+ |
| 83 | N-(2-{[7-fluoro-1-(propan-2-yl)-1H-pyrrolo[3,2-c]pyridin-3-yl]carbonyl}pyridin-4-yl)-2-[4-(trifluoromethyl)-1H-1,2,3-triazol-1-yl]acetamide | MS m/z 476 [M + H]+ |
| 84 | N-(2-{[1-(1-hydroxypropan-2-yl)-1H-pyrrolo[3,2-c]pyridin-3-yl]carbonyl}pyridin-4-yl)-2-[4- | MS m/z 451 [M + H]+ |

-continued

| Example No. | Name | Data |
|---|---|---|
| | (trifluoromethyl)phenyl]acetamide Enantiomer 1 | |
| 85 | 2-(4-chlorophenyl)-N-(2-{[7-fluoro-1-(propan-2-yl)-1H-pyrrolo[3,2-c]pyridin-3-yl]carbonyl}pyridin-4-yl)acetamide | MS m/z 451 [M + H]+ |
| 86 | 2-(5-chloropyridin-2-yl)-N-(2-{[1-(1-hydroxypropan-2-yl)-1H-pyrrolo[3,2-c]pyridin-3-yl]carbonyl}pyridin-4-yl)acetamide Enantiomer 1 | MS m/z 450 [M + H]+ |
| 87 | N-(5-{[7-fluoro-1-(propan-2-yl)-1H-pyrrolo[3,2-c]pyridin-3-yl]carbonyl}pyridin-3-yl)-2-[4-(trifluoromethyl)-1H-1,2,3-triazol-1-yl]acetamide | MS m/z 476 [M + H]+ |
| 88 | N-(5-{[7-fluoro-1-(propan-2-yl)-1H-pyrrolo[3,2-c]pyridin-3-yl]carbonyl}pyridin-3-yl)-2-(5-fluoropyridin-2-yl)acetamide | MS m/z 436 [M + H]+ |
| 89 | 2-(4-cyclopropyl-1H-1,2,3-triazol-1-yl)-N-(5-{[7-fluoro-1-(propan-2-yl)-1H-pyrrolo[3,2-c]pyridin-3-yl]carbonyl}pyridin-3-yl)acetamide | MS m/z 448 [M + H]+ |
| 90 | 2-(3-cyclopropyl-1H-pyrazol-1-yl)-N-(5-{[7-fluoro-1-(propan-2-yl)-1H-pyrrolo[3,2-c]pyridin-3-yl]carbonyl}pyridin-3-yl)acetamide | MS m/z 447 [M + H]+ |
| 91 | 2-(4-cyclopropyl-1H-pyrazol-1-yl)-N-(5-{[7-fluoro-1-(propan-2-yl)-1H-pyrrolo[3,2-c]pyridin-3-yl]carbonyl}pyridin-3-yl)acetamide | MS m/z 447 [M + H]+ |

Example 92

2-(4-cyanophenyl)-N-(5-{[7-fluoro-1-(1-hydroxy-2-methylpropan-2-yl)-1H-pyrrolo[3,2-c]pyridin-3-yl]carbonyl}pyridin-3-yl)acetamide The title compound was prepared according to the method described for Preparation 1 using 4-cyanophenylacetic acid followed by the method described for Example 8 as an off white solid (26 mg, 90%).

LCMS (5 minute run) Rt=2.78 minutes MS m/z 472 [M+H]+

Example 93

N-(5-{[7-fluoro-1-(1-hydroxy-2-methylpropan-2-yl)-1H-pyrrolo[3,2-c]pyridin-3-yl]carbonyl}pyridin-3-yl)-2-(5-fluoropyridin-2-yl)acetamide The title compound was prepared according to the method described for Preparation 1 using (5-fluoropyridin-2-yl)acetic acid (Preparation 82) followed by the method described for Example 8 as a brown solid (30 mg, 100%).

LCMS (5 minute run) Rt=2.64 minutes MS m/z 466 [M+H]+

Example 94

N-(5-{[7-fluoro-1-(1-hydroxy-2-methylpropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide The title compound was prepared according to the method described for Preparation 1 using [4-(trifluoromethyl)-1H-1,2,3-triazol-1-yl]acetic acid (Preparation 90) followed by the method described for Example 8 as a brown solid (26 mg, 84%).

LCMS (5 minute run) Rt=2.83 minutes MS m/z 506 [M+H]+

Example 95

N-(5-{[7-fluoro-1-(1-hydroxy-2-methylpropan-2-yl)-1H-pyrrolo[3,2-c]pyridin-3-yl]carbonyl}pyridin-3-yl)-2-[3-(trifluoromethyl)-1H-pyrazol-1-yl]acetamide The title compound was prepared according to the method described for Preparation 1 using [3-(trifluoromethyl)-1H-pyrazol-1-yl]acetic acid (Preparation 74) followed by the method described for Example 8 as an off white solid (32 mg, 87%).

LCMS (5 minute run) Rt=2.98 minutes MS m/z 505 [M+H]+

Library Protocol 1

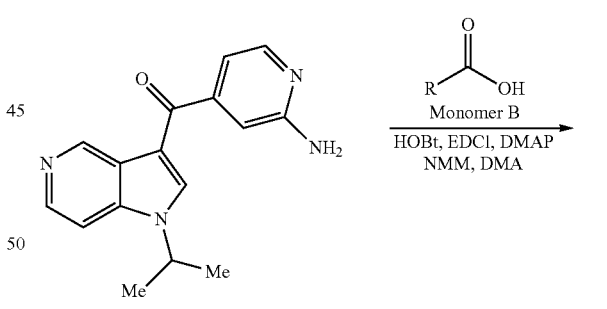

To Monomer B (90 µmol) was added a 0.13 M solution of Monomer A, (2-Aminopyridin-4-yl)-(1-isopropyl-1H-pyrrolo[3,2-c]pyridin-3-yl)methanone (Preparation 20, 500 uL, 65 umol) in DMA. NMM (16.8 μL, 150 μmol) was added followed by DMAP (6.5 μmol). A 0.375M solution of EDCI (400 μL, 150 μmol) in DMA and a 0.075M solution of HOBt (100 μL, 7.5 umol) in DMA was added and the reaction shaken at 60° C. for 4 hours. The solvent was removed in vacuo and the residue purified using preparative HPLC to afford the desired compounds.

Purification Method A:

Column: Welch XB-C18 2.1×50 mm 5 μm, 50° C., mobile phase A: 0.0375% TFA in water; mobile phase B: 0.01875% TFA in acetonitrile. Initial gradient 1% B; 0.60 mins 5% B, 4.00 mins 100% B, 4.30 mins 1% B, 4.70 mins 1% B. Flow rate 0.8 mL/min.

Purification Method B:

Column: Welch XB-C18 2.1×50 mm 5 μm, 50° C., mobile phase A: 0.0375% TFA in water; mobile phase B: 0.01875% TFA in acetonitrile. Initial gradient 10% B; 0.60 mins 10% B, 4.00 mins 100% B, 4.30 mins 10% B, 4.70 mins 10% B. Flow rate 0.8 mL/min.

Purification Method C:

Column Welch XB-C18 2.1×50 mm 5 μm, 50° C., mobile phase A: 0.05% NH4OH in water; mobile phase B: 100% acetonitrile. Initial gradient 5% B; 0.50 mins 5% B, 3.40 mins 100% B, 4.20 mins 100% B, 4.21 mins 5% B, 4.70 mins 5% B. Flow rate 0.8 mL/min.

The following Examples were prepared in library protocol 1:

Library Protocol 2

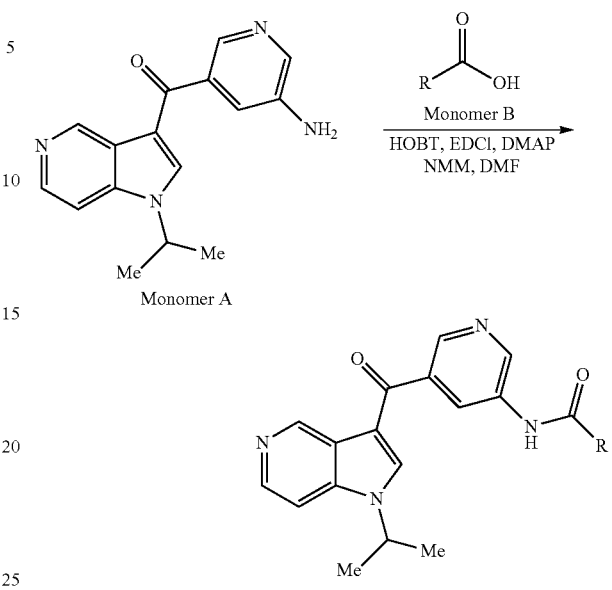

To a 0.375M solution of Monomer B (200 μL, 75 umol) in DMF was added a 0.375 M solution of Monomer A, 5-ami-

| Example | Name/Structure | Data |
|---|---|---|
| 96 | 2-(3-chlorophenyl)-N-(4-{[1-(propan-2-yl)-1H-pyrrolo[3,2-c]pyridin-3-yl]carbonyl}pyridin-2-yl)acetamide | MS m/z 433 [M + H]+ |
| 97 | 2-[3-(2-hydroxy-2-methylpropyl)phenyl]-N-(4-{[1-(propan-2-yl)-1H-pyrrolo[3,2-c]pyridin-3-yl]carbonyl}pyridin-2-yl)acetamide | MS m/z 471 [M + H]+ |
| 98 | N-(4-{[1-(propan-2-yl)-1H-pyrrolo[3,2-c]pyridin-3-yl]carbonyl}pyridin-2-yl)-2[4-(propan-2-yl)-1H-1,2,3-triazol-1-yl]acetamide | MS m/z 432 [M + H]+ |
| 99 | 2-(4-chloro-1H-pyrazol-1-yl)-N-(4-{[1-(propan-2-yl)-1H-pyrrolo[3,2-c]pyridin-3-yl]carbonyl}pyridin-2-yl)acetamide | MS m/z 423 [M+H]+ |
| 100 | 2-(2-chlorophenyl)-N-(5-{[1-(propan-2-yl)-1H-pyrrolo[3,2-c]pyridin-3-yl]carbonyl}pyridin-3-yl)acetamide | MS m/z 433 [M + H]+ |
| 101 | 2-(4-methoxyphenyl)-N-(4-{[1-(propan-2-yl)-1H-pyrrolo[3,2-c]pyridin-3-yl]carbonyl}pyridin-2-yl)acetamide | MS m/z 429 [M+H]+ |
| 102 | 2-(1H-imidazol-1-yl)-N-(4-{[1-(propan-2-yl)-1H-pyrrolo[3,2-c]pyridin-3-yl]carbonyl}pyridin-2-yl)acetamide | MS m/z 389 [M + H]+ |
| 103 | 2-(4-chlorophenyl)-N-(4-{[1-(propan-2-yl)-1H-pyrrolo[3,2-c]pyridin-3-yl]carbonyl}pyridin-2yl)acetamide | MS m/z 433 [M + H]+ |
| 104 | 2-[5-methyl-3-(trifluoromethyl)-1H-pyrazol-1-yl]-N-(4-{[1-(propan-2-yl)-1H-pyrrolo[3,2-c]pyridin-3-yl]carbonyl}pyridin-2-yl)acetamide | MS m/z 471 [M + H]+ |
| 105 | 2-(2-chlorophenyl)-N-(4-{[1-(propan-2-yl)-1H-pyrrolo[3,2-c]pyridin-3-yl]carbonyl}pyridin-2-yl)acetamide | MS m/z 433 [M + H]+ |
| 106 | 2-(2,4-difluorophenyl)-N-(4-{[1-(propan-2-yl)-1H-pyrrolo[3,2-c]pyridin-3-yl]carbonyl}pyridin-2-yl)acetamide | MS m/z 435 [M+H]+ |
| 107 | 2-phenyl-N-(4-{[1-(propan-2-yl)-1H-pyrrolo[3,2-c]pyridin-3-yl]carbonyl}pyridin-2-yl)acetamide | MS m/z 399 [M + H]+ |
| 108 | 2-(3-methoxyphenyl)-N-(4-{[1-(propan-2-yl)-1H-pyrrolo[3,2-c]pyridin-3-yl]carbonyl}pyridin-2-yl)acetamide | MS m/z 429 [M + H]+ |
| 109 | 2-(3-methyl-1H-pyrazol-1-yl)-N-(4-{[1-(propan-2-yl)-1H-pyrrolo[3,2-c]pyridin-3-yl]carbonyl}pyridin-2-yl)acetamide | MS m/z 403 [M + H]+ |
| 110 | N-(4-{[1-(propan-2-yl)-1H-pyrrolo[3,2-c]pyridin-3-yl]carbonyl}pyridin-2-yl)-2-(pyrazin-2-yl)acetamide | MS m/z 401 [M + H]+ |
| 111 | 2-[5-(propan-2-yl)-1H-pyrazol-1-yl]-N-(4-{[1-(propan-2-yl)-1H-pyrrolo[3,2-c]pyridin-3-yl]carbonyl}pyridin-2-yl)acetamide | MS m/z 431 [M + H]+ |
| 112 | 2-(3,5-dimethyl-1H-1,2,4-triazol-1-yl)-N-(4-{[1-(propan-2-yl)-1H-pyrrolo[3,2-c]pyridin-3-yl]carbonyl}pyridin-2-yl)acetamide | MS m/z 418 [M + H]+ |
| 113 | 2-[5-methyl-3-(propan-2-yl)-1H-pyrazol-1-yl]-N-(4-{[1-(propan-2-yl)-1H-pyrrolo[3,2-c]pyridin-3-yl]carbonyl}pyridin-2-yl)acetamide | MS m/z 445 [M + H]+ |
| 114 | 2-(4-methyl-1H-1,2,3-triazol-1-yl)-N-(4-{[1-(propan-2-yl)-1H-pyrrolo[3,2-c]pyridin-3-yl]carbonyl}pyridin-2-yl)acetamide | MS m/z 404 [M + H]+ | nopyridin-3-yl)(1-isopropyl-1H-pyrrolo[3,2-c]pyridin-3-yl) methanone (Preparation 19, 2.00 μL, 75 μmol) in DMF. NMM (15.2 mg, 150 μmol) was added followed by DMAP (15 μmol). A 0.5M solution of EDCI (300 μL, 150 μmol) in DMF and a 0.05M solution of HOBt (300 μL, 150 μmol) in DMF was added and the reaction shaken at 50° C. for 1.5 hours. The solvent was removed in vacuo and the residue purified using preparative HPLC to afford the desired compounds.

Purification Method A:
Column: Welch XB-C18 2.1×50 mm 5 μm, 50° C., mobile phase A: 0.0375% TFA in water; mobile phase B: 0.01875% TFA in acetonitrile. Initial gradient 1% B; 0.60 mins 5% B, 4.00 mins 100% B, 4.30 mins 1% B, 4.70 mins 1% B. Flow rate 0.8 mL/min.

Purification Method B:
Column: Welch XB-C18 2.1×50 mm 5 μm, 50° C., mobile phase A: 0.0375% TFA in water; mobile phase B: 0.01875% TFA in acetonitrile. Initial gradient 10% B; 0.60 mins 10% B, 4.00 mins 100% B, 4.30 mins 10% B, 4.70 mins 10% B. Flow rate 0.8 mL/min.

Purification Method C:
Column Welch XB-C18 2.1×50 mm 5 μm, 50° C., mobile phase A: 0.05% NH4OH in water; mobile phase B: 100% acetonitrile. Initial gradient 5% B; 0.50 mins 5% B, 3.40 mins 100% B, 4.20 mins 100% B, 4.21 mins 5% B, 4.70 mins 5% B. Flow rate 0.8 mL/min.

The following Examples were prepared in Library Protocol 2:

| Example | Name | Data |
|---|---|---|
| 115 | 2-(4-fluorophenyl)-N-(5-{[1-(propan-2-yl)-1H-pyrrolo[3,2-c]pyridin-3-yl]carbonyl}pyridin-3-yl)acetamide | MS m/z 417 [M + H]$^+$ |
| 116 | 2-(4-chlorophenyl)-N-(5-{[1-(propan-2-yl)-1H-pyrrolo[3,2-c]pyridin-3-yl]carbonyl}pyridin-3-yl)acetamide | MS m/z 433 [M + H]$^+$ |
| 117 | 2-(3-(2-hydroxy-2-methylpropyl)phenyl)-N-(5-{[1-(propan-2-yl)-1H-pyrrolo[3,2-c]pyridin-3-yl]carbonyl}pyridin-3-yl)acetamide | MS m/z 471 [M + H]$^+$ |
| 118 | 2-(2-methyl-1H-imidazol-1-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 119 | N-(5-{[1-(propan-2-yl)-1H-pyrrolo[3,2-c]pyridin-3-yl]carbonyl}pyridin-3-yl)-2-(pyrimidin-2-yl)acetamide | MS m/z 401 [M + H]$^+$ |
| 120 | 2-(5-methyl-3-(propan-2-yl)-1H-pyrazol-1-yl]-N-(5-{[1-(propan-2-yl)-1H-pyrrolo[3,2-c]pyridin-3-yl]carbonyl}pyridin-3-yl)acetamide | MS m/z 445 [M + H]$^+$ |
| 121 | 2-(5-methyl-3-(trifluoromethyl)-1H-pyrazol-1-yl]-N-(5-{[1-(propan-2-yl)-1H-pyrrolo[3,2-c]pyridin-3-yl]carbonyl}pyridin-3-yl)acetamide | MS m/z 471 [M + H]$^+$ |
| 122 | N-(5-{[1-(propan-2-yl)-1H-pyrrolo[3,2-c]pyridin-3-yl]carbonyl}pyridin-3-yl)-2(1H-pyrazol-1-yl)acetamide | MS m/z 389 [M + H]$^+$ |
| 123 | N-(5-{[1-(propan-2-yl)-1H-pyrrolo[3,2-c]pyridin-3-yl]carbonyl}pyridin-3-yl)-2-[4(propan-2-yl)-1H-1,2,3-triazol-1-yl]acetamide | MS m/z 432 [M + H]$^+$ |
| 124 | 2-(5-(propan-2-yl)-1H-pyrazol-1-yl]-N-(5-{[1-(propan-2-yl)-1H-pyrrolo[3,2-c]pyridin-3-yl]carbonyl}pyridin-3-yl)acetamide | MS m/z 431 [M + H]$^+$ |
| 125 | 2-(3-chlorophenyl)-N-(5-{[1-(propan-2-yl)-1H-pyrrolo[3,2-c]pyridin-3-yl]carbonyl}pyridin-3-yl)acetamide | MS m/z 433 [M + H]$^+$ |
| 126 | 2-(3-chlorophenyl)-N-(5-{[1-(propan-2-yl)-1H-pyrrolo[3,2-c]pyridin-3-yl]carbonyl}pyridin-3-yl)acetamide | MS m/z 431 [M + H]$^+$ |
| 127 | 2-(4-chloro-1H-pyrazol-1-yl]-N-(5-{[1-(propan-2-yl)-1H-pyrrolo[3,2-c]pyridin-3-yl]carbonyl}pyridin-3-yl)acetamide | MS m/z 423 [M + H]$^+$ |
| 128 | 2-(4-methoxyphenyl)-N-(5-{[1-(propan-2-yl)-1H-pyrrolo[3,2-c]pyridin-3-yl]carbonyl}pyridin-3-yl)acetamide | MS m/z 429 [M + H]$^+$ |
| 129 | 2-(3-methoxyphenyl)-N-(5-{[1-(propan-2-yl)-1H-pyrrolo[3,2-c]pyridin-3-yl]carbonyl}pyridin-3-yl)acetamide | MS m/z 433 [M + H]$^+$ |
| 130 | 2-phenyl-N-(5-{[1-(propan-2-yl)-1H-pyrrolo[3,2-c]pyridin-3-yl]carbonyl}pyridin-3-yl)acetamide | MS m/z 399 [M + H]$^+$ |
| 131 | 2-(3,5-dimethyl-1H-pyrazol-1-yl)-N-(5-{[1-(propan-2-yl)-1H-pyrrolo[3,2-c]pyridin-3-yl]carbonyl}pyridin-3-yl)acetamide | MS m/z 417 [M + H]$^+$ |
| 132 | 2-(4-methyl-1H-1,2,3-triazol-1-yl)-N-(5-{[1-(propan-2-yl)-1H-pyrrolo[3,2-c]pyridin-3-yl]carbonyl}pyridin-3-yl)acetamide | MS m/z 404 [M + H]$^+$ |
| 133 | N-(5-{[1-(propan-2-yl)-1H-pyrrolo[3,2-c]pyridin-3-yl]carbonyl}pyridin-3-yl)-2-(pyrazin-2-yl)acetamide | MS m/z 401 [M + H]$^+$ |
| 134 | 2-(3-methyl-1H-pyrazol-1-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 135 | 2-(5-methyl-1H-pyrazol-1-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 136 | 2(3-methyl-1H-pyrazol-5-yl)-N-(5-{[1-(propan-2-yl)-1H-pyrrolo[3,2-c]pyridin-3-yl]carbonyl}pyridin-3-yl)acetamide | MS m/z 403 [M + H]$^+$ |
| 137 | 2-(3,5-dimethyl-1H-1,2,4-triazol-1-yl)-N-(5-{[1-(propan-2-yl)-1H-pyrrolo[3,2-c]pyridin-3-yl]carbonyl} pyridin-3-yl)acetamide | MS m/z 418 [M + H]$^+$ |

Example 138

2(5-cyanopyridin-2-yl)-N-(4-{[1-(propan-2-yl)-1H-pyrrolo[3,2-c]pyridin-3-yl]carbonyl}pyridin-2-yl) acetamide Method 3

A mixture of 2-(5-bromopyridin-2-yl)-N-(4-{[1-(propan-2-yl)-1H-pyrrolo[3,2-c]pyridin-3-yl]carbonyl}pyridin-2-yl)acetamide (Example 237, 40 mg, 0.083 mmol), zinc cyanide (29 mg, 0.251 mmol), Pd$_2$(dba)$_3$ (3 mg, 0.003 mmol) and DPPF (7.5 mg, 0.013 mmol) in DMF (1 mL) was heated to 100° C. under microwave irradiation for 25 minutes. The reaction was cooled and diluted with ethyl acetate. The organic layer was collected, washed with water, brine, dried over sodium sulphate and concentrated in vacuo. The residue was purified using preparative TLC eluting with 5% MeOH in DCM to afford the LCMS (5 minute run) Rt=2.78 minutes MS m/z 425 [M+H]$^+$ Example 139

2-(5-cyanopyridin-2-yl)-N-(5-{[1-(propan-2-yl)-1H-pyrrolo[3,2-c]pyridin-3-yl]carbonyl}pyridin-3-yl) acetamide Prepared according to Method 3 using 2-(5-bromoyridin-2-yl)-N-(5-{[1-(propan-2-yl)-1H-pyrrolo[3,2-c]pyridin-3-yl]carbonyl}pyridin-3-yl)acetamide (Example 239). The residue was purified using preparative HPLC.

LCMS (5 minute run) Rt=2.68 minutes MS m/z 425 [M+H]$^+$

Example 140

2-(5-cyanopyridin-2-yl)-N-(2-{[1-(propan-2-yl)-1H-pyrrolo[3,2-c]pyridin-3-yl]carbonyl}pyridin-4-yl)acetamide

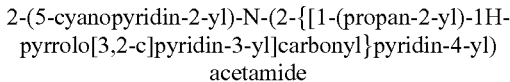

Prepared according to Method 3 using 2-(5-bromopyridin-2-yl)-N-(2-{[1-(propan-2-yl)-1H-pyrrolo[3,2-c]pyridin-3-yl]carbonyl}pyridin-4-yl)acetamide (Example 238). The residue was purified using preparative HPLC.

LCMS (5 minute run) Rt=1.98 minutes MS m/z 425 [M+H]$^+$

Library Protocol 3

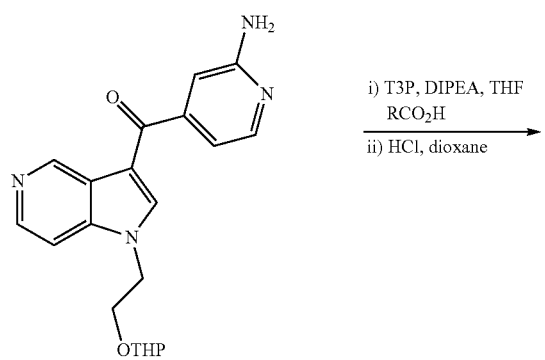

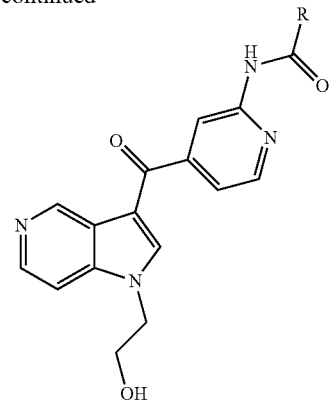

To a 0.2M solution of (2-aminopyridin-4-yl){1-[2-(tetrahydro-2H-pyran-2-yloxy)ethyl]-1H-pyrrolo[3,2-c]pyridin-3-yl}methanone in THF (Preparation 21, 500 μL, 100 umol) was added the required acid (130 μmol) followed by T3P (300 μmol). DIPEA (350 umol) was then added and the reaction stirred at room temperature for 16 hours. The reaction was concentrated in vacuo and the crude residue dissolved in 10% HCl in dioxane (1 mL) and stirred for 12 hours at room temperature. After concentration in vacuo the residue was purified using preparative HPLC to afford the desired compound.

Purification Method:

Column: X Bridge C18 OBD 50×19 mm, 5 μm, mobile phase A: 0.05% Ammonia in water (pH=10.5); mobile phase B: Acetonitrile. Initial gradient 10% B; 1 min 20% B, 7 mins 95% B, 8 mins 95% B, 8.5 mins 10% B, 10 mins 10% B. Flow rate 20 mL/min.

The following Examples were prepared in Library Protocol 3.

| Example | Name | Data |
|---|---|---|
| 141 | N-(4-{[1-(2-hydroxyethyl)-1H-pyrrolo[3,2-c]pyridin-3-yl]carbonyl}pyridin-2-yl)-2-[4-(trifluoromethyl)phenyl]acetamide | MS m/z 469 [M + H]$^+$ |
| 142 | N-(4-{[1-(2-hydroxyethyl)-1H-pyrrolo[3,2-c]pyridin-3-yl]carbonyl}pyridin-2-yl)-3-(trifluoromethoxy)benzamide | MS m/z 471 [M + H]$^+$ |
| 143 | N-(4-{[1-(2-hydroxyethyl)-1H-pyrrolo[3,2-c]pyridin-3-yl]carbonyl}pyridin-2-yl)-2-[2-(trifluoromethoxy)phenyl]acetamide | MS m/z 485 [M + H]$^+$ |
| 144 | 2-(3,4-dichlorophenyl)-N-(4-{[1-(2-hydroxyethyl)-1H-pyrrolo[3,2-c]pyridin-3-yl]carbonyl}pyridin-2-yl) | MS m/z 469 [M + H]$^+$ |
| 145 | 2-(2,4-difluorophenyl)-N-(4-{[1-(2-hydroxyethyl)-1H-pyrrolo[3,2-c]pyridin-3-yl]carbonyl}pyridin-2-yl)acetamide | MS m/z 437 [M + H]$^+$ |
| 146 | 2-(4-chlorophenyl)-N-(4-{[1-(2-hydroxyethyl)-1H-pyrrolo[3,2-c]pyridin-3-yl]carbonyl}pyridin-2-yl)acetamide | MS m/z 435 [M + H]$^+$ |
| 147 | N-(4-{[1-(2-hydroxyethyl)-1H-pyrrolo[3,2-c]pyridin-3-yl]carbonyl}pyridin-2-yl)-2-[5-(propan-2-yl)-1H-pyrazol-1-yl]acetamide | MS m/z 433 [M + H]$^+$ |
| 148 | 2-(4-fluorophenyl)-N-(4-{[1-(2-hydroxyethyl)-1H-pyrrolo[3,2-c]pyridin-3-yl]carbonyl}pyridin-2-yl)acetamide | MS m/z 419 [M + H]$^+$ |
| 149 | 2-(3-chlorophenyl)-N-(4-{[1-(2-hydroxyethyl)-1H-pyrrolo[3,2-c]pyridin-3-yl]carbonyl}pyridin-2-yl)acetamide | MS m/z 435 [M + H]$^+$ |
| 150 | N-(4-{[1-(2-hydroxyethyl)-1H-pyrrolo[3,2-c]pyridin-3-yl]carbonyl}pyridin-2-yl)-2-(3-methyl-1H-pyrazol-1-yl)acetamide | MS m/z 405 [M + H]$^+$ |
| 151 | N-(4-{[1-(2-hydroxyethyl)-1H-pyrrolo[3,2-c]pyridin-3-yl]carbonyl}pyridin-2-yl)-2-[3-(2-hydroxy-2-methylpropyl)phenyl]acetamide | MS m/z 473 [M + H]$^+$ |
| 152 | 2-(3,5-dimethyl-1H-pyrazol-1-yl)-N-(4-{[1-(2-hydroxyethyl)-1H-pyrrolo[3,2-c]pyridin-3-yl]carbonyl}pyridin-2-yl)acetamide | MS m/z 419 [M + H]$^+$ |
| 153 | N-(4-{[1-(2-hydroxyethyl)-1H-pyrrolo[3,2-c]pyridin-3-yl]carbonyl}pyridin-2-yl)-2-[5-methyl-3-(trifluoromethyl)-1H- pyrazol-1-yl]acetamide | MS m/z 473 [M + H]$^+$ |
| 154 | 2-(3-tert-butyl-1-methyl-1H-1,2,4-triazol-5-yl)-N-(4-{[1-(2-hydroxyethyl)-1H-pyrrolo[3,2-c]pyridin-3-yl]carbonyl}pyridin-2-yl)acetamide | MS m/z 462 [M + H]$^+$ |
| 155 | N-(4-{[1-(2-hydroxyethyl)-1H-pyrrolo[3,2-c]pyridin-3-yl]carbonyl}pyridin-2-yl)-2-(5-methyl-1H-pyrazol-1-yl)acetamide | MS m/z 405 [M + H]$^+$ |
| 156 | N-(4-{[1-(2-hydroxyethyl)-1H-pyrrolo[3,2-c]pyridin-3-yl]carbonyl}pyridin-2-yl)-2-[4-(trifluoromethyl)-1H-1,2,3-triazol-1-yl]acetamide | MS m/z 460 [M + H]$^+$ |

-continued

| Example | Name | Data |
|---|---|---|
| 157 | N-(4-{[1-(2-hydroxyethyl)-1H-pyrrolo[3,2-c]pyridin-3-yl]carbonyl}pyridin-2-yl)-2-[1-(propan-2-yl)-5-(trifluoromethyl)-1H-pyrazol-4-yl]acetamide | MS m/z 501 [M + H]+ |
| 158 | N-(4-{[1-(2-hydroxyethyl)-1H-pyrrolo[3,2-c]pyridin-3-yl]carbonyl}pyridin-2-yl)-2-(2H-1,2,3-triazol-2-yl)acetamide | MS m/z 392 [M + H]+ |
| 159 | N-(4-{[1-(2-hydroxyethyl)-1H-pyrrolo[3,2-c]pyridin-3-yl]carbonyl}pyridin-2-yl)-2-[4-(propan-2-yl)-1H-1,2,3-triazol-1-yl]acetamide | MS m/z 434 [M + H]+ |

Library Protocol 4

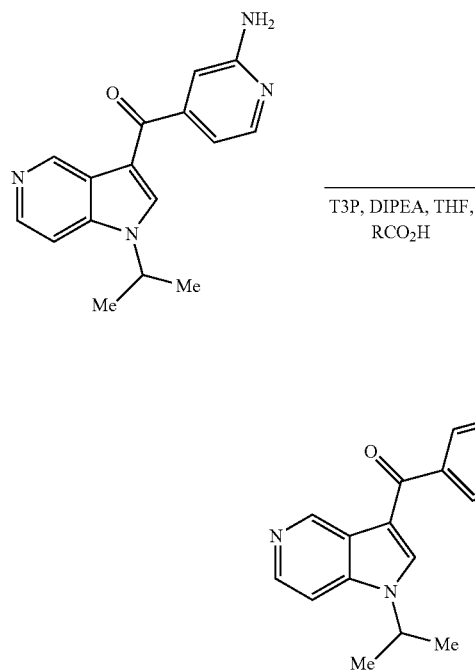

To a 0.2M solution of (2-Aminopyridin-4-yl)-(1-isopropyl-1H-pyrrolo[3,2-c]pyridin-3-yl)methanone in THF (Preparation 20, 500 μL, 100 umol) was added the required acid (130 μmol) followed by T3P (300 μmol). DIPEA (350 μmol) was then added and the reaction stirred at room temperature for 16 hours. The reaction was concentrated in vacuo and the crude residue was purified using preparative HPLC to afford the desired compound.

Purification Method:

Column: XBridge C18 ODB 50×19 mm, 5 um mobile phase A: 0.05% Ammonia in water pH=10.5; mobile phase B: Acetonitrile. Initial gradient 10% B; 1 min 20% B, 7 mins 95% B, 8 mins 95% B, 8.5 mins 10% B. Flow rate 20 mL/min.

The following Examples were prepared in Library Protocol 4:

| Example | Name | Data |
|---|---|---|
| 160 | 2-(3,5-dimethyl-1,2-oxazol-4-yl)-N-(4-{[1-(propan-2-yl)-1H-pyrrolo[3,2-c]pyridin-3-yl]carbonyl}pyridin-2-yl)acetamide | MS m/z 418 [M + H]+ |
| 161 | 2-(2-methyl-1,3-thiazol-4-yl)-N-(4-{[1-(propan-2-yl)-1H-pyrrolo[3,2-c]pyridin-3-yl]carbonyl}pyridin-2-yl)acetamide | MS m/z 420 [M + H]+ |
| 162 | 2-(2,5-dimethyl-1,3-thiazol-4-yl)-N-(4-{[1-(propan-2-yl)-1H-pyrrolo[3,2-c]pyridin-3-yl]carbonyl}pyridin-2-yl)acetamide | MS m/z 434 [M + H]+ |
| 163 | N-(4-{[1-(propan-2-yl)-1H-pyrrolo[3,2-c]pyridin-3-yl]carbonyl}pyridin-2-yl)-2-[4-(trifluoromethyl)-1H-1,2,3-triazol-1-yl]acetamide | MS m/z 458 [M + H]+ |
| 164 | 2-(3,5-dimethyl-1H-pyrazol-1-yl)-N-(4-{[1-(propan-2-yl)-1H-pyrrolo[3,2-c]pyridin-3-yl]carbonyl}pyridin-2-yl)acetamide | MS m/z 417 [M + H]+ |
| 165 | 2-(3,4-dichlorophenyl)-N-(4-{[1-(propan-2-yl)-1H-pyrrolo[3,2-c]pyridin-3-yl]carbonyl}pyridin-2-yl)acetamide | MS m/z 467 [M + H]+ |
| 166 | N-(4-{[1-(propan-2-yl)-1H-pyrrolo[3,2-c]pyridin-3-yl]carbonyl}pyridin-2-yl)-2-(1H-pyrazol-1-yl)acetamide | MS m/z 389 [M + H]+ |
| 167 | 2-(2,4-dimethyl-1,3-thiazol-5-yl)-N-(4-{[1-(propan-2-yl)-1H-pyrrolo[3,2-c]pyridin-3-yl]carbonyl}pyridin-2-yl)acetamide | MS m/z 434 [M + H]+ |
| 168 | N-(4-{[1-(propan-2-yl)-1H-pyrrolo[3,2-c]pyridin-3-yl]carbonyl}pyridin-2-yl)-2-[4-(trifluoromethoxy)phenyl]acetamide | MS m/z 458 [M + H]+ |
| 169 | 2-(5-methyl-1H-pyrazol-1-yl)-N-(4-{[1-(propan-2-yl)-1H-pyrrolo[3,2-c]pyridin-3-yl]carbonyl}pyridin-2-yl)acetamide | MS m/z 403 [M + H]+ |
| 170 | N-(4-{[1-(propan-2-yl)-1H-pyrrolo[3,2-c]pyridin-3-yl]carbonyl}pyridin-2-yl)-2-(1H-tetrazol-1-yl)acetamide | MS m/z 391 [M + H]+ |
| 171 | 2-(3-tert-butyl-1-methyl-1H-1,2,4-triazol-5-yl)-N-(4-{[1-(propan-2-yl)-1H-pyrrolo[3,2-c]pyridin-3-yl]carbonyl}pyridin-2-yl)acetamide | MS m/z 460 [M + H]+ |
| 172 | 2-(3-fluoro-4-(trifluoromethyl)phenyl]-N-(4-{[1-(propan-2-yl)-1H-pyrrolo[3,2-c]pyridin-3-yl]carbonyl}pyridin-2-yl)acetamide | MS m/z 485 [M + H]+ |
| 173 | N-(4-{[1-(propan-2-yl)-1H-pyrrolo[3,2-c]pyridin-3-yl]carbonyl}pyridin-2-yl)-3-(trifluoromethoxy)benzamide | MS m/z 469 [M + H]+ |
| 174 | 2-(5-cyclopropyl-2-methyl-1,3-oxazol-4-yl)-N-(4-{[1-(propan-2-yl)-1H-pyrrolo[3,2-c]pyridin-3-yl]carbonyl}pyridin-2-yl)acetamide | MS m/z 444 [M + H]+ |
| 175 | N-(4-{[1-(propan-2-yl)-1H-pyrrolo[3,2-c]pyridin-3-yl]carbonyl}pyridin-2-yl)-2-[4-(trifluoromethyl)phenyl]acetamide | MS m/z 467 [M + H]+ |
| 176 | 2-(4-(methoxymethyl)-1H-1,2,3-triazol-1-A-N-(4-{[1-(propan-2-yl)-1H-pyrrolo[3,2-c]pyridin-3-yl]carbonyl}pyridin-2-yl)acetamide | MS m/z 434 [M + H]+ |
| 177 | 2-(3-methyl-1H-pyrazol-5-yl)-N-(4-{[1-(propan-2-yl)-1H-pyrrolo[3,2-c]pyridin-3-yl]carbonyl}pyridin-2-yl)acetamide | MS m/z 403 [M + H]+ |
| 178 | N-(4-{[1-(propan-2-yl)-1H-pyrrolo[3,2-c]pyridin-3-yl]carbonyl}pyridin-2-yl)-2-[1-(propan-2-yl)-5-(trifluoromethyl)-1H-pyrazol-4-yl]acetamide | MS m/z 499 [M + H]+ |
| 179 | 2-(2,5-dimethyl-1,3-oxazol-4-yl)-N-(4-{[1-(propan-2-yl)-1H-pyrrolo[3,2-c]pyridin-3-yl]carbonyl}pyridin-2-yl)acetamide | MS m/z 418 [M + H]+ |
| 180 | 2-(1,2-oxazol-3-yl)-N-(4-{[1-(propan-2-yl)-1H-pyrrolo[3,2-c]pyridin-3-yl]carbonyl}pyridin-2-yl)acetamide | MS m/z 390 [M + H]+ |
| 181 | N-(4-{[1-(propan-2-yl)-1H-pyrrolo[3,2-c]pyridin-3-yl]carbonyl}pyridin-2-yl)-2(1,3-thiazol-4-yl)acetamide | MS m/z 406 [M + H]+ |
| 182 | N-(4-{[1-(propan-2-yl)-1H-pyrrolo[3,2-c]pyridin-3-yl]carbonyl}pyridin-2-yl)-2-[2-(trifluoromethoxy)phenyl]acetamide | MS m/z 483 [M + H]+ |

-continued

| Example | Name | Data |
|---|---|---|
| 183 | 2-(4-cyanophenyl)-N-(4-{[1-(propan-2-yl)-1H-pyrrolo[3,2-c]pyridin-3-yl]carbonyl}pyridin-2-yl)acetamide | MS m/z 424 [M + H]+ |
| 184 | 2-(3-methyl-1H-1,2,4-triazol-5-yl)-N-(4-{[1-(propan-2-yl)-1H-pyrrolo[3,2-c]pyridin-3-yl]carbonyl}pyridin-2-yl)acetamide | MS m/z 404 [M + H]+ |
| 185 | N-(4-{[1-(propan-2-yl)-1H-pyrrolo[3,2-c]pyridin-3-yl]carbonyl}pyridin-2-yl)-2-(1,3-thiazol-5-yl)acetamide | MS m/z 406 [M + H]+ |
| 186 | 2-(4-fluorophenyl)-N-(4-{[1-(propan-2-yl)-1H-pyrrolo[3,2-c]pyridin-3-yl]carbonyl}pyridin-2-yl)acetamide | MS m/z 417 [M + H]+ |
| 187 | N-(4-{[1-(propan-2-yl)-1H-pyrrolo[3,2-c]pyridin-3-yl]carbonyl}pyridin-2-yl)-2-(1H-tetrazol-5-yl)acetamide | MS m/z 391 [M + H]+ |
| 188 | 2-[4-(2-hydroxypropan-2-yl)-1H-1,2,3-triazol-1-yl]-N-(4-{[1-(propan-2-yl)-1H-pyrrolo[3,2-c]pyridin-3-yl]carbonyl}pyridin-2-yl)acetamide | MS m/z 448 [M + H]+ |
| 189 | 2-(2-cyclopropyl-1,3-oxazol-4-yl)-N-(4-{[1-(propan-2-yl)-1H-pyrrolo[3,2-c]pyridin-3-yl]carbonyl}pyridin-2-yl)acetamide | MS m/z 430 [M + H]+ |
| 190 | N-(4-{[1-(propan-2-yl)-1H-pyrrolo[3,2-c]pyridin-3-yl]carbonyl}pyridin-2-yl)-2-(2H-1,2,3-triazol-2-yl)acetamide | MS m/z 390 [M + H]+ |
| 191 | N-(4-{[1-(propan-2-yl)-1H-pyrrolo[3,2-c]pyridin-3-yl]carbonyl}pyridin-2-yl)-2-[3-(trifluoromethoxy)phenyl]acetamide | MS m/z 483 [M + H]+ |
| 192 | 2-(1-methyl-1H-tetrazol-5-yl)-N-(4-{[1-(propan-2-yl)-1H-pyrrolo[3,2-c]pyridin-3-yl]carbonyl}pyridin-2-yl)acetamide | MS m/z 405 [M + H]+ |
| 193 | N-(4-{[1-(propan-2-yl)-1H-pyrrolo[3,2-c]pyridin-3-yl]carbonyl}pyridin-2-yl)-2-(1H-1,2,4-triazol-1-yl)acetamide | MS m/z 390 [M + H]+ |

Library Protocol 5

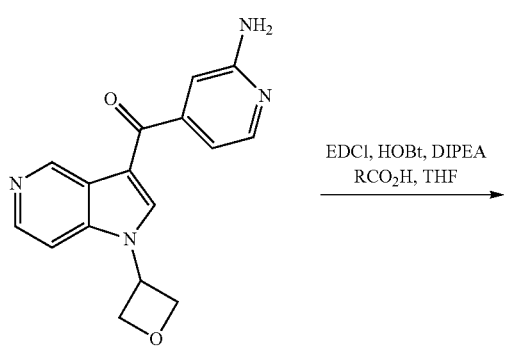

To a 0.2M solution of (2-Aminopyridin-4-yl)-(1-(oxetan-3-yl)-1H-pyrrolo[3,2-c]pyridin-3-yl)methanone in THF (Preparation 24, 500 µL, 100 umol) was added a 0.26M solution of the appropriate acetic acid in THF (500 µL, (130 µmol), DIPEA (130 µmol), EDCI (130 µmol) followed by HOBt (100 µmol) and the reaction was stirred under microwave irradiation for 30 minutes at 70° C. The reaction mixture was concentrated in vacuo and purified using preparative HPLC to afford the title compound.

Purification Method:

Column: X Bridge C18 OBD 50×19 mm, 5 µm, mobile phase A: 0.05% Ammonia in water (pH=10.5); mobile phase B: Acetonitrile. Initial gradient 5% B; Final gradient 45% B. Flow rate 20 mL/min.

The following Examples were prepared in Library Protocol 5:

| Example | Name | Data |
|---|---|---|
| 194 | N-(4-{[1-(oxetan-3-yl)-1H-pyrrolo[3,2-c]pyridin-3-yl]carbonyl}pyridin-2-yl)-2-[3-(trifluoromethoxy)phenyl]acetamide | MS m/z 497 [M + H]+ |
| 195 | 2-(4-cyanophenyl)-N-(4-{[1-(oxetan-3-yl)-1H-pyrrolo[3,2-c]pyridin-3-yl]carbonyl}pyridin-2-yl)acetamide | MS m/z 438 [M + H]+ |
| 196 | 2-(5-fluoropyridin-2-yl)-N-(4-{[1-(oxetan-3-yl)-1H-pyrrolo[3,2-c]pyridin-3-yl]carbonyl}pyridin-2-yl)acetamide | MS m/z 432 [M + H]+ |
| 197 | 2-(2-cyclopropyl-1,3-oxazol-4-yl)-N-(4-{[1-(oxetan-3-yl)-1H-pyrrolo[3,2-c]pyridin-3-yl]carbonyl}pyridin-2-yl)acetamide | MS m/z 444 [M + H]+ |
| 198 | 2-(2,4-difluorophenyl)-N-(4-{[1-(oxetan-3-yl)-1H-pyrrolo[3,2-c]pyridin-3-yl]carbonyl}pyridin-2-yl)acetamide | MS m/z 449 [M + H]+ |
| 199 | N-(4-{[1-(oxetan-3-yl)-1H-pyrrolo[3,2-c]pyridin-3-yl]carbonyl}pyridin-2-yl)-2-[4-(propan-2-yl)-1H-1,2,3-triazol-1-yl]acetamide | MS m/z 446 [M + H]+ |
| 200 | 2-(2-cyclopropyl-5-methyl-1,3-oxazol-4-yl)-N-(4-{[1-(oxetan-3-yl)-1H-pyrrolo[3,2-c]pyridin-3-yl]carbonyl}pyridin-2-yl)acetamide | MS m/z 458 [M + H]+ |
| 201 | N-(4-{[1-(oxetan-3-yl)-1H-pyrrolo[3,2-c]pyridin-3-yl]carbonyl}pyridin-2-yl)-2-0-(propan-2-yl)-5-(trifluoromethyl)-1H-pyrazol-4-yl]acetamide | MS m/z 513 [M + H]+ |
| 202 | 2-(2,5-dicyclopropyl-1,3-oxazol-4-yl)-N-(4-{[1-(oxetan-3-yl)-1H-pyrrolo[3,2-c]pyridin-3-yl]carbonyl}pyridin-2-yl)acetamide | MS m/z 484 [M + H]+ |
| 203 | 2-(2,5-dicyclopropyl-1,3-oxazol-4-yl)-N-(4-{[1-(oxetan-3-yl)-1H-pyrrolo[3,2-c]pyridin-3-yl]carbonyl}pyridin-2-yl)acetamide | MS m/z 497 [M + H]+ |
| 204 | 2-(4-fluorophenyl)-N-(4-{[1-(oxetan-3-yl)-1H-pyrrolo[3,2-c]pyridin-3-yl]carbonyl}pyridin-2-yl)acetamide | MS m/z 431 [M + H]+ |
| 205 | N-(4-{[1-(oxetan-3-yl)-1H-pyrrolo[3,2-c]pyridin-3-yl]carbonyl}pyridin-2-yl)-3-(trifluoromethoxy)benzamide | MS m/z 483 [M + H]+ |

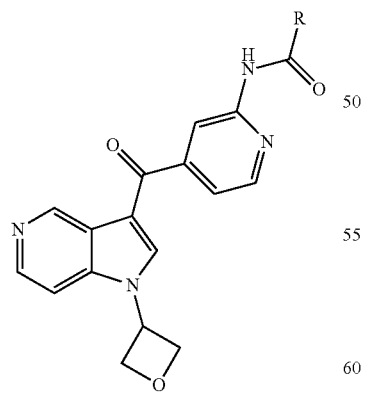

Example 206

2-(4-chlorophenyl)-N-(5-{[7-fluoro-1-(1-hydroxypropan-2-yl)-1H-pyrrolo[3,2-c]pyridin-3-yl]carbonyl}pyridin-3-yl)acetamide Method M To a mixture of (5-aminopyridin-3-yl)[7-fluoro-1-(2-hydroxy-1-methylethyl)-1H-pyrrolo[3,2-c]pyridin-3-yl]methanone (Enantiomer 2, Preparation 26, 50 mg, 0.159 mmol) and 4-chlorophenylacetic acid (27.2 mg, 0.159 mmol) in pyridine (1 mL) was added HATU (121 mg, 0.31 mmol) and the reaction was stirred at room temperature for 16 hours. The reaction was diluted with EtOAc, washed with saturated aqueous NaHCO3 solution, brine, dried over sodium sulphate and concentrated in vacuo. The residue was purified using preparative TLC eluting with 7% MeOH in DCM to afford the title compound (28 mg).

LCMS (5 minute run) Rt=2.96 minutes MS m/z 467 [M+H]+

The following Examples were prepared according to Method M using (5-aminopyridin-3-yl)[7-fluoro-1-(2-hydroxy-1-methylethyl)-1H-pyrrolo[3,2-c]pyridin-3-yl]methanone (Preparation 26, Enantiomer 1 or 2) and purified using preparative TLC eluting with 5-7% MeOH in DCM or EtOAc.

| | Example Name/Structure | Data |
|---|---|---|
| 207 | 2-(4-cyclopropyl-1H-1,2,3-triazol-1-yl)-N-(5-{[7-fluoro-1-(1-hydroxypropan-2-yl)-1H-pyrrolo[3,2-c]pyridin-3-yl]carbonyl}pyridin-3-yl)acetamide Enantiomer 2 | MS m/z 464 [M + H]+ Using Enantiomer 2 and (4-cyclopropyl-1H-1,2,3-triazol-1-yl)acetic acid (Preparation 94). |
| 208 | N-(5-{[7-fluoro-1-(1-hydroxypropan-2-yl)-1H-pyrrolo[3,2-c]pyridin-3-yl]carbonyl}pyridin-3-yl)-2-[3-(trifluoromethyl)-1H-pyrazol-1-yl]acetamide Enantiomer 2 | MS m/z 491 [M + H]+ Using Enantiomer 2 and [3-(trifluoromethyl)-1H-pyrazol-1-yl]acetic acid (Preparation 74). |
| 209 | N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)phenyl]acetamide Enantiomer 1 | MS m/z 464 [M + H]+ Using Enantiomer 1 and (4-cyclopropyl-1H-1,2,3-triazol-1-yl)acetic acid (Preparation 94). |
| 210 | N-(5-{[7-fluoro-1-(1-hydroxypropan-2-yl)-1H-pyrrolo[3,2-c]pyridin-3-yl]carbonyl}pyridin-3-yl)-2-[3-(trifluoromethyl)-1H-pyrazol-1-yl]acetamide Enantiomer 1 | MS m/z 491 [M + H]+ Using Enantiomer 1 and [3-(trifluoromethyl)-1H-pyrazol-1-yl]acetic acid (Preparation 74). |
| 211 | 2-(5-chloropyridin-2-yl)-N-(5-{[7-fluoro-1-(1-hydroxypropan-2-yl)-1H-pyrrolo[3,2-c]pyridin-3-yl]carbonyl}pyridin-3-yl)acetamide Enantiomer 1 | MS m/z 468 [M + H]+ Using Enantiomer 1 and (5-chloropyridin-2-yl)acetic acid (Preparation 80). |
| 212 | N-(5-{[7-fluoro-1-(1-hydroxypropan-2-yl)-1H-pyrrolo[3,2-c]pyridin-3-yl]carbonyl}pyridin-3-yl)-2-(5-fluoropyridin-2-yl)acetamide Enantiomer 2 | MS m/z 452 [M + H]+ Using Enantiomer 2 and (5-fluoropyridin-2-yl)acetic acid (Preparation 82). |
| 213 | 2-(4-cyanophenyl)-N-(5-{[7-fluoro-1-(1-hydroxypropan-2-yl)-1H-pyrrolo[3,2-c]pyridin-3-yl]carbonyl}pyridin-3-yl)acetamide Enantiomer 2 | MS m/z 458 [M + H]+ Using Enantiomer 2 and 4-cyanophenylacetic acid. |
| 214 | N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide Enantiomer 2 | MS m/z 505 [M + H]+ Using Enantiomer 2 and [4-(trifluoromethyl)-1H-1,2,3-triazol-1-yl]acetic acid (Preparation 90). |
| 215 | 2-(3-cyclopropyl-1H-pyrazol-1-yl)-N-(5-{[7-fluoro-1-(1-hydroxypropan-2-yl)-1H-pyrrolo[3,2-c]pyridin-3-yl]carbonyl}pyridin-3-yl)acetamide Enantiomer 2 | m/z 463 [M + H]+ Using Enantiomer 2 and (3-cyclopropyl-1H-pyrazol-1-yl)acetic acid (Preparation 76). |
| 216 | N-(5-{[7-fluoro-1-(1-hydroxypropan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide Enantiomer 1 | MS m/z 505 [M + H]+ Using Enantiomer 1 and [5-methyl-3-(trifluoromethyl)-1H-pyrazol-1-yl]acetic acid. |
| 217 | 2-(4-cyanophenyl)-N-(5-{[7-fluoro-1-(1-hydroxypropan-2-yl)-1H-pyrrolo[3,2-c]pyridin-3-yl]carbonyl}pyridin-3-yl)acetamide Enantiomer 1 | MS m/z 458 [M + H]+ Using Enantiomer 1 and 4-cyanophenylacetic acid. |
| 218 | N-(5-{[7-fluoro-1-(1-hydroxypropan-2-yl)-1H-pyrrolo[3,2-c]pyridin-3-yl]carbonyl}pyridin-3-yl)-2-(5-fluoropyridin-2-yl)acetamide Enantiomer 1 | MS m/z 452 [M + H]+ Using Enantiomer 1 and (5-fluoropyridin-2-yl)acetic acid (Preparation 82). |
| 219 | N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)-1H-pyrazol-1-yl]acetamide Enantiomer 1 | MS m/z 491 [M + H]+ Using Enantiomer 1 and [4-(trifluoromethyl)-1H-pyrazol-1-yl]acetic acid (Preparation 78). |

-continued

| Example | Name/Structure | Data |
|---|---|---|
| 220 | N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)-1H-1,2,3-triazol-1-yl]acetamide Enantiomer 1 | MS m/z 492 [M + H]+ Using Enantiomer 1 and [4-(trifluoromethyl)-1H-1,2,3-triazol-1-yl]acetic acid (Preparation 90). |

Example 221

2-[4-cyano-3-(trifluoromethyl)phenyl]-N-(4-{[1-(oxetan-3-yl)-1H-pyrrolo[3,2-c]pyridin-3-yl]carbonyl}pyridin-2-yl)acetamide Prepared according to Method M (Example 206) using 2-Aminopyridin-4-yl)-(1-(oxetan-3-yl)-1H-pyrrolo[3,2-c]pyridin-3-yl)methanone (Preparation 24) and [4-cyano-3-(trifluoromethyl)phenyl]acetic acid (Preparation 95) at 50° C. for 3 hours. Purified using preparative HPLC.
LCMS Rt=2.30 minutes MS m/z 506 [M+H]+

Example 222

N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)phenyl]acetamide Prepared according to Method M (Example 206) using 4-trifluoromethylphenylacetic acid and (5-aminopyridin-3-yl)[7-fluoro-1-(2-hydroxy-1-methylethyl)-1H-pyrrolo[3,2-c]pyridin-3-yl]methanone (Enantiomer 2, Preparation 26).
LCMS (5 minute run) Rt=2.96 minutes MS m/z 501 [M+H]+

Example 223

2-(4-chlorophenyl)-N-(5-{[7-fluoro-1-(1-hydroxypropan-2-yl)-1H-pyrrolo[3,2-c]pyridin-3-yl]carbonyl}pyridin-3-yl)acetamide Prepared according to Method M (Example 206) using 4-chlorophenylacetic acid and (5-aminopyridin-3-yl)[7-fluoro-1-(2-hydroxy-1-methylethyl)-1H-pyrrolo[3,2-c]pyridin-3-yl]methanone (Enantiomer 1, Preparation 26).
LCMS (5 minute run) Rt=2.96 minutes MS m/z 467 [M+H]+

Example 224

N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)phenyl]acetamide Prepared according to Method M (Example 206) using 4-trifluoromethylphenylacetic acid and (5-aminopyridin-3-yl)[7-fluoro-1-(2-hydroxy-1-methylethyl)-1H-pyrrolo[3,2-c]pyridin-3-yl]methanone (Enantiomer 1, Preparation 26).
LCMS (5 minute run) Rt=3.04 minutes MS m/z 501 [M+H]+

Example 225

2-(5-chloropyridin-2-yl)-N-(5-{[7-fluoro-1-(1-hydroxypropan-2-yl)-1H-pyrrolo[3,2-c]pyridin-3-yl]carbonyl}pyridin-3-yl)acetamide Prepared according to Method M (Example 206) using (5-chloropyridin-2-yl)acetic acid (Preparation 80) and (5-aminopyridin-3-yl)[7-fluoro-1-(2-hydroxy-1-methylethyl)-1H-pyrrolo[3,2-c]pyridin-3-yl]methanone (Enantiomer 2, Preparation 26). The residue was purified using preparative TLC eluting with 5% MeOH in EtOAc.
LCMS (5 minute run) Rt=2.64 minutes MS m/z 468 [M+H]+

Example 226

N-(5-{[7-fluoro-1-(1-hydroxypropan-2-yl)-1H-pyrrolo[3,2-c]pyridin-3-yl]carbonyl}pyridin-3-yl)-2-[3-(trifluoromethyl)phenyl]acetamide Prepared according to Method M (Example 206) using 3-trifluoromethylphenylacetic acid and (5-aminopyridin-3-yl)[7-fluoro-1-(2-hydroxy-1-methylethyl)-1H-pyrrolo[3,2-c]pyridin-3-yl]methanone (Enantiomer 2, Preparation 26). The residue was purified using preparative TLC eluting with 5% MeOH in EtOAc.
LCMS (5 minute run) Rt=3.03 minutes MS m/z 501 [M+H]+

Example 227

N-(5-{[7-fluoro-1-(1-hydroxypropan-2-yl)-1H-pyrrolo[3,2-c]pyridin-3-yl]carbonyl}pyridin-3-yl)-2-[4-(trifluoromethyl)-1H-pyrazol-1-yl]acetamide Prepared according to Method M (Example 206) using [4-(trifluoromethyl)-1H-pyrazol-1-yl]acetic acid (Preparation 74) and (5-aminopyridin-3-yl)[7-fluoro-1-(2-hydroxy-1-methylethyl)-1H-pyrrolo[3,2-c]pyridin-3-yl]methanone (Enantiomer 2, Preparation 26). The residue was purified using preparative TLC eluting with 5% MeOH in EtOAc.
LCMS (5 minute run) Rt=2.85 minutes MS m/z 491 [M+H]+

Example 228

N-(5-{[7-fluoro-1-(1-hydroxypropan-2-yl)-1H-pyrrolo[3,2-c]pyridin-3-yl]carbonyl}pyridin-3-yl)-2-[5-methyl-3-(trifluoromethyl)-1H-pyrazol-1-yl]acetamide Prepared according to Method M (Example 206) using [5-methyl-3-(trifluoromethyl)-1H-pyrazol-1-yl]acetic acid and (5-aminopyridin-3-yl)[7-fluoro-1-(2-hydroxy-1-methylethyl)-1H-pyrrolo[3,2-c]pyridin-3-yl]methanone (Enantiomer 2, Preparation 26). The residue was purified using preparative TLC eluting with 5% MeOH in EtOAc.

LCMS (5 minute run) Rt=2.90 minutes MS m/z 505 [M+H]⁺

Example 229

N-(2-{[1-(1-hydroxypropan-2-yl)-1H-pyrrolo[3,2-c]pyridin-3-yl]carbonyl}pyridin-4-yl)-2-[3-(trifluoromethyl)phenyl]acetamide

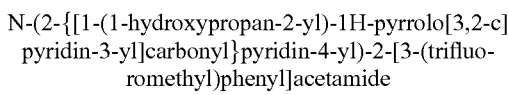

Prepared according to method described for Method 1 (Example 19) using (4-aminopyridin-2-yl)[1-(2-{[tert-butyl(dimethyl)silyl]oxy}-1-methylethyl)-1H-pyrrolo[3,2-c]pyridin-3-yl]methanone (Enantiomer 1, Preparation 30) and 3-trifluoromethylphenylacetic acid. The residue was partitioned between EtOAc and saturated aqueous NaHCO₃ solution, the organic layer collected, washed with brine, dried over sodium sulphate and concentrated in vacuo. The residue was dissolved in THF and 10% HCl in dioxane was added. The reaction was stirred at room temperature for 18 hours. The reaction was concentrated in vacuo and purified using preparative HPLC to afford the title compound.

LCMS (5 minute run) Rt=2.96 minutes MS m/z 483 [M+H]⁺

Example 230

N-(2-{[1-(1-hydroxypropan-2-yl)-1H-pyrrolo[3,2-c]pyridin-3-yl]carbonyl}pyridin-4-yl)-2-[4-(trifluoromethyl)phenyl]acetamide Prepared according to Example 229 using 4-trifluoromethylphenylacetic acid. LCMS (5 minute run) Rt=2.99 minutes MS m/z 483 [M+H]⁺

Example 231

N-(2-{[1-(1-hydroxy-2-methylpropan-2-yl)-1H-pyrrolo[3,2-c]pyridin-3-yl]carbonyl}pyridin-4-yl)-2-[4-(trifluoromethyl)phenyl]acetamide

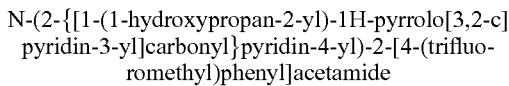

Prepared according to Method M (Example 206) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) and 4-trifluoromethylphenylacetic acid at 70° C. The residue was purified over neutral alumina eluting with 50% EtOAc in hexane followed by acid deprotection using 10% HCl in dioxane at room temperature for 18 hours. The reaction was concentrated in vacuo and purified using preparative HPLC to afford the title compound.

LCMS (5 minute run) Rt=3.14 minutes MS m/z 497 [M+H]⁺

Example 232

N-(2-{[1-(1-hydroxy-2-methylpropan-2-yl)-1H-pyrrolo[3,2-c]pyridin-3-yl]carbonyl}pyridin-4-yl)-2-[3-(trifluoromethyl)phenyl]acetamide

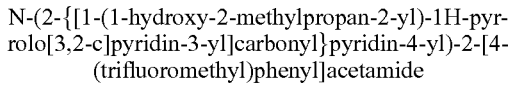

Prepared according to Method M (Example 206) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) and 3-trifluoromethylphenylacetic acid at 70° C. The residue was purified over neutral alumina eluting with 50%-60% EtOAc in hexane followed by acid deprotection using 10% HCl in dioxane at room temperature for 18 hours. The reaction was concentrated in vacuo and purified using preparative HPLC to afford the title compound.

LCMS (5 minute run) Rt=3.05 minutes MS m/z 497 [M+H]⁺

Example 233

2-[4-cyano-3-(trifluoromethyl)phenyl]-N-(4-{[1-(propan-2-yl)-1H-pyrrolo[3,2-c]pyridin-3-yl]carbonyl}pyridin-2-yl)acetamide

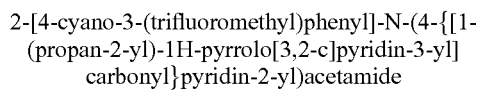

Prepared according to Method M (Example 206) at 60° C. for 16 hours followed by 70° C. for a further 16 hours using (2-aminopyridin-4-yl)-(1-isopropyl-1H-pyrrolo[3,2-c]pyridin-3-yl)methanone (Preparation 20) and [4-cyano-3-(trifluoromethyl)phenyl]acetic acid (Preparation 95). Purified using silica gel column chromatography eluting with 5-7% MeOH in DCM.

LCMS (5 minute run) Rt=3.33 minutes MS m/z 492 [M+H]⁺

Example 234

2-(3-cyclopropyl-1H-pyrazol-1-yl)-N-(2-{[1-(1-hydroxy-2-methylpropan-2-yl)-1H-pyrrolo[3,2-c]pyridin-3-yl]carbonyl}pyridin-4-yl)acetamide

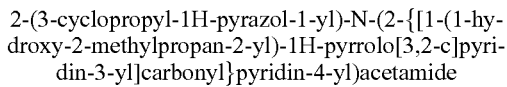

Prepared according to Method 1 (Example 19) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) at 60° C. The residue was purified using preparative HPLC to afford the deprotected title compound.

LCMS (5 minute run) Rt=2.67 minutes MS m/z 459 [M+H]⁺

Example 235

N-(5-{[1-(1-hydroxy-2-methylpropan-2-yl)-1H-pyrrolo[3,2-c]pyridin-3-yl]carbonyl}pyridin-3-yl)-2-[3-(trifluoromethyl)phenyl]acetamide

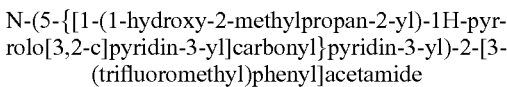

Prepared according to Method 1 (Example 19) using (5-aminopyridin-3-yl)[1-(2-{[tert-butyl(dimethyl)silyl]oxy}-1,1-dimethylethyl)-1H-pyrrolo[3,2-c]pyridin-3-yl]methanone (Preparation 28), 3-trifluoromethylphenylacetic acid and DIPEA. The residue was purified using silica gel column chromatography eluting with 80% EtOAc in hexane followed by acid deprotection using 10% HCl in dioxane at room temperature for 18 hours. The reaction was concentrated in vacuo and purified using preparative HPLC to afford the title compound.

LCMS (5 minute run) Rt=2.90 minutes MS m/z 497 [M+H]⁺

Example 236

N-(5-{[1-(1-hydroxy-2-methylpropan-2-yl)-1H-pyrrolo[3,2-c]pyridin-3-yl]carbonyl}pyridin-3-yl)-2-[3-(trifluoromethyl)-1H-pyrazol-1-yl]acetamide

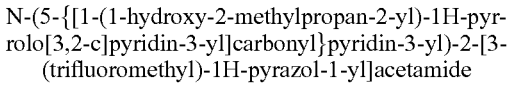

Prepared according to Method 1 (Example 19) using 5-aminopyridin-3-yl)[1-(2-{[tert-butyl(dimethyl)silyl]oxy}-1,1-dimethylethyl)-1H-pyrrolo[3,2-c]pyridin-3-yl]methanone (Preparation 28), 3-(trifluoromethyl)-1H-pyrazol-1-yl]acetic acid (Preparation 78) and DIPEA. The residue was purified using silica gel column chromatography eluting with 80% EtOAc in hexane followed by acid deprotection using 10% HCl in dioxane at room temperature for 18 hours. The reaction was concentrated in vacuo and purified using preparative HPLC to afford the title compound.

LCMS (5 minute run) Rt=2.73 minutes MS m/z 487 [M+H]$^+$

Example 237

2-(5-bromopyridin-2-yl)-N-(4-{[1-(propan-2-yl)-1H-pyrrolo[3,2-c]pyridin-3-yl]carbonyl}pyridin-2-yl)acetamide To a solution of (5-bromopyridin-2-yl)acetic acid (Preparation 83, 92 mg, 0.427 mmol) and (2-aminopyridin-4-yl)(1-isopropyl-1H-pyrrolo[3,2-c]pyridin-3-yl)methanone (Preparation 20, 120 mg, 0.427 mmol) in THF (3 mL) was added propylphosphonic anhydride (786 uL, 1.281 mmol) and triethylamine (151 uL, 1.99 mmol) and the reaction was stirred at room temperature for 18 hours. The reaction was diluted with EtOAc, washed with saturated aqueous NaHCO$_3$ solution, brine, dried over Na$_2$SO$_4$ and concentrated in vacuo. The residue was purified using preparative TLC eluting with 5% MeOH in DCM to afford the title compound.

LCMS (5 minute run in NH4OAc.MeCN) Rt=2.97 minutes MS m/z 478 [M+H]$^+$

Example 238

2-(5-bromopyridin-2-yl)-N-(2-{[1-(propan-2-yl)-1H-pyrrolo[3,2-c]pyridin-3-yl]carbonyl}pyridin-4-yl)acetamide Prepared according to the method described for Example 237 using (4-Aminopyridin-2-yl)-(1-isopropyl-1H-pyrrolo[3,2-c]pyridine-3-yl)methanone (Preparation 22). Purified using silica gel column chromatography eluting with 5% MeOH in DCM to afford the title compound.

LCMS (5 minute run) Rt=3.24 minutes MS m/z 478 [M+H]$^+$

Example 239

2-(5-bromoyridin-2-yl)-N-(5-{[1-(propan-2-yl)-1H-pyrrolo[3,2-c]pyridin-3-yl]carbonyl}pyridin-3-yl)acetamide Prepared according to the method described for Example 237 using (5-aminopyridin-3-yl)(1-isopropyl-1H-pyrrolo[3,2-c]pyridin-3-yl)methanone (Preparation 19). Purified using silica gel column chromatography eluting with EtOAc to afford the title compound. LCMS (5 minute run) Rt=3.02 minutes MS m/z 478 [M+H]$^+$ Example 240

2-(4-cyclopropyl-1H-1,2,3-triazol-1-yl)-N-(5-{[7-fluoro-1-(1-hydroxy-2-methylpropan-2-yl)-1H-pyrrolo[3,2-c]pyridin-3-yl]carbonyl}pyridin-3-yl)acetamide Prepared according to Method 1 (Example 19) followed by Method Y (Example 1) using (5-Amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29) and (4-cyclopropyl-1H-1,2,3-triazol-1-yl)acetic acid (Preparation 94).

LCMS (5 minute run) Rt=2.57 minutes MS m/z 478 [M+H]$^+$

PREPARATIONS

Preparation 1

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-trifluoromethyl-phenyl)-acetamide

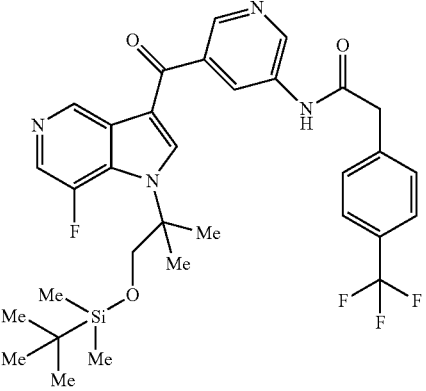 [SMILES: CC(C)(CO[Si](C)(C)C(C)(C)C)n1cc(C(=O)c2cncc(NC(=O)Cc3ccc(C(F)(F)F)cc3)c2)c2cncc(F)c21]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79 μmol), (4-trifluoromethyl-phenyl)-acetic acid (21.8 mg, 106 μmol) and DIPEA (48.94 μL, 277 μmol) in THF (3 mL), T3P (166 μL, 277 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as a white solid. (91%, 45 mg).

$^1$H NMR (400 MHz, DMSO-d$_6$): δ ppm−0.17 (s, 6H), 0.59 (s, 9H), 1.63 (s, 6H), 3.86 (s, 2H), 3.99 (s, 2H), 7.57 (d, 2H), 7.69 (d, 2H), 8.11 (s, 1H), 8.45 (d, 1H), 8.51 (s, 1H), 8.67 (s, 1H), 8.88 (d, 1H), 9.37 (d, 1H), 10.73 (s, 1H).

LCMS Rt=4.15 minutes MS m/z 629 [M+H]$^+$

Preparation 2

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-chloro-phenyl)-acetamide

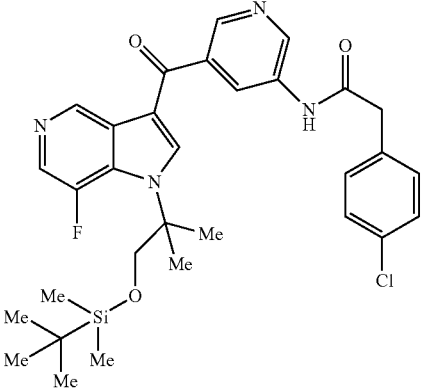 [SMILES: CC(C)(CO[Si](C)(C)C(C)(C)C)n1cc(C(=O)c2cncc(NC(=O)Cc3ccc(Cl)cc3)c2)c2cncc(F)c21]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 70 μmol), (4-chloro-phenyl)-acetic acid (13 mg, 79 μmol) and DIPEA (31 μL, 237 μmol) in THF (3 mL), T3P (151 μL, 237 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as an off white solid (74%, 35 mg).

LCMS Rt=4.02 minutes MS m/z 595 [M+H]$^+$

Preparation 3

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(3-trifluoromethyl-phenyl)-acetamide

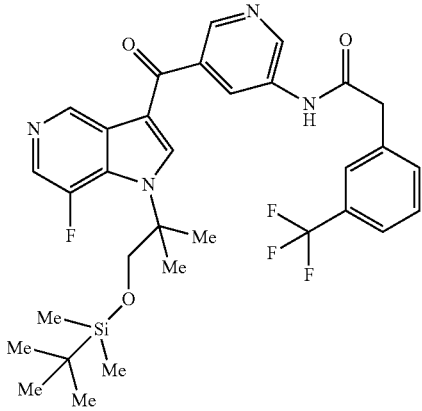 [SMILES: CC(C)(CO[Si](C)(C)C(C)(C)C)n1cc(C(=O)c2cncc(NC(=O)Cc3cccc(C(F)(F)F)c3)c2)c2cncc(F)c21]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79 μmol), (3-trifluoromethyl-phenyl)-acetic acid (21.8 mg, 106 μmol) and DIPEA (48.94 μL, 277 μmol) in THF (3 mL), T3P (160 μL, 277 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as a white solid (87%, 43 mg).

$^1$H NMR (400 MHz, DMSO-d$_6$): δ ppm–0.17 (s, 6H), 0.59 (s, 9H), 1.63 (s, 6H), 3.87 (s, 2H), 3.98 (s, 2H), 7.58 (m, 1H), 7.65 (m, 2H), 7.73 (s, 1H), 8.12 (s, 1H), 8.45 (d, 1H), 8.53 (s, 1H), 8.67 (d, 1H), 8.87 (d, 1H), 9.37 (d, 1H), 10.73 (s, 1H).

LCMS Rt=4.15 minutes MS m/z 629 [M+H]$^+$

Preparation 4

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(4-trifluoromethyl-pyrazol-1-yl)-acetamide

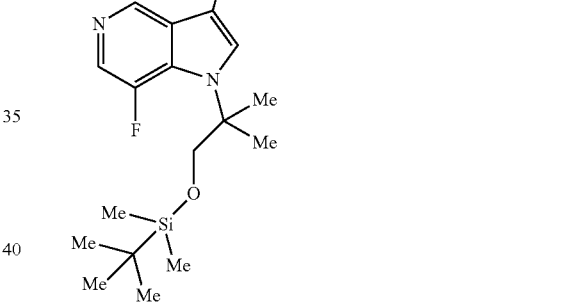

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79.1 μmol), (4-trifluoromethyl-pyrazol-1-yl)-acetic acid (20.7 mg, 106.9 μmol) and DIPEA (48 μL, 276.8 μmol) in THF (3 mL), T3P (166 μL, 276.8 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as an off white solid (71%, 35 mg).

LCMS Rt=3.83 minutes MS m/z 619 [M+H]$^+$

Preparation 5

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(5-chloro-pyridin-2-yl)-acetamide

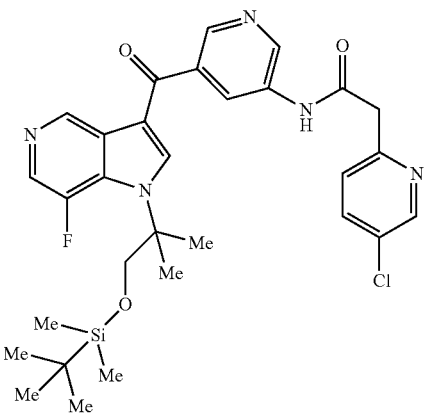 [SMILES: CC(C)(CO[Si](C)(C)C(C)(C)C)n1cc(C(=O)c2cncc(NC(=O)Cc3ccc(Cl)cn3)c2)c2cncc(F)c21]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79.1 μmol), (5-chloro-pyridin-2-yl)-acetic acid (18.8 mg, 106.9 μmol) and DIPEA (48 μL, 276.8 μmol) in THF (3 mL), T3P (0.16 μL, 276.8 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as an off white solid (64%, 30 mg).

LCMS Rt=3.87 minutes MS m/z 596 [M+H]$^+$

Preparation 6

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(3-cyclopropyl-pyrazol-1-yl)-acetamide

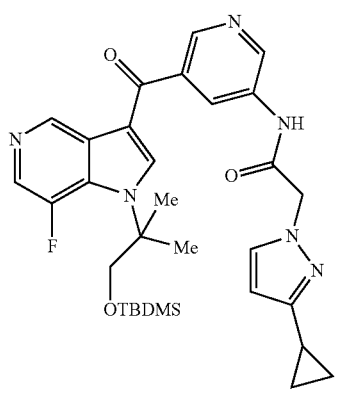 [SMILES: CC(C)(CO[Si](C)(C)C(C)(C)C)n1cc(C(=O)c2cncc(NC(=O)Cn3ccc(C4CC4)n3)c2)c2cncc(F)c21]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79 μmol), (3-cyclopropyl-pyrazol-1-yl)-acetic acid (17.74 mg, 106 μmol) and DIPEA (48.97 μL, 277 μmol) in THF (3 mL), T3P (166 μL, 277 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as an off white solid (91%, 42 mg) that was taken directly on to the next step.

Preparation 7

N-(5-{1-[2-(tert-Butyl-dimethyl-silanyloxy)-1,1-dimethyl-ethyl]-7-fluoro-1H-pyrrolo[3,2-c]pyridine-3-carbonyl}-pyridin-3-yl)-2-(5-methyl-3-trifluoromethyl-pyrazol-1-yl)-acetamide

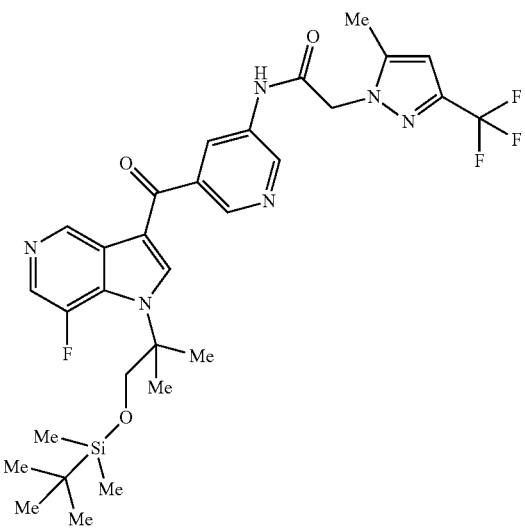 [SMILES: Cc1cc(C(F)(F)F)nn1CC(=O)Nc1cncc(C(=O)c2cn(C(C)(C)CO[Si](C)(C)C(C)(C)C)c3c(F)cncc23)c1]

To a solution of (5-amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone (Preparation 29, 35 mg, 79.1 μmol), (5-methyl-3-trifluoromethyl-pyrazol-1-yl)-acetic acid (22 mg, 106.9 μmol) and DIPEA (48 μL, 276.8 μmol) in THF (3 mL), T3P (166 μL, 276.8 μmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as an off white solid (70%, 37 mg).

LCMS Rt=3.92 minutes MS m/z 633 [M+H]$^+$

Preparation 8

N-(5-{1-[2-(tert-Butyl-dimethyl-silanyloxy)-1,1-dimethyl-ethyl]-1H-pyrrolo[3,2-c]pyridine-3-carbonyl}-pyridin-3-yl)-2-(5-chloro-pyridin-2-yl)-acetamide

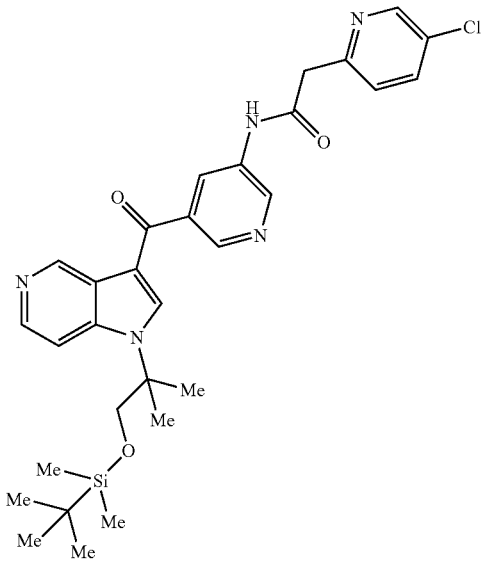 [SMILES: CC(C)(CO[Si](C)(C)C(C)(C)C)n1cc(C(=O)c2cncc(NC(=O)Cc3ccc(Cl)cn3)c2)c2cnccc21]

Method Z

To a solution of (5-amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation 28, 50 mg, 0.117 mmol), (5-chloro-pyridin-2-yl)-acetic acid (30 mg, 0.176 mmol) and DIPEA (72.76 μL, 0.411 mmol) in THF (5 mL), T3P (261.8 μL, 0.411 mmol) was added and the mixture stirred at 25° C. for 18 hours. The reaction was evaporated under reduced pressure, the residue partitioned between water and ethyl acetate, the organic extracts washed with saturated sodium bicarbonate solution, dried over sodium sulphate, evaporated in vacuo and triturated with pentane-ether to afford the title compound as a yellow solid (66%, 45 mg).

LCMS Rt=3.50 minutes MS m/z 578 [M+H]$^+$

Preparation 9

N-(2-{[1-(2-{[tert-butyl(dimethyl)silyl]oxy}-1,1-dimethylethyl)-1H-pyrrolo[3,2-c]pyridin-3-yl]carbonyl}pyridin-4-yl)-2-(4-cyanophenyl)acetamide

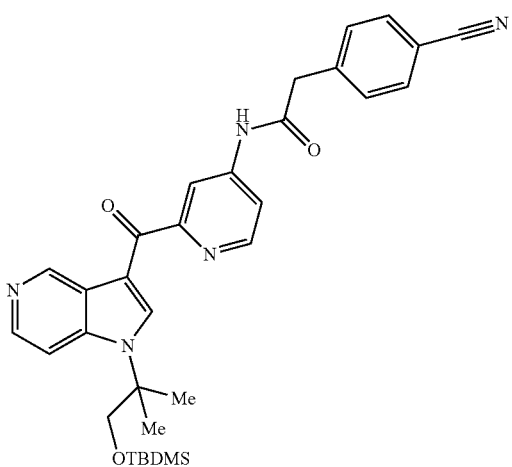 [SMILES: CC(C)(CO[Si](C)(C)C(C)(C)C)n1cc(C(=O)c2cc(NC(=O)Cc3ccc(C#N)cc3)ccn2)c2cnccc21]

Prepared according to the method described for Method M (Example 206) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) and 4-cyanophenylacetic acid. The residue was purified using silca gel column chromatography eluting with EtOAc to afford the title compound that was taken directly on to the next step.

Preparation 10

N-(2-{[1-(2-{[tert-butyl(dimethyl)silyl]oxy}-1,1-dimethylethyl)-1H-pyrrolo[3,2-c]pyridin-3-yl]carbonyl}pyridin-4-yl)-2-[3-(trifluoromethyl)-1H-pyrazol-1-yl]acetamide

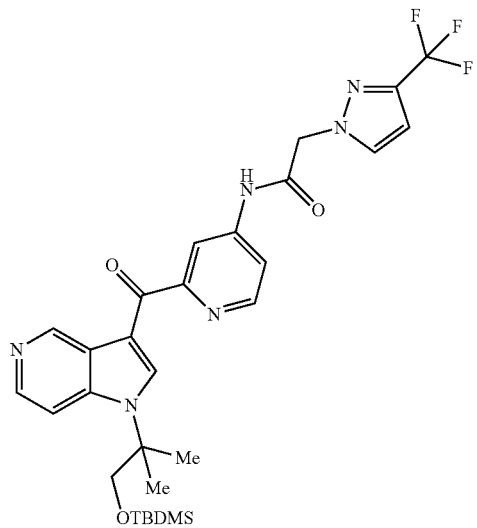 [SMILES: CC(C)(CO[Si](C)(C)C(C)(C)C)n1cc(C(=O)c2cc(NC(=O)Cn3ccc(C(F)(F)F)n3)ccn2)c2cnccc21]

Prepared according to the method described for Method M (Example 206) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) and [3-(trifluoromethyl)-1H-pyrazol-1-yl]acetic acid (Preparation 74). The residue was purified using alumina eluting with 2% MeOH in DCM to afford the title compound.

LCMS (5 minute run) Rt=3.77 minutes MS m/z 601 [M+H]$^+$

Preparation 11

N-(2-{[1-(2-{[tert-butyl(dimethyl)silyl]oxy}-1,1-dimethylethyl)-1H-pyrrolo[3,2-c]pyridin-3-yl]carbonyl}pyridin-4-yl)-2-[4-(trifluoromethyl)-1H-1,2,3-triazol-1-yl]acetamide

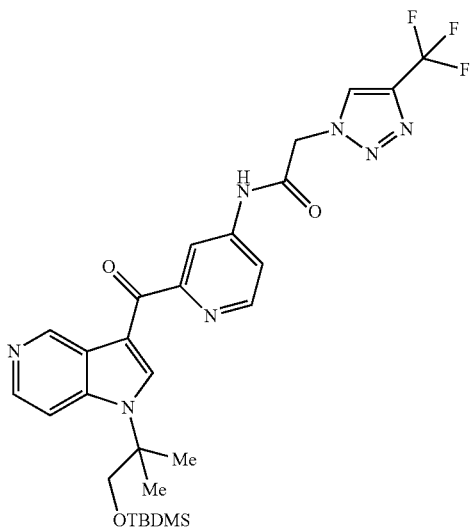 [SMILES: CC(C)(CO[Si](C)(C)C(C)(C)C)n1cc(C(=O)c2cc(NC(=O)Cn3cc(C(F)(F)F)nn3)ccn2)c2cnccc21]

Prepared according to the method described for Method M (Example 206) using (4-aminopyridin-2-yl)[1-(2-{[tert-butyl(dimethyl)silyl]oxy}-1,1-dimethylethyl)-1H-pyrrolo[3,2-c]pyridin-3-yl]methanone (Preparation 27) and [4-(Trifluoromethyl)-1H-1,2,3-triazol-1-yl]acetic acid (Preparation 90). The residue was purified using alumina eluting with 3% MeOH in DCM to afford the title compound.

$^1$HNMR (400 MHz, DMSO-d$_6$): δ ppm −0.17 (s, 6H), 0.65 (s, 9H), 1.71 (s, 6H), 4.00 (s, 2H), 5.58 (s, 2H), 7.82 (d, 1H), 7.87 (d, 1H), 8.23 (s, 1H), 8.33 (d, 1H), 8.64 (d, 1H), 8.94 (s, 1H), 9.11 (s, 1H), 9.59 (s, 1H), 11.18 (s, 1H).

LCMS (5 minute run) Rt=3.78 minutes MS m/z 602 [M+H]$^+$

Preparation 12

N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-cyanophenyl)acetamide

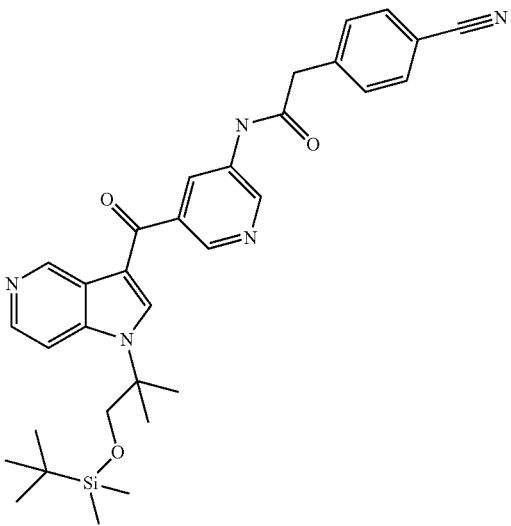 [SMILES: CC(C)(CO[Si](C)(C)C(C)(C)C)n1cc(C(=O)c2cncc(NC(=O)Cc3ccc(C#N)cc3)c2)c2cnccc21]

Prepared according to Method Z (Preparation 8) using (5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation TT) and 4-cyanophenylacetic acid.

LCMS (5 minute run) Rt=3.45 minutes MS m/z 568 [M+H]$^+$

Preparation 13

N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-[4-(trifluoromethyl)-1H-1,2,3-triazol-1-yl]acetamide

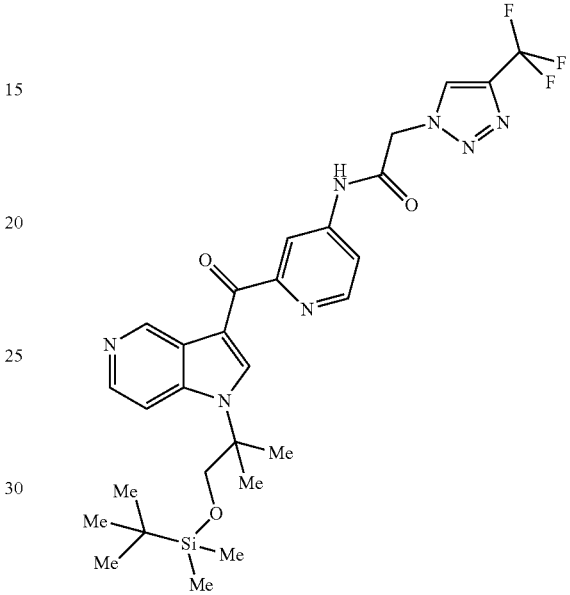

Prepared according to Method Z (Preparation 8) using (5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation 28) and [4-(trifluoromethyl)-1H-1,2,3-triazol-1-yl]acetic acid (Preparation 90).

LCMS (5 minute run) Rt=3.48 minutes MS m/z 602 [M+H]$^+$

Preparation 14

N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-isopropyl-1H-1,2,3-triazol-1-yl)acetamide

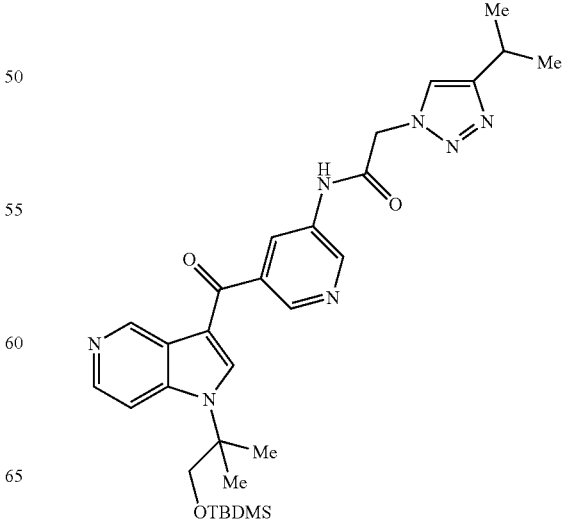

Prepared according to Method Z (Preparation 8) using (5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation 28) and (4-isopropyl-[1,2,3]triazol-1-yl)acetic acid. LCMS (5 minute run) Rt=3.32 minutes MS m/z 576 [M+H]+

Preparation 15

N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(4-cyclopropyl-1H-1,2,3-triazol-1-yl)acetamide

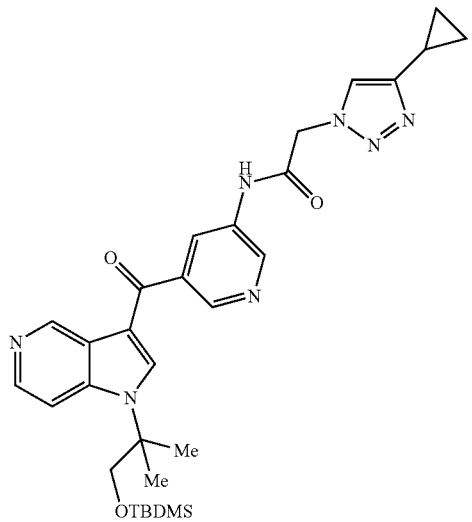 [SMILES: CC(C)(CO[Si](C)(C)C(C)(C)C)n1cc(C(=O)c2cncc(NC(=O)Cn3cc(C4CC4)nn3)c2)c2cnccc21]

Prepared according to Method Z (Preparation 8) using (5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation 28) and 4-(cyclopropyl-1H-1,2,3-triazol-1-yl)acetic acid (Preparation 94).
LCMS (5 minute run) Rt=3.26 minutes MS m/z 574 [M+H]+

Preparation 16

N-(5-{[1-(2-{[tert-butyl(dimethyl)silyl]oxy}-1,1-dimethylethyl)-1H-pyrrolo[3,2-c]pyridin-3-yl]carbonyl}pyridin-3-yl)-2-(5-fluoropyridin-2-yl)acetamide

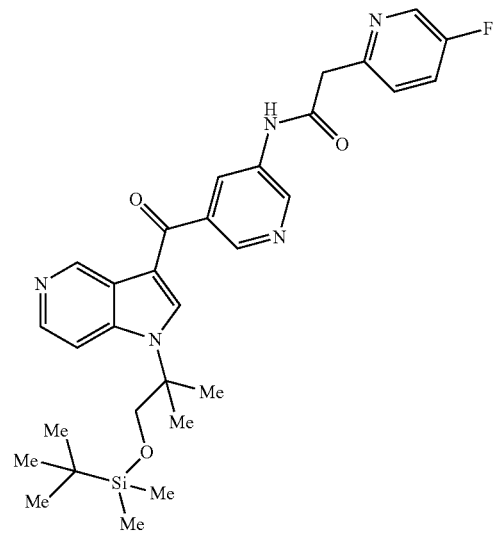 [SMILES: CC(C)(CO[Si](C)(C)C(C)(C)C)n1cc(C(=O)c2cncc(NC(=O)Cc3ccc(F)cn3)c2)c2cnccc21]

Prepared according to Method Z (Preparation 8) using (5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone (Preparation 28) and (5-fluoropyridin-2-yl)acetic acid (Preparation 82).
LCMS (5 minute run) Rt=3.38 minutes MS m/z 562 [M+H]+

Preparation 17 Enantiomer 2

N-(2-{[1-(2-{[tert-butyl(dimethyl)silyl]oxy}-1-methylethyl)-1H-pyrrolo[3,2-c]pyridin-3-yl]carbonyl}pyridin-4-yl)-2-(5-chloropyridin-2-yl)acetamide

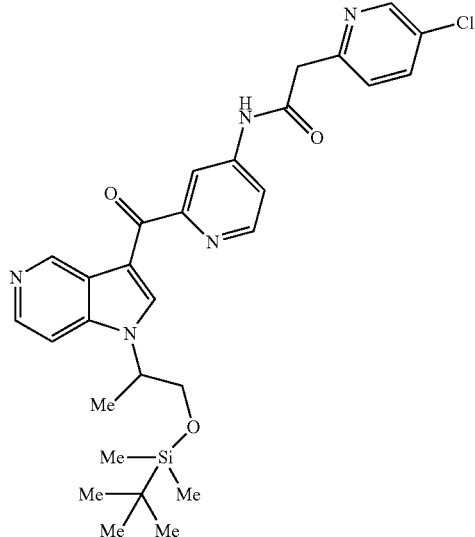 [SMILES: CC(CO[Si](C)(C)C(C)(C)C)n1cc(C(=O)c2cc(NC(=O)Cc3ccc(Cl)cn3)ccn2)c2cnccc21]

Prepared according to Method Z (Preparation 8) using (4-aminopyridin-2-yl)[1-(2-{[tert-butyl(dimethyl)silyl]oxy}-1-methylethyl)-1H-pyrrolo[3,2-c]pyridin-3-yl]methanone (Preparation 30) and (5-chloropyridin-2-yl)acetic acid (Preparation 80).
LCMS (5 minute run) Rt=3.63 minutes MS m/z 564 [M+H]+

Preparation 18 Enantiomer 1

N-(2-{[1-(2-{[tert-butyl(dimethyl)silyl]oxy}-1-methylethyl)-1H-pyrrolo[3,2-c]pyridin-3-yl]carbonyl}pyridin-4-yl)-2[3-(trifluoromethyl)phenyl]acetamide

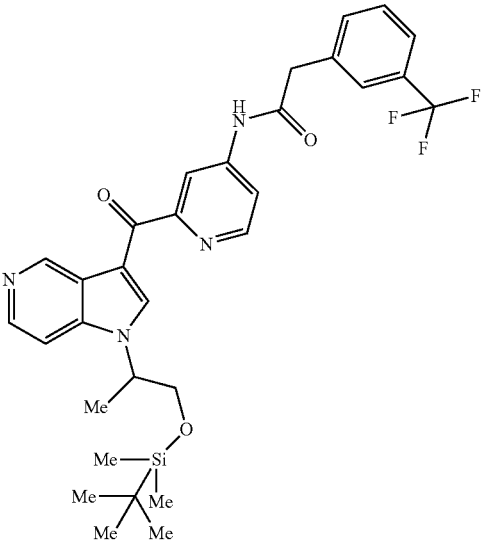 [SMILES: CC(CO[Si](C)(C)C(C)(C)C)n1cc(C(=O)c2cc(NC(=O)Cc3cccc(C(F)(F)F)c3)ccn2)c2cnccc21]

Prepared according to Method Z (Preparation 8) using (4-aminopyridin-2-yl)[1-(2-{[tert-butyl(dimethyl)silyl]oxy}-1-methylethyl)-1H-pyrrolo[3,2-c]pyridin-3-yl]methanone (Preparation 30) and 3-trifluoromethylphenylacetic acid.

LCMS (5 minute run) Rt=3.92 minutes MS m/z 597 [M+H]$^+$

Preparation 19

(5-aminopyridin-3-yl)(1-isopropyl-1H-pyrrolo[3,2-c]pyridin-3-yl)methanone

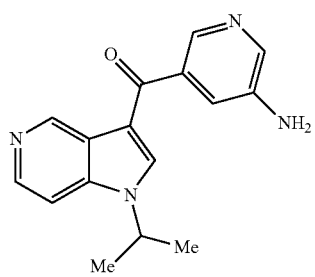 [SMILES: CC(C)n1cc(C(=O)c2cncc(N)c2)c2cnccc21]

To a mixture of (5-bromopyridin-3-yl)(1-isopropyl-1H-pyrrolo[3,2-c]pyridin-3-yl)methanone (Preparation 37, 4.3 g, 12.5 mmol) in aqueous 880 ammonia (65 mL) was added CuSO$_4$.5H$_2$O (936 mg, 3.75 mmol) and the reaction was heated at 130° C. in an autoclave for 18 hours. The reaction was extracted into DCM and the organic layer collected, filtered, dried over sodium sulphate and concentrated in vacuo. The residue was purified through alumina eluting with 1-3% MeOH in DCM to afford the title compound as a white solid (2.1 g, 60%).

$^1$HNMR (400 MHz, DMSO-d$_6$): δ ppm 1.52-1.54 (d, 6H), 4.86-4.92 (m, 1H), 5.62 (s, 2H), 7.27 (s, 1H), 7.74 (d, 1H), 8.15-8.20 (d, 3H), 8.38 (d, 1H), 9.39 (s, 1H).

LCMS (5 minute run) Rt=2.49 minutes MS m/z 281 [M+H]$^+$

Preparation 20

(2-Aminopyridin-4-yl)-(1-isopropyl-1H-pyrrolo[3,2-c]pyridin-3-yl)methanone

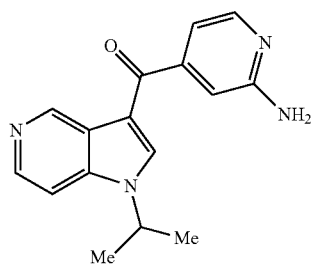 [SMILES: CC(C)n1cc(C(=O)c2ccnc(N)c2)c2cnccc21]

Prepared according to the method described for Preparation 19 using (2-chloropyridin-4-yl)-(1-isopropyl-1H-pyrrolo[3,2-c]pyridin-3-yl)methanone (Preparation 38) at 160° C. The mixture was cooled to room temperature, and then extracted with DCM (500 mL×6). The combined organic phases were washed with brine, dried over Na$_2$SO$_4$ and concentrated under reduced pressure. The residue was purified by silica gel column chromatography eluting with DCM/petroleum ether from 1:10 to 2:1) to afford the title compound as a light yellow solid (6.2 g, 43%).

$^1$HNMR (400 MHz, DMSO-d$_6$): δ ppm 1.50 (d, 6H), 4.84-4.87 (m, 1H), 6.20 (br s, 2H), 6.73 (s, 1H), 6.75 (m, 1H), 7.72 (m, 1H), 8.05 (m, 1H), 8.16 (s, 1H), 8.38 (m, 1H), 9.37 (s, 1H). MS m/z 280 [M]$^+$ Preparation 21

(2-aminopyridin-4-yl){1-[2-(tetrahydro-2H-pyran-2-yloxy)ethyl]-1H-pyrrolo[3,2-c]pyridin-3-yl}methanone

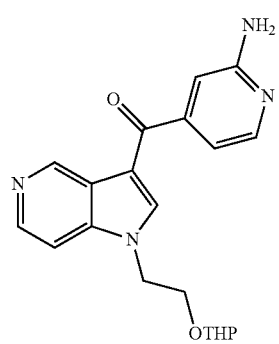

Prepared according to the method described for Preparation 19 using (2-bromopyridin-4-yl){1-[2-(tetrahydro-2H-pyran-2-yloxy)ethyl]-1H-pyrrolo[3,2-c]pyridin-3-yl}methanone (Preparation 40).

$^1$H NMR (400 MHz, DMSO-d$_6$) δ: ppm 1.33-1.50 (m, 5H), 3.23-3.27 (m, 2H), 3.69-3.72 (m, 1H), 3.88-3.93 (m, 1H), 4.50-4.53 (d, 3H), 6.21 (s, 2H), 6.71 (s, 1H), 6.75 (d, 1H), 7.71 (d, 1H), 8.06 (d, 1H), 8.17 (s, 1H), 8.40 (d, 1H), 9.39 (s, 1H).

LCMS (5 minute run) Rt=2.71 minutes MS m/z 367 [M+H]$^+$

Preparation 22

(4-Aminopyridin-2-yl)-(1-isopropyl-1H-pyrrolo[3,2-c]pyridine-3-yl)methanone

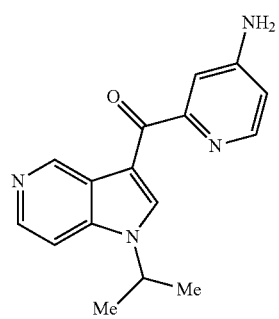 [SMILES: CC(C)n1cc(C(=O)c2cc(N)ccn2)c2cnccc21]

Prepared according to the method described for Preparation 19 using (4-bromopyridin-2-yl)-(1-isopropyl-1H-pyrrolo[3,2-c]pyridine-3-yl)methanone (Preparation 39). The residue was purified using silica gel column chromatography eluting with 60% EtOAc in heptanes to afford the title compound as a light yellow solid (1.4 g, 57%).

¹HNMR (400 MHz, DMSO-d₆): δ ppm 1.52-1.54 (d, 6H), 4.85-4.92 (m, 1H), 6.33 (s, 2H), 6.66-6.67 (m, 1H), 7.22 (s, 1H), 7.70-7.72 (d, 1H), 8.18 (d, 1H), 8.35 (d, 1H), 9.05 (s, 1H), 9.52 (s, 1H).

LCMS Rt=2.49 minutes MS m/z 280 [M]⁺

Preparation 23

(5-aminopyridin-3-yl)(7-fluoro-1-isopropyl-1H-pyrrolo[3,2-c]pyridin-3-yl)methanone

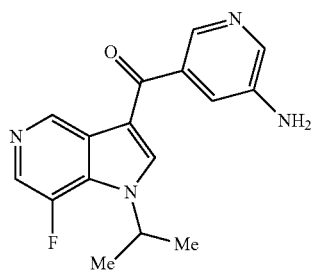 [SMILES: CC(C)n1cc(C(=O)c2cncc(N)c2)c2cncc(F)c21]

Prepared according to the method described for Preparation 27 using {5-[(diphenylmethylene)amino]pyridin-3-yl}(7-fluoro-1-isopropyl-1H-pyrrolo[3,2-c]pyridin-3-yl)methanone (Preparation 34). Taken on directly to the next step.

Preparation 24

(2-Aminopyridin-4-yl)-(1-(oxetan-3-yl)-1H-pyrrolo[3,2-c]pyridin-3-yl)methanone

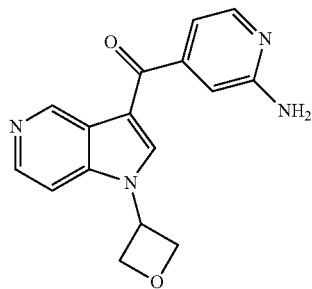 [SMILES: Nc1cc(C(=O)c2cn(C3COC3)c3ccncc23)ccn1]

Isopropyl magnesium chloride (8.16 mL, 1.28 mmol, 2M in diethyl ether) was added to 3-iodo-1-(oxetan-3-yl)-1H-pyrrolo[3,2-c]pyridine (Preparation 53, 4.45 g, 14.8 mmol) in THF (90 mL) at 0° C., under nitrogen. The mixture was stirred at 0° C. for 1 hour then a solution of 2-[(diphenylmethylene)amino]-N-methoxy-N-methylisonicotinamide (Preparation 51, 5.12 g, 14.8 mmol) in THF (30 mL) was added dropwise at 0° C. The mixture was warmed to room temperature and stirred at this temperature for 16 hours. The reaction mixture was quenched with water (200 mL) and extracted with DCM/MeOH 95:5 (7×100 mL). The combined organic extracts were washed with brine, dried over magnesium sulphate and evaporated in vacuo. The residue was purified using silica gel column chromatography eluting with 0-5% MeOH in DCM followed by a second purification by silica gel column chromatography eluting with 30-50% EtOAc in DCM. The residue was dissolved in THF (90 mL) and 0.5M HCl (90 mL) was added followed by stirring at room temperature for 30 minutes. The reaction was quenched by the addition of 1N NaOH to pH 6-7 and the mixture eluted through an SCX cartridge washing through with MeOH followed by ammonia in MeOH (300 mL, 2M solution). The filtrate was concentrated in vacuo, azeotroping with toluene. The residue was dissolved in DCM:MeOH 90:10 (20 mL) and poured into diethyl ether (1000 mL) to precipitate a white solid. After filtering the white solid was dried to afford the title compound.

¹H NMR (400 MHz, DMSO-d₆): δ ppm 4.98-5.08 (m, 4H), 5.92-6.00 (m, 1H), 6.95 (m, 1H), 7.06 (m, 1H), 7.25 (br s, 2H), 8.04 (m, 1H), 8.11 (m, 1H), 8.58 (m, 1H), 8.74 (s, 1H), 9.48 (s, 1H).

Preparation 25

(5-aminopyridin-3-yl)[1-(2-hydroxy-1-methylethyl)-1H-pyrrolo[3,2-c]pyridin-3-yl]methanone

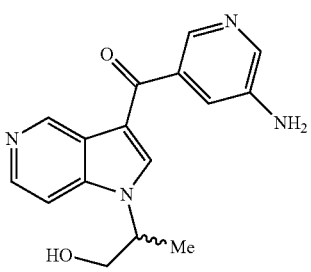
Enantiomer 1

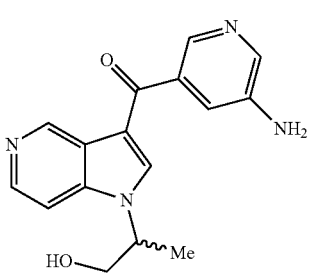
Enantiomer 2

To a solution of [1-(2-{[tert-butyl(dimethyl)silyl]oxy}-1-methylethyl)-1H-pyrrolo[3,2-c]pyridin-3-yl]{5-[(diphenylmethylene)amino]pyridin-3-yl}methanone (Enantiomer 1, Preparation 33, 150 mg, 0.260 mmol) in DCM (5 mL) was added TFA (0.2 mL) and the reaction stirred at room temperature for 4 hours. The reaction was purified directly by preparative HPLC to afford the title compound (40 mg, 52%).

¹H NMR (400 MHz, DMSO-d₆): δ ppm 1.50 (d, 3H), 3.70-3.80 (m, 2H), 4.75 (m, 1H), 5.10 (br s, 1H), 5.60 (s, 2H), 7.27 (s, 1H), 7.72 (d, 1H), 8.15 (m, 3H), 8.37 (d, 1H), 9.40 (s, 1H).

Enantiomer 2 was prepared in the same manner as Enantiomer 1.

Preparation 26

(5-aminopyridin-3-yl)[7-fluoro-1-(2-hydroxy-1-methylethyl)-1H-pyrrolo[3,2-c]pyridin-3-yl]methanone Enantiomer 1

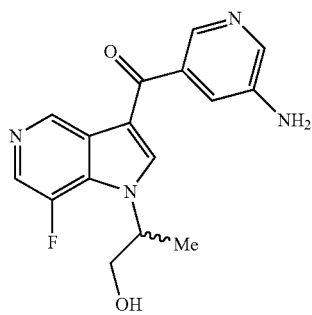

Enantiomer 2

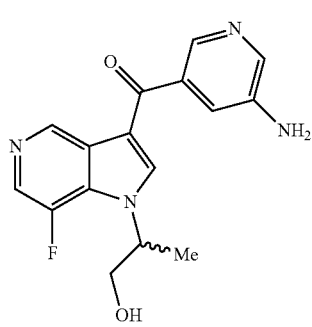

Prepared according to the method described for Preparations 19 and 37 using 1-(2-{[tert-butyl(dimethyl)silyl]oxy}-1-methylethyl)-7-fluoro-3-iodo-1H-pyrrolo[3,2-c]pyridine (Enantiomer 1, Preparation 58) in NMP.

Enantiomer 2 was prepared in the same manner as Enantiomer 1.

$^1$H NMR (400 MHz, DMSO-d$_6$): δ ppm 1.50 (d, 3H), 3.72-3.79 (m, 2H), 4.88 (m, 1H), 5.07 (t, 1H), 5.64 (s, 2H), 7.28 (s, 1H), 8.16 (s, 2H), 8.24 (s, 1H), 8.36 (s, 1H), 9.25 (s, 1H).

Preparation 27

(4-aminopyridin-2-yl)[1-(2-{[tert-butyl(dimethyl)silyl]oxy}-1,1-dimethylethyl)-1H-pyrrolo[3,2-c]pyridin-3-yl]methanone

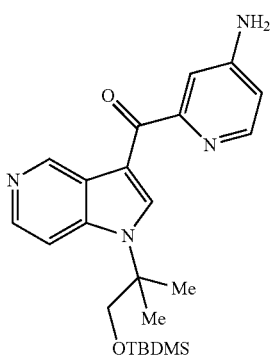

To a solution of [1-(2-{[tert-butyl(dimethyl)silyl]oxy}-1,1-dimethylethyl)-1H-pyrrolo[3,2-c]pyridin-3-yl]{4-[(diphenylmethylene)amino]pyridin-2-yl}methanone (Preparation 35, 1.4 g, 2.38 mmol) in THF (3 mL) was added a 1M solution of citric acid (2.5 g, 11.9 mmol) and the reaction was stirred at room temperature for 4 hours. A 10% aqueous solution of potassium carbonate was added carefully, and the mixture extracted into EtOAc (3×50 mL). The organic layers were combined, dried over MgSO$_4$ and concentrated in vacuo. To the residue was added DCM and a solid precipitated that was filtered and dried. The mother liquors were purified using silica gel column chromatography eluting with 100% heptanes to 100% EtOAc to 5% MeOH in EtOAc to afford further material. The solids were combined to afford the title compound (70%, 710 mg).

$^1$H NMR (400 MHz, DMSO-d$_6$): δ ppm −0.15 (s, 6H), 0.69 (s, 9H), 1.72 (s, 6H), 4.01 (s, 2H), 6.32 (bs, 2H), 6.68 (dd, 1H), 7.23 (d, 1H), 7.87 (d, 1H), 8.16 (d, 1H), 8.33 (d, 1H), 9.15 (s, 1H), 9.60 (s, 1H).

LCMS (2 minute run) Rt=0.74 minutes MS m/z 425 [M+H]$^+$

Preparation 28

(5-Amino-pyridin-3-yl)-{1-[2-(tert-butyl-dimethyl-silanyloxy)-1,1-dimethyl-ethyl]-1H-pyrrolo[3,2-c]pyridin-3-yl}-methanone

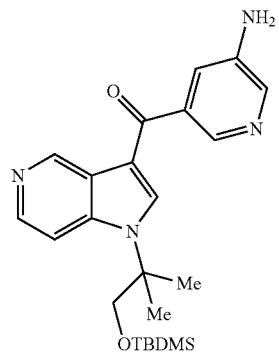 [SMILES: CC(C)(CO[Si](C)(C)C(C)(C)C)n1cc(C(=O)c2cncc(N)c2)c2cnccc21]

To a solution of (5-bromopyridin-3-yl)[1-(2-{[tert-butyl(dimethyl)silyl]oxy}-1,1-dimethylethyl)-1H-pyrrolo[3,2-c]pyridin-3-yl]methanone (Preparation 43, 643 mg, 1.32 mmol) in NMP (1 mL) was added Cu$_2$O (18.9 mg, 0.132 mmol) and 880 ammonia (6 mL) and the reaction heated to 80° C. in a Reactivial™ for 18 hours followed by an additional 18 hours at 90° C. The reaction was cooled and partitioned between water (15 mL) and EtOAc (20 mL). The aqueous layer was extracted twice with EtOAc (2×20 mL), the organic layers combined, dried and concentrated in vacuo. The residue was purified using silica gel column chromatography eluting with 50:50 DCM:EtOAc to 80:20 EtOAc:MeOH to afford the title compound as a yellow gum (320 mg, 57%).

$^1$H NMR (400 MHz, CDCl$_3$): δ ppm 0.00 (s, 6H), 0.80 (s, 9H), 1.80 (s, 6H), 2.50 (m, 1H), 3.50 (m, 1H), 4.05 (s, 2H), 7.55 (m, 1H), 7.65 (br s, 1H), 8.00 (s, 1H), 8.40 (br m, 1H), 8.55 (br s, 1H), 9.80 (br s, 1H).

Preparation 29

(5-Amino-pyridin-3-yl)-{1-[2-(tert-butyl-dimethyl-silanyloxy)-1,1-dimethyl-ethyl]-7-fluoro-1H-pyrrolo[3,2-c]pyridin-3-yl}-methanone

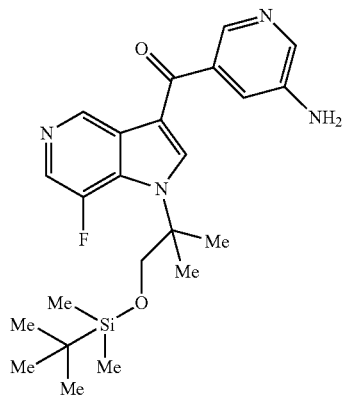 [SMILES: CC(C)(CO[Si](C)(C)C(C)(C)C)n1cc(C(=O)c2cncc(N)c2)c2cncc(F)c21]

To a solution of [5-(benzhydrylidene-amino)-pyridin-3-yl]-{1-[2-(tert-butyl-dimethyl-silanyloxy)-1,1-dimethyl-ethyl]-7-fluoro-1H-pyrrolo[3,2-c]pyridin-3-yl}-methanone (Preparation 36, 1 g, 1.65 mmol) in THF (80 mL), citric acid (30 mL, 1 M) was added at room temperature and stirred for 4 hours, then quenched with saturated sodium bicarbonate solution and was extracted with ethyl acetate. The organic phase was dried over sodium sulphate, evaporated in vacuo to afford the crude compound, purified by column chromatography over alumina (gradient of DCM: Methanol 98:2 to 97:3) to afford the title compound as a pale yellow solid (69%, 500 mg).

$^1$H NMR (400 MHz, DMSO-d$_6$): δ ppm 0.01 (s, 6H), 0.61 (s, 9H), 1.66 (s, 6H), 4.01 (s, 2H), 5.71 (s, 2H), 7.22 (s, 1H), 8.00 (s, 1H), 8.10 (s, 2H), 8.60 (s, 1H), 9.30 (s, 1H).

LCMS Rt=3.58 minutes MS m/z 443 [M+H]$^+$

Preparation 30

(4-aminopyridin-2-yl)[1-(2-{[tert-butyl(dimethyl)silyl]oxy}-1-methylethyl)-1H-pyrrolo[3,2-c]pyridin-3-yl]methanone Enantiomer 1

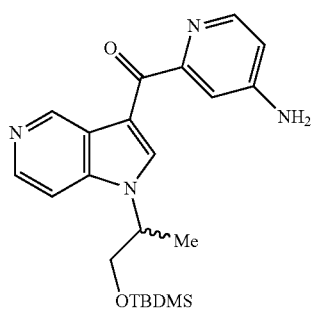

Enantiomer 2

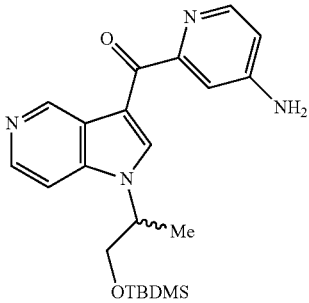

Prepared according to the method described for Preparation 19 using (4-bromopyridin-2-yl)[1-(2-{[tert-butyl(dimethyl)silyl]oxy}-1-methylethyl)-1H-pyrrolo[3,2-c]pyridin-3-yl]methanone (Enantiomer 1, Preparation 42) at 100° C. for 20 hours. Purified using silica gel column chromatography eluting with 6-8% MeOH in DCM. The residue was then re-protected as the TBDMS ether according to the method described for Preparation 55. The residue was purified using silica gel column chromatography eluting with 80-90% EtOAc in hexane.

Enantiomer 2 was prepared in the same manner as Enantiomer 1.

LCMS (5 minute run) Rt=3.37 minutes MS m/z 411 [M+H]$^+$

Preparation 31

(5-amino-6-methoxypyridin-3-yl)(1-isopropyl-1H-pyrrolo[3,2-c]pyridin-3-yl)methanone

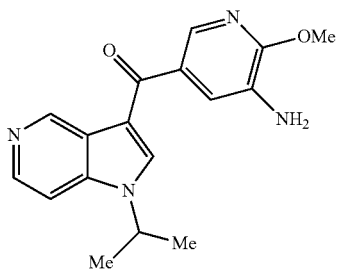 [SMILES: COc1ncc(C(=O)c2cn(C(C)C)c3ccncc23)cc1N]

To a solution of di-tert-butyl {5-[(1-isopropyl-1H-pyrrolo[3,2-c]pyridin-3-yl)carbonyl]-2-methoxypyridin-3-yl}imidodicarbonate (Preparation 32, 250 mg, 0.5 mmol) in DCM (2.5 mL) at 0° C. was added TFA (0.75 mL) dropwise and the reaction stirred warming to room temperature for 5 hours. The reaction was basified by the addition of saturated aqueous NaHCO$_3$ solution and extracted into DCM (3×30 mL). The organic layers were combined, dried over sodium sulphate and concentrated in vacuo. The residue was purified using silica gel column chromatography eluting with 5% MeOH in DCM to afford the title compound.

¹H NMR (400 MHz, DMSO-d₆): δ ppm 1.54 (d, 6H), 3.99 (s, 3H), 4.87 (m, 1H), 5.26 (s, 2H), 7.31 (d, 1H), 7.73 (m, 1H), 7.93 (d, 1H), 8.23 (d, 1H), 8.37 (m, 1H), 9.37 (s, 1H).

Preparation 32 di-tert-butyl {5-[(1-isopropyl-1H-pyrrolo[3,2-c]pyridin-3-yl)carbonyl]-2-methoxypyridin-3-yl}imidodicarbonate

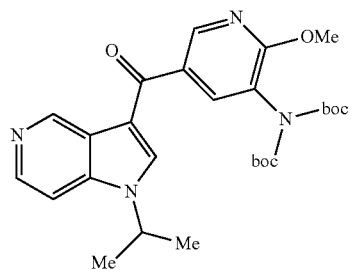

To a solution of 3-iodo-1-isopropyl-1H-pyrrolo[3,2-c]pyridine (Preparation 45, 250 mg, 0.875 mmol) in ether (5 mL) at −78° C. was added nBuLi (2.3M in hexane, 0.38 mL, 0.875 mmol) and the reaction stirred at this temperature for 30 minutes. A solution of di-tert-butyl {2-methoxy-5-[methoxy(methyl)carbamoyl]pyridin-3-yl}imidodicarbonate (Preparation 69, 300 mg, 0.729 mmol) in ether (2 mL) was added and the reaction continued to stir at this temperature for another 30 minutes. The reaction was warmed to room temperature for 2 hours before being quenched by the addition of saturated ammonium chloride solution. The reaction was extracted into EtOAc (3×15 mL), the combined organic layers were washed with water (15 mL), brine (15 mL), dried over sodium sulphate and concentrated in vacuo. The residue was purified using preparative TLC eluting with EtOAc:DCM 50:50 to afford the title compound and taken on to the next step directly.

Preparation 33

(R) and (S)-[1-(2-{[tert-butyl(dimethyl)silyl]oxy}-1-methylethyl)-1H-pyrrolo[3,2-c]pyridin-3-yl]{5-[(diphenylmethylene)amino]pyridin-3-yl}methanone Enantiomer 1

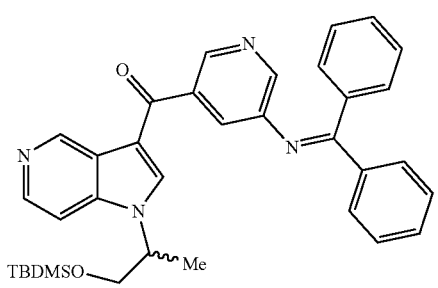

Enantiomer 2

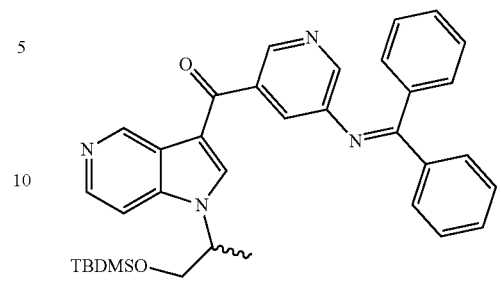

To a solution of (5-bromopyridin-3-yl)[1-(2-{[tert-butyl(dimethyl)silyl]oxy}-1-methylethyl)-1H-pyrrolo[3,2-c]pyridin-3-yl]methanone (Enantiomer 1, Preparation 41, 3.2 g, 0.067 mol) in toluene (90 mL) was added tBuXphos (785 mg, 0.0018 mol), NaOtBu (605 mg, 0.0018 mol), benzophenone imine (1.34 g, 0.0074 mol) and Pd₂(dba)₃ and the reaction was stirred at room temperature for 18 hours. The reaction was filtered through celite and the filtrate extracted into EtOAc. The organic layer was collected, washed with brine, dried over sodium sulphate and concentrated in vacuo. The residue was purified using silica gel column chromatography eluting with 50% EtOAc in heptanes to afford the title compound (1.3 g, 33%).

¹H NMR (400 MHz, DMSO-d₆): δ ppm −0.22 (m, 6H), 0.62 (s, 9H), 1.53 (m, 3H), 3.92 (m, 2H), 4.86 (m, 1H), 7.26 (m, 2H), 7.38 (m, 3H), 7.51 (m, 3H), 7.58 (m, 1H), 7.72 (m, 3H), 8.09 (s, 1H), 8.19 (m, 1H), 8.39 (m, 1H), 8.50 (m, 1H), 9.36 (s, 1H).

Enantiomer 2 was prepared in the same manner as Enantiomer 1.

Example 34

{5-[(diphenylmethylene)amino]pyridin-3-yl}(7-fluoro-1-isopropyl-1H-pyrrolo[3,2-c]pyridin-3-yl)methanone

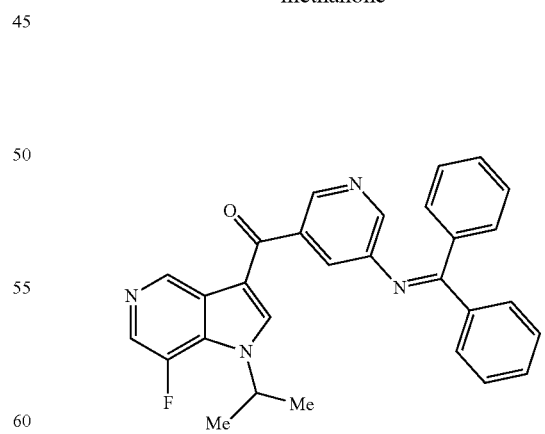

Prepared according to the method described for Preparation 36 using 3-bromo-7-fluoro-1-isopropyl-1H-pyrrolo[3,2-c]pyridine (Preparation 46) and 5-[(diphenylmethylene)amino]-N-methoxy-N-methylnicotinamide (Preparation 52). Taken on directly to the next step.

Preparation 35

[1-(2-{[tert-butyl(dimethyl)silyl]oxy}-1,1-dimethyl-ethyl)-1H-pyrrolo[3,2-c]pyridin-3-yl]{4-[(diphenyl-methylene)amino]pyridin-2-yl}methanone

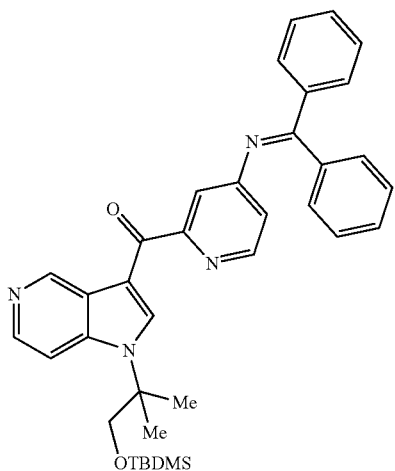 [SMILES: CC(C)(CO[Si](C)(C)C(C)(C)C)n1cc(C(=O)c2cc(N=C(c3ccccc3)c3ccccc3)ccn2)c2cnccc21]

To a suspension of NaOtBu (500 mg, 5.2 mmol) and [1-(2-{[tert-butyl(methyl)silyl]oxyl}-1,1-dimethylethyl)-1H-pyrrolo[3,2-c]pyridin-3-yl](4-chloropyridin-2-yl)methanone (Preparation 44, 1.65 g, 3.71 mmol) in DME (5 mL) was added a solution of palladium acetate (41.8 mg, 0.186 mmol) and (R)-1-[(SP)-2-(dicyclohexylphosphino)ferrocenyl]ethyldi-tert-butylphosphine (103 mg, 0.186 mmol) in DME (2 mL) followed by a solution of benzophenone imine (808 mg, 4.46 mmol) in DME (2 mL). The reaction was degassed and heated to 80° C. for 30 minutes. The reaction was cooled, filtered through celite and partitioned between EtOAc and water. The organic layer was collected, dried over MgSO$_4$ and concentrated in vacuo. The residue was purified using silica gel column chromatography eluting with 100% heptanes to 100% EtOAc to afford the title compound as a brown oil (1.4 g, 64%).

LCMS (2 minute run) Rt=1.26 minutes MS m/z 589 [M+H]$^+$

Preparation 36

[5-(Benzhydrylidene-amino)-pyridin-3-yl]-{1-[2-(tert-butyl-dimethyl-silanyloxy)-1,1-dimethyl-ethyl]-7-fluoro-1H-pyrrolo[3,2-c]pyridin-3-yl}-methanone

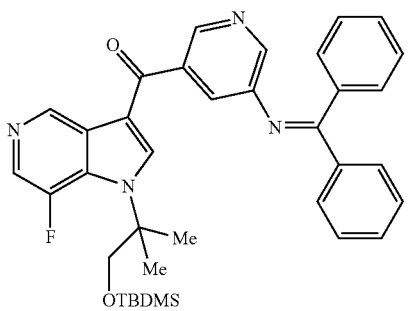 [SMILES: CC(C)(CO[Si](C)(C)C(C)(C)C)n1cc(C(=O)c2cncc(N=C(c3ccccc3)c3ccccc3)c2)c2cncc(F)c21]

To a stirring solution of 1-[2-(tert-Butyl-dimethyl-silyloxy)-1,1-dimethyl-ethyl]-7-fluoro-3-iodo-1H-pyrrolo[3,2-c]pyridine (Preparation 73, 3 g, 6.69 mmol) in dry ether (100 mL) at −78° C., n-BuLi (3.9 mL, 1.84M, 7.17 mmol) was added and stirred for 30 minutes. Then 5-(benzhydrylidene-amino)-N-methoxy-N-methyl-nicotinamide (Preparation 52, 2.31 g, 6.69 mmol) in dry ether (10 mL) was added drop wise for 5 min. After 1 hr reaction mixture was quenched with saturated aqueous solution of ammonium chloride and extracted with ethyl acetate. The organic phase was dried over sodium sulphate and evaporated in vacuo to afford the crude compound, purified by silica gel column chromatography eluting with Ethyl acetate: Hexane 30:70 to 35:65 to afford the title compound as a light red solid (25%, 1 g).

$^1$H NMR (400 MHz, DMSO-d$_6$): δ ppm 0.01 (s, 6H), 0.91 (s, 9H), 1.61 (s, 6H), 4.01 (s, 2H), 6.90 (s, 2H), 7.30 (d, 3H), 7.50 (s, 2H), 7.62 (s, 2H), 7.85 (d, 2H), 8.01 (d, 1H), 8.20 (s, 1H), 8.53 (d, 1H), 8.60 (d, 1H); 9.32 (s, 1H).

LCMS Rt=2.77 minutes MS m/z 607 [M+H]$^+$

Preparation 37

(5-bromopyridin-3-yl)(1-isopropyl-1H-pyrrolo[3,2-c]pyridin-3-yl)methanone

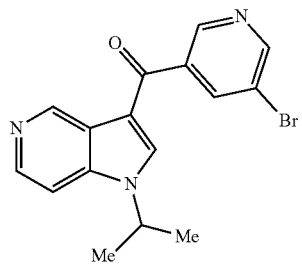 [SMILES: CC(C)n1cc(C(=O)c2cncc(Br)c2)c2cnccc21]

To a mixture of 3-iodo-1-isopropyl-1H-pyrrolo[3,2-c]pyridine (Preparation 45, 13 g, 45.43 mmol) in anhydrous diethyl ether (120 mL) at −78° C. was added nBuLi (28.69 mL, 54.5 mmol) dropwise under nitrogen. After stirring at this temperature for 30 minutes, 5-bromo-N-methoxy-N-methylnicotinamide (11.13 g, 45.43 mmol) in diethylether (10 mL) was added dropwise before warming the reaction to room temperature for 18 hours. The reaction was quenched by the addition of saturated aqueous ammonium chloride solution, extracted into EtOAc, the organic layer collected, dried over Na$_2$SO$_4$ and concentrated in vacuo. The residue was purified using silica gel column chromatography eluting with 80-90% EtOAc in hexanes to afford the title compound as a yellow solid.

$^1$HNMR (400 MHz, DMSO-d$_6$): δ ppm 1.52-1.54 (m, 6H), 4.86-4.93 (m, 1H), 7.77 (d, 1H), 8.35-8.42 (m, 3H), 8.96 (s, 2H), 9.42 (s, 1H).

LCMS (5 minute run) Rt=1.59 minutes MS m/z 344 [M+H]$^+$

Preparation 38

(2-Chloropyridin-4-yl)-(1-isopropyl-1H-pyrrolo[3,2-c]pyridin-3-yl)methanone

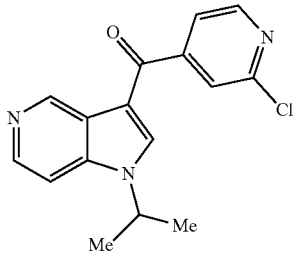 [SMILES: CC(C)n1cc(C(=O)c2ccnc(Cl)c2)c2cnccc21]

To a mixture of (2-chloropyridin-4-yl)-(1H-pyrrolo[3,2-c]pyridin-3-yl)methanone (Preparation 49, 34 g, 0.13 mol) in DMF (700 mL) was added $Cs_2CO_3$ (65 g, 0.2 mol) and 2-iodopropane (34 g, 0.2 mol) at room temperature and the reaction stirred for 18 hours. The solvent was removed under reduced pressure and the residue was purified by silica gel column chromatography eluting with petroleum ether/ethyl acetate from 10:1 to 1:1 to afford the title compound as a yellow solid (7.7 g, 23.6%).

$^1$HNMR (400 MHz, CDCl$_3$): δ ppm 1.62 (d, 6H), 4.75 (m, 1H), 7.38 (m, 1H), 7.53 (m, 1H), 7.63 (s, 1H), 7.67 (s, 1H), 8.50 (m, 1H), 8.56 (m, 1H), 9.56 (s, 1H).

Preparation 39

(4-Bromopyridin-2-yl)-(1-isopropyl-1H-pyrrolo[3,2-c]pyridine-3-yl)methanone

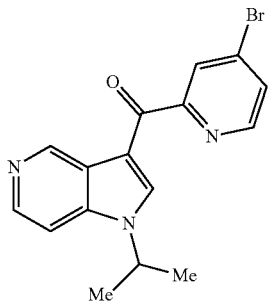 [SMILES: CC(C)n1cc(C(=O)c2cc(Br)ccn2)c2cnccc21]

Prepared according to the method described for Preparation 37 using 4-bromo-N-methoxy-N-methyl pyridine-2-carboxamide.

$^1$HNMR (400 MHz, DMSO-d$_6$): δ ppm 1.54-1.57 (d, 6H), 4.90-4.94 (m, 1H), 7.76 (d, 1H), 7.96 (dd, 1H), 8.22 (d, 1H), 8.40 (d, 1H), 8.70 (d, 1H), 8.98 (s, 1H), 9.5 (s, 1H).

LCMS (5 minute run) Rt=3.64 minutes MS m/z 344 [M+H]$^+$

Preparation 40

(2-bromopyridin-4-yl){1-[2-(tetrahydro-2H-pyran-2-yloxy)ethyl]-1H-pyrrolo[3,2-c]pyridin-3-yl}methanone

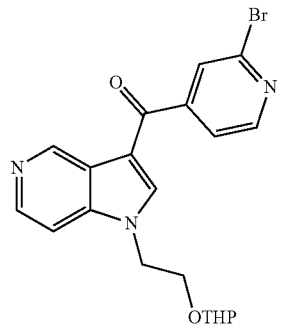

Prepared according to the method described for Preparation 37 using 2-bromo-N-methoxy-N-methylisonicotinamide and 3-iodo-1-[2-(tetrahydro-2H-pyran-2-yloxy)ethyl]-1H-pyrrolo[3,2-c]pyridine (Preparation 50).

$^1$H NMR (400 MHz, CDCl$_3$) δ: ppm 1.43-1.50 (m, 3H), 1.67 (m, 3H), 3.36-3.41 (m, 1H), 3.47-3.53 (m, 1H), 3.72-3.77 (m, 1H), 4.07 (m, 1H), 4.11-4.51 (m, 3H), 7.36 (d, 1H), 7.58 (m, 1H), 7.72 (s, 1H), 7.80 (s, 1H), 8.53 (t, 2H), 9.63 (s, 1H).

Preparation 41

(R) and (S)-(5-bromopyridin-3-yl)[1-(2-{[tert-butyl(dimethyl)silyl]oxy}-1-methylethyl)-1H-pyrrolo[3,2-c]pyridin-3-yl]methanone Enantiomer 1

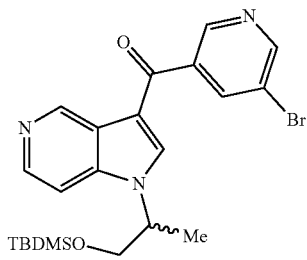

Enantiomer 2

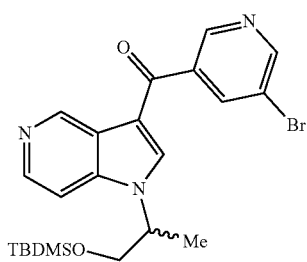

To a solution of 1-(2-{[tert-butyl(dimethyl)silyl]oxy}-1-methylethyl)-3-iodo-1H-pyrrolo[3,2-c]pyridine (Preparation 55, 16 g, 38.6 mmol) in THF (340 mL) was added iPrMgCl (23.2 mL, 46.3 mmol, 2M solution in THF) dropwise at 0° C. After stirring at this temperature for 1 hour, a solution of 5-bromo-N-methoxy-N-methylnicotinamide (11.4 g, 46.3 mmol) in THF (40 mL) was added slowly to the reaction. The reaction was warmed at room temperature and stirred for 18 hours. The reaction was quenched by the addition of water (200 mL) and the solvents removed in vacuo. The residue was diluted with water (400 mL), extracted into DCM:MeOH (95:5, 200 mL)) five times, the organic layers collected, washed with brine, dried over MgSO$_4$ and concentrated in vacuo. The residue was purified using silica gel column chromatography eluting with a gradient of 10-50% EtOAc in DCM to afford the title compound (18.3 g, 46.5%).

$^1$H NMR (400 MHz, CDCl$_3$): δ ppm −0.10 (s, 6H), 0.75 (s, 9H), 1.60 (d, 3H), 3.80-3.95 (m, 2H), 4.60-4.75 (m, 1H), 7.35 (m, 1H), 7.80 (s, 1H), 8.25 (s, 1H), 8.50 (d, 1H), 8.85 (s, 1H), 8.95 (s, 1H), 9.63 (s, 1H).

The racemate was separated using the preparative chiral HPLC method in Preparation 42 to afford the separate enantiomers.

Peak 1=Enantiomer 1
Peak 2=Enantiomer 2

Preparation 42

(4-bromopyridin-2-yl)[1-(2-{[tert-butyl(dimethyl)silyl]oxy}-1-methylethyl)-1H-pyrrolo[3,2-c]pyridin-3-yl]methanone

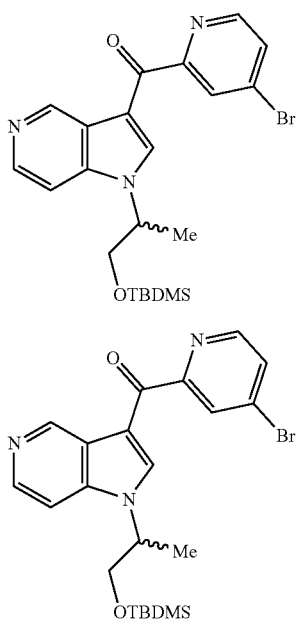

Enantiomer 1

Enantiomer 2

Prepared according to the method described for Preparation 37 using 1-(2-{[tert-butyl(dimethyl)silyl]oxy}-1-methylethyl)-3-iodo-1H-pyrrolo[3,2-c]pyridine (Preparation 55) and 4-bromo-N-methoxy-N-methylpyridine-2-carboxamide. Purified using silica gel column chromatography eluting with 35-40% EtOAc in hexane.

$^1$H NMR (400 MHz, DMSO-d$_6$): δ ppm −0.18 (s, 6H), 0.67 (s, 9H), 1.54 (d, 3H), 3.89 (d, 2H), 4.89-4.93 (m, 1H), 7.73 (d, 1H), 7.96 (m, 1H), 8.22 (d, 1H), 8.39 (d, 1H), 8.64 (d, 1H), 9.00 (s, 1H), 9.53 (s, 1H).

The racemate was separated using preparative chiral HPLC (CHIRALPAK IC 4.6×250 mmm 5 um, eluting with hexane: EtOH:DEA 80:20:0.1 at a flow rate of 1 mL/min to afford the separate enantiomers.

Peak 1=Enantiomer 1
Peak 2=Enantiomer 2

Preparation 43

(5-bromopyridin-3-yl)[1-(2-{[tert-butyl(dimethyl)silyl]oxy}-1,1-dimethylethyl)-1H-pyrrolo[3,2-c]pyridin-3-yl]methanone

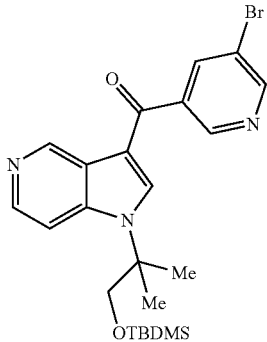 [SMILES: CC(C)(CO[Si](C)(C)C(C)(C)C)n1cc(C(=O)c2cncc(Br)c2)c2cnccc21]

1-(2-{[tert-butyl(dimethyl)silyl]oxy}-1,1-dimethylethyl)-3-iodo-1H-pyrrolo[3,2-c]pyridine (Preparation 65, 1.81 g, 4.20 mmol) was dissolved in THF (25 mL) and the solution was degassed and cooled to −5° C. 2M $^i$PrMgCl in THF (2.52 mL, 5.05 mmol) was added dropwise and the reaction stirred at this temperature for 45 minutes. A solution of 5-bromo-N-methoxy-N-methylnicotinamide (1.24 g, 5.05 mmol) in THF (3 mL) was added dropwise and the reaction warmed to room temperature for 4.5 hours. The reaction was partitioned between saturated aqueous ammonium chloride solution (20 mL) and EtOAc (30 mL). The organic layer was collected, dried and concentrated in vacuo. The residue was purified using silica gel column chromatography eluting with 100% DCM to 50:50 DCM:EtOAc to afford the title compound as a colourless oil (1.05 g, 62%).

$^1$HNMR (400 MHz, CDCl$_3$): δ ppm −0.15 (s, 6H), 0.70 (s, 9H), 1.60 (s, 6H), 3.95 (s, 2H), 7.50 (m, 1H), 7.80 (m, 1H), 8.25 (d, 1H), 8.45 (d, 1H), 8.90 (d, 1H), 8.95 (d, 1H), 9.65 (s, 1H).

Preparation 44

[1-(2-{[tert-butyl(methyl)silyl]oxy}-1,1-dimethylethyl)-1H-pyrrolo[3,2-c]pyridin-3-yl](4-chloropyridin-2-yl)methanone

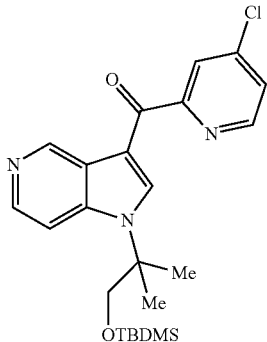 [SMILES: CC(C)(CO[Si](C)(C)C(C)(C)C)n1cc(C(=O)c2cc(Cl)ccn2)c2cnccc21]

1-(2-{[tert-butyl(dimethyl)silyl]oxy}-1,1-dimethylethyl)-3-iodo-1H-pyrrolo[3,2-c]pyridine (Preparation 65, 3.99 g, 9.06 mmol) was dissolved in THF (75 mL) and the solution was degassed and cooled to −5° C. 2M $^i$PrMgCl in THF (5.44 mL, 10.9 mmol) was added dropwise and the resulting yellow solution stirred at this temperature for 45 minutes. A solution of 4-chloro-N-methoxy-M-methylpicolinamide (2.18 g, 10.9 mmol) in THF (20 mL) was added dropwise and the reaction allowed to warm to room temperature for 4.5 hours. The reaction was partitioned between saturated aqueous ammonium chloride solution (30 mL) and EtOAc (50 mL), the organic layer was collected, dried and concentrated in vacuo. The residue was purified using silica gel column chromatography eluting with 0-90% EtOAc in DCM to afford the title compound as an orange oil (2.37 g, 59%). Taken on to the next step directly.

Preparation 45

3-iodo-1-isopropyl-1H-pyrrolo[3,2-c]pyridine

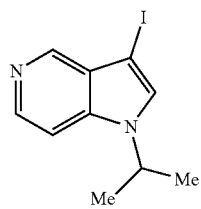 [SMILES: CC(C)n1cc(I)c2cnccc21]

To a suspension of 3-iodo-1H-pyrrolo[3,2-c]pyridine (Preparation 47, 82 g, 340 mmol) and cesium carbonate (164 g, 504 mmol) in DMF (650 mL) was added 2-iodopropane (30.7 mL, 307 mmol) dropwise over 25 minutes at room temperature and the reaction was stirred for 6 hours. The reaction was poured into water (500 mL), stirred for 10 minutes and extracted into EtOAc (4×350 mL). The organic layers were combined, washed with brine, passed through a phase separation cartridge and concentrated in vacuo. The residue was purified using silica gel column chromatography eluting with DCM followed by 50% EtOAc in DCM to afford the title compound as a pale brown gum (93 g, 61%).

$^1$HNMR (400 MHz, CDCl$_3$): δ ppm 1.55 (d, 6H), 4.60-4.70 (m, 1H), 7.20 (d, 1H), 7.30 (s, 1H), 8.35 (d, 1H), 8.70 (s, 1H).

Preparation 46

3-bromo-7-fluoro-1-isopropyl-1H-pyrrolo[3,2-c]pyridine

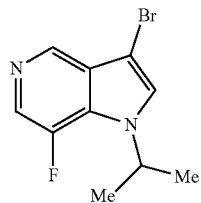

Prepared according to the method described for Preparation 45 using 3-bromo-7-fluoro-1H-pyrrolo[3,2-c]pyridine (Preparation 48), 2-iodopropane and potassium carbonate as base. Purified using silica gel column chromatography eluting with 100% heptanes to 50:50 Heptane:EtOAc to afford the title compound (845 mg, 56%).

$^1$HNMR (400 MHz, CDCl$_3$): δ ppm 1.55, (d, 6H), 4.98 (m, 1H), 7.26 (s, 1H), 8.21 (d, 1H), 8.64 (d, 1H).

Preparation 47

3-iodo-1H-pyrrolo[3,2-c]pyridine

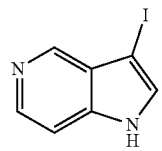

To a solution of 1H-pyrrolo[3,2-c]pyridine (20 g, 170 mmol) in DMF (100 mL) was added KOH (33.2 g, 593 mmol) and the mixture was stirred for 10 minutes. A solution of iodine (47.3 g, 186 mmol) in DMF (100 mL) was added at 0° C., and the reaction allowed to warm to room temperature over 1.5 hours. The reaction was poured onto an aqueous solution of Na$_2$S$_2$O$_5$ (17.2 g) and ammonium hydroxide (35%, 170 mL) in water (2.5 L). The resulting precipitate was filtered, washed with water and dried to afford the title compound (33.5 g, 81%).

$^1$HNMR (400 MHz, DMSO-d$_6$): δ ppm 7.35 (d, 1H), 7.63 (s, 1H), 8.20 (d, 1H), 8.52 (s, 1H).

Preparation 48

3-bromo-7-fluoro-1H-pyrrolo[3,2-c]pyridine

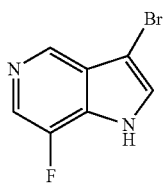

Prepared according to Preparation 61 using NBS.

Preparation 49

(2-chloropyridin-4-yl)-(1H-pyrrolo[3,2-c]pyridin-3-yl)methanone

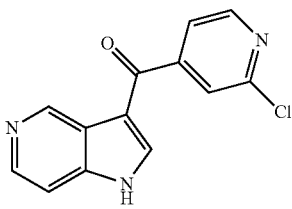 [SMILES: O=C(c1ccnc(Cl)c1)c1c[nH]c2ccncc12]

To a solution of 1H-pyrrolo[3,2-c]pyridine (17.0 g, 0.14 mol) in 1, 2-dichloroethane (500 mL) was added AlCl$_3$ (38.3 g, 0.29 mol) at room temperature. The mixture was stirred at room temperature for 10 minutes. A solution of 2-chloroisonicotinoyl chloride (30.0 g, 0.17 mol) in 1, 2-dichloroethane (100 mL) was added and the reaction heated to 70° C. Further AlCl₃ (38.3 g, 0.29 mol) was added and the reaction was stirred at this temperature for 18 hours. The mixture was cooled to room temperature, and then to the mixture was added MeOH (150 mL) dropwise. 1M aqueous NaOH solution was added until pH=8. The mixture was filtered, the filter cake was washed with a mixture of 1/3 isopropanol/chloroform and the filtrate was extracted with a mixture of 1/3 isopropanol/chloroform (300 mL×6). The combined organic phases were washed with brine, dried over Na₂SO₄ and concentrated under reduced pressure to give the title compound (44 g) as a black solid, which was used in next step directly.

Preparation 50

3-iodo-1-[2-(tetrahydro-2H-pyran-2-yloxy)ethyl]-1H-pyrrolo[3,2-c]pyridine

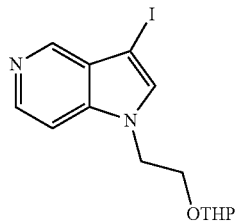

Prepared according to the method described for Preparation 45 using 2-(2-bromoethoxy)tetrahydro-2H-pyran.

¹H NMR (400 MHz, CDCl₃): δ ppm 1.43-1.52 (m, 4H), 1.58-1.69 (m, 2H), 3.33-3.45 (m, 2H), 3.64-3.69 (m, 1H), 3.95-4.04 (m, 1H), 4.30-4.37 (m, 2H), 4.47 (s, 1H), 7.24-7.28 (m, 2H), 8.36 (d, 1H), 8.69 (s, 1H).

Preparation 51

2-[(Diphenylmethylene)amino]-N-methoxy-N-methylisonicotinamide

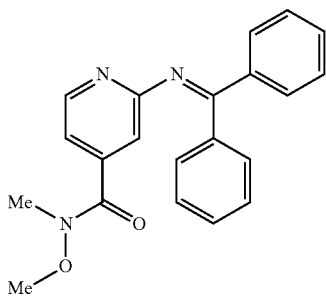 [SMILES: CON(C)C(=O)c1ccnc(N=C(c2ccccc2)c2ccccc2)c1]

Benzophenone imine (2.17 g, 12.0 mmol) was added to 2-bromo-N-methoxy-N-methylisonicotinamide (2.45 g, 10.0 mmol), tris(dibenzylideneacetone)dipalladium (458 mg, 0.50 mmol), 2-di-tert-butylphosphino-2',4',6'-triisopropylbiphenyl (552 mg, 1.30 mmol) and sodium t-butoxide (2.40 g, 25.0 mmol) in toluene (40 mL). The reaction mixture was stirred at room temperature for 2 hours. The mixture was diluted with DCM and filtered through Arbocel™. The filtrate was washed with water (100 mL) then the organic phase was dried over sodium sulphate and evaporated in vacua. The crude material was purified by silica gel column chromatography eluting with heptane:EtOAc 100:0 to 30:70 to afford the title compound as an orange gum (71%, 2.44 g).

¹H NMR (400 MHz, DMSO-d₆): δ ppm 3.14 (br s, 3H), 3.30 (br s, 3H), 6.76 (m, 1H), 7.02 (dd, 1H), 7.11-7.19 (m, 2H), 7.27-7.36 (m, 3H), 7.46-7.54 (m, 2H), 7.59 (m, 1H), 7.66-7.73 (m, 2H), 8.32 (dd, 1H).

Preparation 52

5-[(diphenylmethylene)amino]-N-methoxy-N-methylnicotinamide

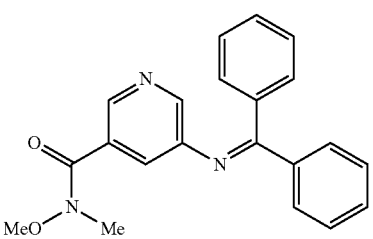 [SMILES: CON(C)C(=O)c1cncc(N=C(c2ccccc2)c2ccccc2)c1]

Prepared according to the method described for Preparation 51 using 5-bromo-N-methoxy-N-methylnicotinamide and benzophenone imine.

¹H NMR (400 MHz, CDCl₃): δ ppm 3.30 (s, 3H), 3.35 (s, 3H), 7.10 (m, 2H), 7.25-7.30 (m, 3H), 7.36 (m, 1H), 7.40-7.45 (m, 2H), 7.50-7.55 (m, 1H), 7.75 (m, 2H), 8.15 (s, 1H), 8.50 (s, 1H).

Preparation 53

3-iodo-1-(oxetan-3-yl)-1H-pyrrolo[3,2-c]pyridine

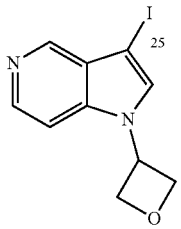 [SMILES: Ic1cn(C2COC2)c2ccncc12]

To a solution of 3-iodo-1H-pyrrolo[3,2-c]pyridine (Preparation 47, 2 g, 8.2 mmol) in DMF (150 mL) was added cesium carbonate (24 g, 73.8 mmol) and the mixture stirred for 20 minutes at room temperature. A solution of trifluoromethanesulfonic acid oxetan-3-yl ester (Preparation 54, 8.45 g, 41 mmol) in DMF (15 mL) was added and the reaction stirred at room temperature for 16 hours. The reaction was filtered, and the filtrate concentrated in vacuo. The residue was purified using silica gel column chromatography eluting with 0-5% MeOH in DCM to give a solid that was further washed with EtOAc:Heptane to afford the title compound. (4.46 g, 36%).

¹H NMR (400 MHz, DMSO-d₆): δ ppm 4.89-4.94 (m, 2H), 4.96-5.02 (m, 2H), 5.81 (m, 1H), 7.57 (m, 1H), 8.10 (s, 1H), 8.29 (m, 1H, d), 8.54 (d, 1H).

Preparation 54

Trifluoromethanesulfonic acid oxetan-3-yl ester

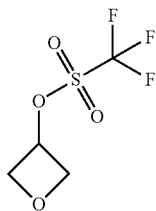 [SMILES: O=S(=O)(OC1COC1)C(F)(F)F]

To a solution of oxetan-3-ol (3 g, 41 mmol) and pyridine (4.97 mL, 61.5 mmol) in DCM (150 mL) was added trifluoromethanesulfonic anhydride slowly dropwise at −50° C., and the reaction was stirred at −30° C. for 2 hours. The reaction was quenched by the addition of aqueous 1N HCl solution (50 mL) and the mixture extracted with DCM (100 mL) thrice. The combined organic layers were dried over MgSO₄ and concentrated in vacuo to afford the title compound as a yellow oil.

¹H NMR (400 MHz, CDCl₃): δ ppm 4.84-4.97 (m, 4H) 5.69-5.77 (m, 1H).

Preparation 55

1-(2-{[tert-butyl(dimethyl)silyl]oxy}-1-methylethyl)-3-iodo-1H-pyrrolo[3,2-c]pyridine

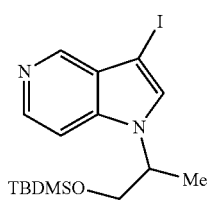 [SMILES: CC(CO[Si](C)(C)C(C)(C)C)n1cc(I)c2cnccc21]

To a solution of 2-(3-iodo-1H-pyrrolo[3,2-c]pyridin-1-yl) propan-1-ol (Preparation 56, 11.5 g, 38.1 mmol) and imidazole (6.48 g, 95.2 mmol) in DCM (300 mL) was added a solution of TBDMSCl (6.95 g, 45.7 mmol) in DCM (50 mL) dropwise at 0° C. The reaction was allowed to warm to room temperature and stirred for 1.5 hours. To the reaction was added water (500 mL) and DCM (200 mL), the organic layer collected, dried over MgSO4 and concentrated in vacuo. The residue was purified using silica gel column chromatography eluting with 0-10% MeOH in DCM to afford the title compound (15 g, 100%).

¹H NMR (400 MHz, CDCl₃): δ ppm −0.15 (d, 6H), 0.80 (s, 9H), 1.60 (d, 3H), 3.73-3.82 (m, 2H), 4.55-4.63 (m, 1H), 7.20 (d, 1H), 7.35 (s, 1H), 8.35 (d, 1H), 8.70 (s, 1H).

Preparation 56

2-(3-iodo-1H-pyrrolo[3,2-c]pyridin-1-yl)propan-1-ol

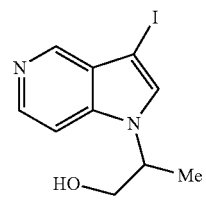 [SMILES: CC(CO)n1cc(I)c2cnccc21]

To a solution of 2-(3-iodo-pyrrolo[3,2-c]pyridine-1-yl)-propionic acid methyl ester (Preparation 57, 18.1 g, 54.8 mmol) in EtOH (300 mL) was added 2M lithium borohydride solution in THF (63.1 mL, 126 mol) at 0° C. The reaction was stirred at this temperature for 30 minutes before warming to room temperature for 18 hours. The reaction was quenched by the addition of water (300 mL) at 0° C. with stirring for 1 hour. The EtOH was removed in vacuo and the resulting residue diluted further with water (600 mL) followed by extraction into 5% MeOH in DCM (250 mL). The organic layer was collected, dried over MgSO₄ and concentrated in vacuo. The residue was purified using silica gel column chromatography eluting with 0-5% MeOH in DCM to afford the title compound (12 g, 73%).

¹H NMR (400 MHz, DMSO-d₆): δ ppm 0.40 (d, 3H), 3.63 (m, 2H), 4.60-4.70 (m, 1H), 4.90 (m, 1H), 7.55 (d, 1H), 7.80 (s, 1H), 8.23 (d, 1H), 8.50 (s, 1H).

Preparation 57

2-(3-iodo-pyrrolo[3,2-c]pyridine-1-yl)-propionic acid methyl ester

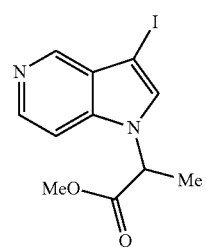 [SMILES: COC(=O)C(C)n1cc(I)c2cnccc21]

Prepared according to the method described for Preparation 45 using 2-bromo-propionic acid methyl ester. Purified using silica gel column chromatography eluting with 0-10% MeOH in DCM.

$^1$H NMR (400 MHz, CDCl$_3$): δ ppm 1.81 (d, 3H), 3.75 (s, 3H), 5.12 (m, 1H), 7.15 (d, 1H), 7.35 (s, 1H), 8.40 (d, 1H), 8.70 (s, 1H).

Preparation 58

1-(2-{[tert-butyl(dimethyl)silyl]oxy}-1-methyl-ethyl)-7-fluoro-3-iodo-1H-pyrrolo[3,2-c]pyridine Enantiomer 1

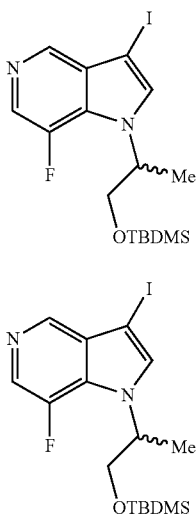

Enantiomer 2

Prepared according to the method described for Preparation 55 using 2-(7-fluoro-3-iodo-1H-pyrrolo[3,2-c]pyridin-1-yl)propan-1-ol (Enantiomer 1, Preparation 59). The residue was purified using silica gel column chromatography eluting with 50% EtOAc in Heptane.

Enantiomer 2 was prepared in the same manner as Enantiomer 1.

$^1$H NMR (400 MHz, DMSO-d$_6$): δ ppm −0.17-0.29 (d, 6H), 0.62 (s, 9H), 1.50 (d, 3H), 3.72-3.76 (m, 1H), 3.82-3.86 (m, 1H), 4.82-4.87 (m, 1H), 7.89 (s, 1H), 8.21 (d, 1H), 8.38 (d, 1H).

Preparation 59

2-(7-fluoro-3-iodo-1H-pyrrolo[3,2-c]pyridin-1-yl)propan-1-ol

Enantiomer 1

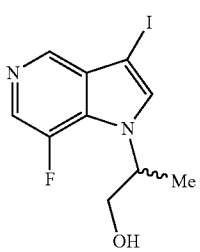

Enantiomer 2

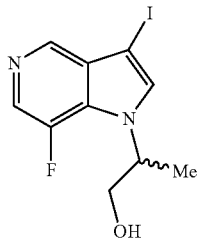

Prepared according to the method described for Preparation 56 using methyl 2-(7-fluoro-3-iodo-1H-pyrrolo[3,2-c]pyridin-1-yl)propanoate (Preparation 60) for 4 hours at 0° C. The reaction was quenched by the addition of aqueous ammonium chloride solution, extracted into EtOAc (3×50 mL), dried over sodium sulphate and concentrated in vacuo. The residue was purified using chiral preparative HPLC (CHIRALPAK AD-H (4.6×250) 5 um eluting with 90% heaxane:10% EtOH at a flow rate of 1.0 mL/min) to afford two enantiomers.

Enantiomer 1 (Peak 1) 1.6 g, 99% ee.
Enantiomer 2 (Peak 2) 1.7 g, 99% ee
$^1$H NMR (400 MHz, DMSO-d$_6$): δ ppm 1.45 (d, 3H), 3.68 (t, 2H), 4.77 (m, 1H), 4.99 (t, 1H), 7.88 (s, 1H), 8.23 (s, 1H), 8.39 (s, 1H).

Preparation 60

Methyl 2-(7-fluoro-3-iodo-1H-pyrrolo[3,2-c]pyridin-1-yl)propanoate

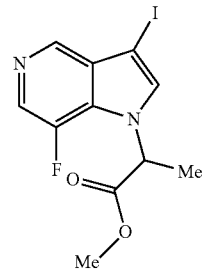 [SMILES: COC(=O)C(C)n1cc(I)c2cncc(F)c21]

Prepared according to the method described for Preparation 45 using 2-bromo-propionic acid methyl ester and 7-fluoro-3-iodo-pyrrolo[3,2-c]pyridine (Preparation 61). Purified using silica gel column chromatography eluting with 0-5% MeOH in DCM.

$^1$H NMR (400 MHz, DMSO-d$_6$): δ ppm 1.79 (d, 3H), 3.67 (s, 3H), 5.59 (m, 1H), 7.86 (s, 1H), 8.27 (d, 1H), 8.44 (d, 1H).

Preparation 61

7-fluoro-3-iodo-1H-pyrrolo[3,2-c]pyridine

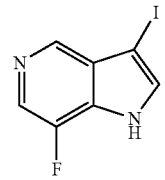 [SMILES: Fc1cncc2c(I)c[nH]c12]

To a solution of 7-fluoro-pyrrolo[3,2-c]pyridine (Preparation 62, 5 g, 36.76 mmol) in anhydrous DMF (35 mL) was added NIS (9 g, 40.44 mmol), and the reaction stirred at room temperature for 4 hours. The reaction was diluted with water and EtOAc. The organic layer was collected, washed with saturate aqueous NaHCO₃ solution, brine, dried over sodium sulphate and concentrated in vacuo. The residue was purified using silica gel column chromatography eluting with 50-100% EtOAc in heptanes followed by 5% MeOH in DCM to afford the title compound (5 g).

¹H NMR (400 MHz, DMSO-d₆): δ ppm 7.76 (s, 1H), 8.24 (s, 1H), 8.43 (s, 1H).

Preparation 62

7-fluoro-1H-pyrrolo[3,2-c]pyridine

A mixture of 3-(2-ethoxy-vinyl)-5-fluoro-pyridin-4-ylamine (Preparation 63, 3.6 g, 19.2 mmol) and concentrated HCl (10 mL) in EtOH (44 mL) was heated to reflux for 4 hours before cooling and concentrating in vacuo. The residue was basified with saturated aqueous NaHCO₃ solution, extracted in DCM, the organic layer collected, dried over sodium sulphate and concentrated in vacuo. The residue was purified using silica gel column chromatography eluting with 20-100% EtOAc in hexane to afford the title compound (1.7 g)

¹H NMR (400 MHz, DMSO-d₆): δ ppm 6.6 (s, 1H), 7.5 (s, 1H), 8.1 (d, 1H), 8.6 (d, 1H), 12.1 (s, 1H).

Preparation 63

3-(2-ethoxy-vinyl)-5-fluoro-pyridin-4-ylamine

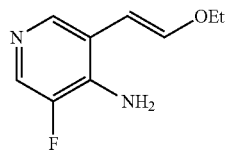 [SMILES: CCO/C=C/c1cncc(F)c1N]

Ethoxyacetylene (7.9 mL, 56.4 mmol) was cooled to 0° C. and a solution of catecholborane (6.1 g, 50.8 mmol) in THF (90 mL) was added slowly. The reaction was allowed to warm to room temperature over 2 hours followed by heating to reflux for 2 hours. The reaction was cooled and 3-fluoro-5-iodo-pyridin-4-ylamine (Preparation 64, 7 g, 29.4 mmol) was added as a solution in THF (20 mL). After purging with nitrogen for 20 minutes, NaOH powder (3.52 g, 88 mmol) and Pd(PPh₃)₄ (1 g, 0.88 mmol) were added and the reaction heated to reflux for 20 hours. The reaction was filtered through celite, washed with EtOAc, the organic layer collected, washed with brine, dried over sodium sulphate and concentrated in vacuo. The residue was purified using silica gel column chromatography eluting with 50% EtOAc in hexane to afford the title compound (3.59 g)

¹H NMR (400 MHz, DMSO-d₆): δ ppm 1.30 (t, 3H), 3.90 (m, 2H), 5.80 (d, 1H), 5.90 (s, 2H), 7.00 (d, 1H), 7.90 (d, 1H), 7.95 (s, 1H).

Preparation 64

3-fluoro-5-iodo-pyridin-4-ylamine

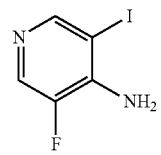

Prepared according to the method described for Preparation 63 using 4-amino-3-fluoropyridine at 80° C. for 48 hours. The organic layer was collected, washed with saturated aqueous NaHCO₃ solution, Na₂S₂O₃ solution, brine, dried over sodium sulphate and concentrated in vacuo. The residue was purified using silica gel column chromatography eluting with 10-30% EtOAc in hexane.

¹H NMR (400 MHz, CDCl₃): δ ppm 4.7 (s, 2H), 8.00 (d, 1H), 8.36 (s, 1H).

Preparation 65

1-(2-{[tert-butyl(dimethyl)silyl]oxy}-1,1-dimethyl-ethyl)-3-iodo-1H-pyrrolo[3,2-c]pyridine

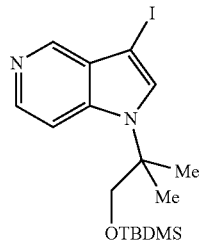 [SMILES: CC(C)(CO[Si](C)(C)C(C)(C)C)n1cc(I)c2cnccc21]

To a suspension of 2-(3-iodo-1H-pyrrolo[3,2-c]pyridin-1-yl)-2-methylpropan-1-ol (Preparation 66, 3.86 g, 12.2 mmol) in DCM (50 mL) was added imidazole (2.08 g, 30.5 mmol) followed by TBDMSCl (2.21 g, 14.7 mmol) and the reaction was stirred at room temperature for 18 hours. The reaction was partitioned between water (30 mL) and DCM (40 mL). The aqueous layer was washed twice with DCM (40 mL), the organic layers combined, dried and concentrated in vacuo. The residue was purified using silica gel column chromatography eluting with 30% EtOAc in heptanes followed by 80:20:2 EtOAc:MeOH:NH3 to afford the title compound as a colourless oil (3.90 g, 74%).

¹H NMR (400 MHz, CDCl₃): δ ppm −0.20 (s, 6H), 0.80 (s, 9H), 1.70 (s, 6H), 3.85 (s, 2H), 7.40 (m, 2H), 8.35 (m, 1H), 8.70 (s, 1H).

Preparation 66

2-(3-iodo-1H-pyrrolo[3,2-c]pyridin-1-yl)-2-methyl-propan-1-ol

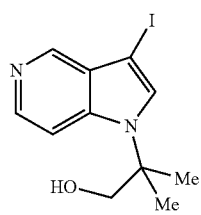 [SMILES: CC(C)(CO)n1cc(I)c2cnccc21]

To a solution of methyl 2-(3-iodo-1H-pyrrolo[3,2-c]pyridin-1-yl)-2-methylpropanoate (Preparation 67, 10.8 g, 31.38 mmol) in EtOH (100 mL) was added sodium borohydride (2.37 g, 62.8 mmol) and the reaction stirred at room temperature for 5 hours. The reaction was quenched by the addition of water (100 mL) and the phases separated through a phase separation cartridge. The organic layer was concentrated in vacuo to afford and orange oil that was triturated with ether to afford an orange solid as the title compound (3.86 g, 39%).

¹H NMR (400 MHz, DMSO-d₆): δ ppm 1.60 (s, 6H), 3.75 (m, 2H), 5.10 (m, 1H), 7.60 (m, 2 h), 8.20 (m, 1H), 8.50 (s, 1H).

Preparation 67

Methyl 2-(3-iodo-1H-pyrrolo[3,2-c]pyridin-1-yl)-2-methylpropanoate

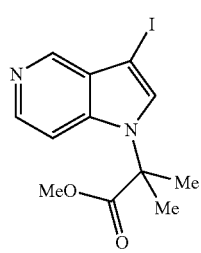 [SMILES: COC(=O)C(C)(C)n1cc(I)c2cnccc21]

To a solution of 2-(3-iodo-pyrrolo[3,2-c]pyridine-1-yl)-propionic acid methyl ester (Preparation 57, 13.1 g, 39.7 mmol) in THF (15 mL) was added methyl iodide (2.96 mL, 47.6 mmol) followed immediately by a 1M solution of potassium tertbutoxide in THF (5.34 g, 47.6 mmol) and the reaction was stirred at room temperature for 15 minutes. The reaction was quenched with water, and the remaining THF removed in vacuo. The residue was extracted with EtOAc, dried and concentrated in vacuo to afford the title compound as a yellow solid (5.1 g, 37%).

¹H NMR (400 MHz, CDCl₃): δ ppm 1.90 (s, 6H), 3.70 (s, 3H), 7.00 (m, 1H), 7.38 (m, 1H), 8.35 (m, 1H), 8.75 (s, 1H).

Preparation 68

(4-aminopyridin-2-yl)(7-fluoro-1-isopropyl-1H-pyrrolo[3,2-c]pyridin-3-yl)methanone

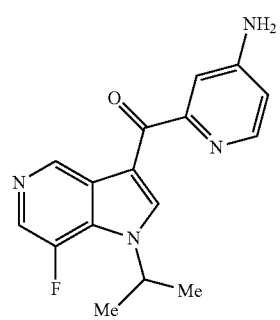 [SMILES: CC(C)n1cc(C(=O)c2cc(N)ccn2)c2cncc(F)c21]

Prepared according to Preparations 36, 35 and 27 using 3-bromo-7-fluoro-1-isopropyl-1H-pyrrolo[3,2-c]pyridine (Preparation 46) and 4-chloro-N-methoxy-N-methylpicolinamide. The compound was used directly in the next step.

Preparation 69 di-tert-butyl {2-methoxy-5-[methoxy(methyl)carbamoyl]pyridin-3-yl}imidodicarbonate

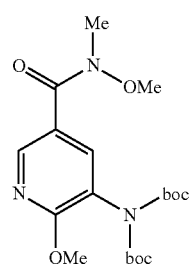

To a solution of 5-[bis(tert-butoxycarbonyl)amino]-6-methoxynicotinic acid (Preparation 70, 500 mg, 1.358 mmol) and DIPEA (730 uL, 4.076 mmol) in DMF (4 mL) was added HATU (774 mg, 2.038 mmol) and N-methoxy-methylamine hydrochloride (198 mg, 2.038 mmol) and the reaction stirred at room temperature for 16 hours. The reaction was partitioned between saturated aqueous NaHCO₃ solution and EtOAc, the organic layer collected, dried over sodium sulfate and concentrated in vacuo to afford the title compound that was used directly in the next step.

Preparation 70

5-[bis(tert-butoxycarbonyl)amino]-6-methoxynicotinic acid

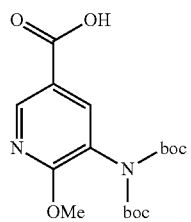

To a solution of the methyl 5-[bis(tert-butoxycarbonyl)amino]-6-methoxynicotinate (1 g, 2.61 mmol) in THF (10 mL) at 0° C. was added LiOH.H$_2$O (275 mg, 6.54 mmol) in water (2.5 mL) and the reaction allowed to stir at room temperature for 4 hours. The reaction was diluted with water (5 mL) and extracted into DCM twice (2×10 mL). The aqueous layer was acidified to pH=5 with 10% citric acid solution and extracted into DCM (4×20 mL). The organic layers were collected, washed with brine (10 mL), dried over sodium sulphate and concentrated in vacuo to afford the title compound that was used directly in the next step.

Preparation 71

2-(7-Fluoro-3-iodo-pyrrolo[3,2-c]pyridin-1-yl)-2-methyl-propionic acid methyl ester

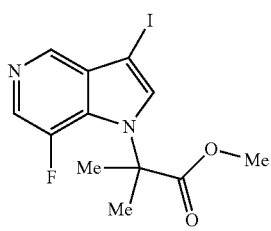 [SMILES: COC(=O)C(C)(C)n1cc(I)c2cncc(F)c21]

To a stirred solution of 2-(7-fluoro-3-iodo-pyrrolo[3,2-c]pyridin-1-yl)-propionic acid methyl ester (8 g, 22.98 mmol) in dry THF (80 mL) was added MeI (1.85 mL, 29.87 mmol) and the flask was placed in a water bath. Potassium tert-butoxide (1M in THF, 29.87 mL, 29.87 mmol) was added over 10 minutes and the mixture was stirred for an additional 10 minutes. Then reaction was quenched with water and few drops of 0.2M HCl and then diluted with EtOAc. The organic layer was washed with water, brine, dried over sodium sulphate and evaporated in vacuo. The crude material was purified by silica gel column chromatography eluting with 0-20% EtOAc in Hexane to afford the title compound as light yellow solid (78%, 6.5 g).

$^1$H NMR (400 MHz, DMSO-d$_6$): δ ppm 1.84 (s, 6H), 3.67 (s, 3H), 7.89 (s, 1H), 8.26 (d, 1H), 8.45 (d, 1H).

LCMS Rt=3.17 minutes MS m/z 363 [M+H]$^+$

Preparation 72

2-(7-Fluoro-3-iodo-pyrrolo[3,2-c]pyridin-1-yl)-2-methyl-propan-1-ol

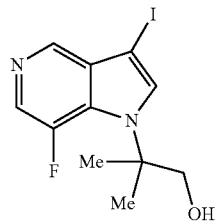 [SMILES: CC(C)(CO)n1cc(I)c2cncc(F)c21]

2-(7-Fluoro-3-iodo-pyrrolo[3,2-c]pyridin-1-yl)-2-methyl-propionic acid methyl ester (Preparation 71, 500 mg, 1.38 mmol) was taken in dry THF (3 mL) and DIBAL-H (25% solution in toluene, 2 mL, 3.03 mmol) was added drop wise at 0° C. and stirred at the same temperature for 2 hours. The reaction was quenched with MeOH, water, 2N HCl at 0° C. and stirred for 15 minutes before being diluted with EtOAc and water. The organic layer was separated and washed with brine, dried over sodium sulphate and evaporated in vacuo to obtain the title compound (65%) that was used in the next step directly without any further purification.

$^1$H NMR (400 MHz, DMSO-d$_6$): δ ppm 1.58 (s, 6H), 3.76 (d, 2H), 5.15 (t, 1H), 7.74 (s, 1H), 8.28 (d, 1H), 8.44 (s, 1H).

LCMS Rt=2.94 minutes MS m/z 335 [M+H]$^+$

Preparation 73

1-[2-(tert-Butyl-dimethyl-silyloxy)-1,1-dimethyl-ethyl]-7-fluoro-3-iodo-1H-pyrrolo[3,2-c]pyridine

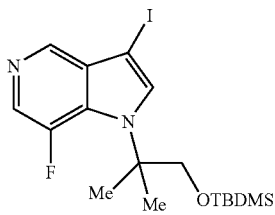 [SMILES: CC(C)(CO[Si](C)(C)C(C)(C)C)n1cc(I)c2cncc(F)c21]

To a solution of 2-(7-fluoro-3-iodo-pyrrolo[3,2-c]pyridin-1-yl)-2-methyl-propan-1-ol (Preparation 72, 4.5 gm, 13.47 mmol) in DCM (90 mL) were added 2,6-lutidine (3.91 mL, 33.65 mmol) and tert-butyl dimethylsilyl trifluoromethane-sulfonate (4.62 gm, 17.51 mmol) at 0° C. The resulting mixture was warmed to room temperature and stirred for 2 hours. The reaction mixture was diluted with DCM. The organic layer was washed with water, brine, dried over sodium sulphate, and evaporated in vacuo. The crude material was purified by silica gel column chromatography eluting with 10-12% EtOAc in Hexane to afford the title compound as off white solid (45%, 2.7 g).

$^1$H NMR (400 MHz, DMSO-d$_6$): δ ppm −0.17 (s, 6H), 0.69 (s, 9H), 1.62 (s, 6H), 3.90 (s, 2H), 7.73 (s, 1H), 8.30 (d, 1H), 8.43 (d, 1H).

LCMS Rt=2.88 minutes MS m/z 449 [M+H]$^+$

Preparation 74

[3-(trifluoromethyl)-1H-pyrazol-1-yl]acetic acid

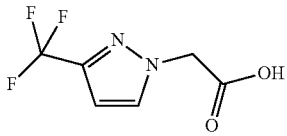 [SMILES: O=C(O)Cn1ccc(C(F)(F)F)n1]

Lithium hydroxide monohydrate (127 mg, 3.03 mmol) in water (0.5 mL) was added to (3-(trifluoromethyl)-1H-pyrazol-1-yl)acetic acid ethyl ester (250 mg, 1.125 mmol) in THF (5 mL). The mixture was stirred at room temperature for 5 hours then the reaction mixture volume was reduced to one third by evaporation in vacuo. The aqueous residue was acidified using aqueous HCl (2M) to pH=5. The resulting off white solid was filtered, collected and dried, washed with ether to afford the title compound as a white solid (42 mg, 19%).

$^1$HNMR (400 MHz, DMSO-$d_6$): δ ppm 5.07 (s, 2H), 6.73 (s, 1H), 7.95 (s, 1H). LCMS (5 minute run) Rt=2.93 minutes MS m/z 195 [M+H]$^+$

Preparation 75

Ethyl (3-cyclopropyl-1H-pyrazol-1-yl) acetate

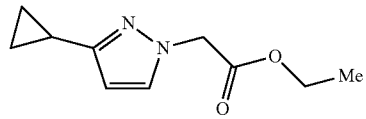

Potassium carbonate (7.67 g, 55.56 mmol) was added to 3-cyclopropyl-1H-pyrazole (2.0 g, 18.52 mmol) in dry DMF (20 mL) at 25° C. and the mixture was stirred for 20 minutes. Ethyl bromoacetate (2.06 mL, 18.52 mmol) was added then the mixture was stirred for 2 days at room temperature. The reaction mixture was neutralized with aqueous HCl (1.0 M), extracted with ether (40 mL) and the organic extract was washed with brine (30 mL), dried over sodium sulfate then evaporated in vacuo. The residue was purified by silica gel column chromatography eluting with hexane:EtOAc 88:12 to afford the title compound as a yellow oil (42%, 1.50 g).

$^1$H NMR (400 MHz, DMSO-$d_6$): δ ppm 0.59 (d, 2H), 0.83 (d, 2H), 1.19 (t, 3H), 1.83 (m, 1H), 4.13 (q, 2H), 4.91 (s, 2H), 5.94 (d, 1H), 7.54 (d, 1H).

Preparation 76

(3-Cyclopropyl-1H-pyrazol-1-yl)acetic acid

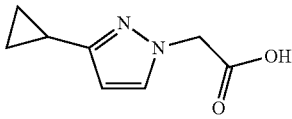 [SMILES: O=C(O)Cn1ccc(C2CC2)n1]

Prepared according to the method described for Preparation 74 using ethyl (3-cyclopropyl-1H-pyrazol-1-yl) acetate (Preparation 75). After acidifying to pH=4 with cHCl, EtOAc followed by water was added. The organic layer was collected and concentrated in vacuo to afford the title compound as a white solid (83%, 4.06 g).

LCMS Rt=1.16 minutes MS m/z 167 [M+H]$^+$

Preparation 77 tert-Butyl[4-(trifluoromethyl)-1H-pyrazol-1-yl]acetate

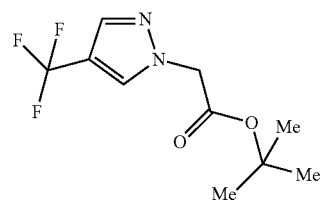 [SMILES: CC(C)(C)OC(=O)Cn1cc(C(F)(F)F)cn1]

The title compound was prepared according to the method described for Preparation 75 using 4-(trifluoromethyl)-1H-pyrazole and tert butyl bromoacetate to afford the title compound as a yellow solid (24%, 1.32 g).

LCMS Rt=3.64 minutes MS m/z 251 [M+H]$^+$

Preparation 78

[4-(Trifluoromethyl)-1H-pyrazol-1-yl]acetic acid

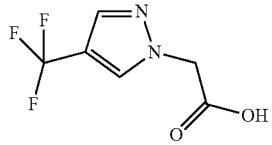 [SMILES: O=C(O)Cn1cc(C(F)(F)F)cn1]

Trifluoroacetic acid (10 mL) was added to tert-butyl[4-(trifluoromethyl)-1H-pyrazol-1-yl]acetate (Preparation 77, 1.3 g, 5.2 mmol) in dry DCM (10 mL) and the mixture was stirred for 18 hours at 25° C. Then the mixture was evaporated in vacuo and the residue was purified by trituration with diethyl ether:pentane (1:9, 2 mL) to afford the title compound as a white solid (79%, 800 mg).

LCMS Rt=1.39 minutes MS m/z 193 [M−H]$^−$

Preparation 79

Ethyl (5-chloropyridin-2-yl)acetate

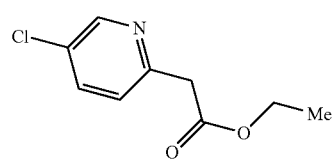 [SMILES: CCOC(=O)Cc1ccc(Cl)cn1]

Cesium carbonate (71 g, 218 mmol) was added to 2-bromo-5-chloropyridine (14 g, 73 mmol) and diethyl malonate (22 mL, 145 mmol) in dry 1,4-dioxane (280 mL) and the solution was degassed with argon for 30 minutes. Then copper (I) oxide (2.8 g, 14.55 mmol) and picolinic acid (3.6 g, 29 mmol) were added and the mixture was stirred in a sealed vessel at 130° C. for 24 hours. The mixture was cooled to room temperature, quenched with water (100 mL) and extracted with EtOAc (3×100 mL). The organic extracts were washed with water (200 mL), brine (200 mL), dried over sodium sulfate and evaporated in vacuo. The residue was purified by silica gel column chromatography eluting with EtOAc: Hexane 92:8 to afford the title compound as a yellow oil (54%, 8.0 g).

$^1$H NMR (400 MHz, DMSO-$d_6$): δ ppm 1.17 (t, 3H), 3.85 (s, 2H), 4.08 (q, 2H), 7.42 (d, 1H), 7.90 (dd, 1H), 8.54 (d, 1H).

Preparation 80

(5-Chloropyridin-2-yl)acetic acid

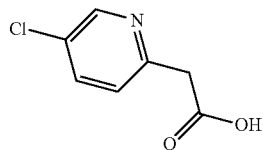

The title compound was prepared according to the method described for Preparation 74 using ethyl (5-chloropyridin-2-yl)acetate (Preparation 79) to afford the title compound as a brown solid (51%, 3.5 g).

LCMS Rt=1.00 minutes MS m/z 172 [M+H]$^+$

Preparation 81

Ethyl (5-fluoropyridin-2-yl)acetate

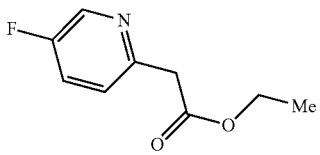 [SMILES: CCOC(=O)Cc1ccc(F)cn1]

The title compound was prepared according to the method described for Preparation 79 using 2-bromo-5-fluoropyridine to afford the title compound as a yellow oil (20%, 5 g).

$^1$H NMR (400 MHz, DMSO-$d_6$): δ ppm 1.17 (t, 3H), 3.84 (s, 2H), 4.08 (q, 2H), 7.42-7.45 (m, 1H), 7.67-7.72 (m, 1H), 8.48 (d, 1H).

Preparation 82

(5-Fluoropyridin-2-yl)acetic acid

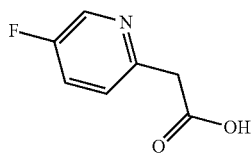 [SMILES: O=C(O)Cc1ccc(F)cn1]

The title compound was prepared according to the method described for Preparation 74 using ethyl (5-fluoropyridin-2-yl)acetate (Preparation 81) to afford the title compound as a brown solid (57%, 2.4 g).

$^1$H NMR (400 MHz, DMSO-$d_6$): δ ppm 3.75 (s, 2H), 7.41-7.44 (m, 1H), 7.65-7.70 (m, 1H), 8.47 (d, 1H), 12.50 (br s, 1H).

Preparation 83

(5-Bromopyridin-2-yl)acetic acid

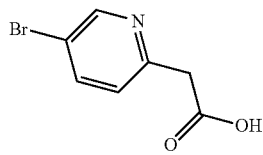

To a solution of diethyl(5-bromopyridin-2-yl)malonate (Preparation 84, 5.28 g, 16.70 mmol) in THF (50 mL) was added a solution of LiOH (2.10 g, 50.13 mmol) in water (12.5 mL) and the reaction was heated to 60° C. for 3 hours. The reaction was cooled and acidified to pH 3-4 with 2N HCl and diluted with 20% IPA in DCM. The organic layer was collected, dried over sodium sulphate and concentrated in vacuo. The crude residue was triturated with hexane to afford the title compound.

$^1$H NMR (400 MHz, DMSO-$d_6$): δ ppm 3.73 (s, 2H), 7.36 (d, 1H), 8.01 (m, 1H), 8.61 (d, 1H), 12.5 (s, 1H).

Preparation 84

Diethyl(5-bromopyridin-2-yl)malonate

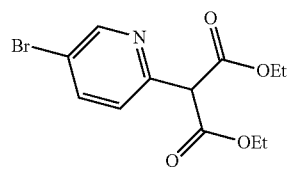 [SMILES: CCOC(=O)C(C(=O)OCC)c1ccc(Br)cn1]

To a suspension of 2-iodo-5-bromopyridine (2.0 g, 7.06 mmol), diethylmalonate (2.12 mL, 14.12 mmol) and cesium carbonate (6.88 g, 21.18 mmol) in dioxane (20 mL) was added copper iodide (268 mg, 1.41 mmol) followed by picolinic acid (346 mg, 2.82 mmol) and the reaction was heated to 80° C. for 16 hours. The reaction was cooled, filtered and the filtrate was concentrated in vacuo. The residue was diluted with EtOAc, washed with water, brine, dried over sodium sulphate and concentrated in vacuo. The residue was purified using silica gel column chromatography eluting with 2% EtOAc in hexanes to afford the title compound that was used directly in the next reaction.

Preparation 85

2-[(cyclopropylcarbonyl)amino]-4-ethoxy-4-oxobutanoic acid

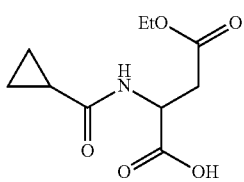 [SMILES: CCOC(=O)CC(NC(=O)C1CC1)C(=O)O]

A solution of cyclopropanecarbonyl chloride (104.5 g, 1 mol) in dichloromethane (170 mL) was added dropwise to a solution of N-hydroxysuccinimide (115 g, 1 mol) and TEA (111 g, 1 mol) in dichloromethane (170 mL) at 0° C. The reaction mixture was stirred at room temperature for 48 hours, and a saturated NaHCO$_3$ solution (500 mL) was added under stirring. The organic layer was separated, and the aqueous layer washed with chloroform thrice. The combined organic layers were washed with a saturated NaHCO$_3$ solution (200 mL), brine (200 mL), dried over Na$_2$SO$_4$, and concentrated in vacuo to afford crude N-cyclopropanecarboxysuccinimide.

NaHCO$_3$ (252 g, 3 mol) was added to a solution of aspartic acid monoethyl ester hydrochloride (229 g, 1 mol) in water (1.7 L), and a solution of the crude N-cyclopropanecarboxysuccinimide (183 g, 1 mol) in dioxane (1.7 L) was added dropwise at 0° C. The reaction mixture was stirred at room temperature for 20 hours, acidified with 4N HCl to pH 3, and subjected to extraction with ethyl acetate (5×500 mL). The extracts were combined, washed with brine, dried over Na$_2$SO$_4$, and concentrated in vacuo. The residue was recrystallized from ethyl acetate to give the title compound as a white crystalline substance (77%, 176 g).

Preparation 86

Ethyl 3-[(Cyclopropylcarbonyl)amino]-4-oxopentanoate

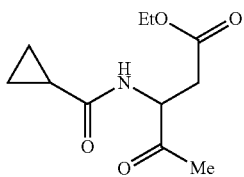 [SMILES: CCOC(=O)CC(NC(=O)C1CC1)C(C)=O]

DMAP (5 g, 0.041 mol) and acetic anhydride (306 g, 3 mol) were added to a suspension of 2-[(cyclopropylcarbonyl)amino]-4-ethoxy-4-oxobutanoic acid (Preparation 85, 229 g, 1 mol) in freshly-distilled pyridine (1.5 L). The reaction was heated at 90° C. for 2 hours before concentrating in vacuo at 60° C., azeotroping with toluene. The residue was purified by silica gel column chromatography eluting with 2% methanol in chloroform to afford the title compound (70%) that was taken directly on to the next step.

Preparation 87

(2-Cyclopropyl-5-methyl-1,3-oxazol-4-yl)acetic acid

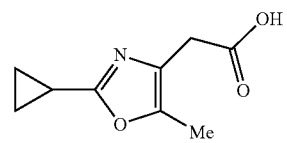 [SMILES: Cc1oc(C2CC2)nc1CC(=O)O]

Ethyl 3-[(Cyclopropylcarbonyl)amino]-4-oxopentanoate (Preparation 86, 22.7 g, 0.1 mol) was dissolved in dry pyridine (170 mL). POCl$_3$ (46 g, 0.3 mol) was poured into this solution with cooling. The reaction was heated at 90° C. for 20 minutes and then rapidly cooled in an ice/water mixture. The cooled solution was slowly poured into crushed ice (700 g), stirred until the solution became homogeneous, and neutralized with 20% aqueous K$_2$CO$_3$ to pH 7. The aqueous was extracted with ethyl acetate, the organic layer washed with brine, and concentrated in vacuo. The residue was purified using silica gel column chromatography eluting with ethyl acetate/hexane 1:1 to afford the ethyl ester intermediate in 73% yield.

An emulsion of this intermediate (20.9 g, 0.1 mol) in 10% KOH (100 mL) was heated at 75° C. The reaction mixture was cooled, acidified with 10% HCl to pH 3, and subjected to extraction with chloroform (3×100 mL). The combined organic layers were dried over Na$_2$SO$_4$ and concentrated in vacuo. The residue was recrystallized from ethyl acetate and vacuum-dried to afford the title compound as a white crystalline solid (93%, 16.9 g).

$^1$H NMR (400 MHz, DMSO-d$_6$) δ: ppm 0.85 (m, 2H), 0.95 (m, 2H), 1.95 (m, 1H), 2.15 (s, 3H), 3.40 (s, 2H), 12.25 (s, 1H).

Preparation 88

(2,5-dicyclopropyl-1,3-oxazol-4-yl)acetic acid

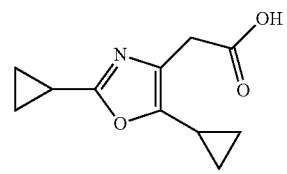 [SMILES: O=C(O)Cc1nc(C2CC2)oc1C1CC1]

Preparation 89

(2-Methyl-cyclopropyl-1,3-oxazol-4-yl)acetic acid

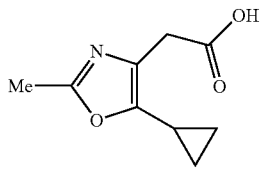 [SMILES: Cc1nc(CC(=O)O)c(C2CC2)o1]

Prepared analogously to Preparations 85, 86 and 87.

Preparation 90

[4-(Trifluoromethyl)-1H-1,2,3-triazol-1-yl]acetic acid

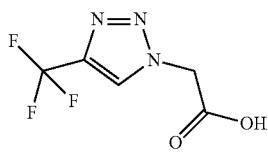

Trifluoromethyl acetylene (22.0 g, 0.234 mol) in THF (210 mL) was added to sodium ascorbate (2.77 g, 14.0 mmol), ethyl azidoacetate (27.1 g, 0.210 mol) and copper sulfate (4.76 mL, 0.3 M in water) in water (105 mL). The mixture was stirred at room temperature for 240 hours then evaporated in vacuo. The residue was extracted with EtOAc (500 mL) and the organic phase was dried over magnesium sulfate then evaporated in vacuo.

Sodium hydroxide (7.32 g, 0.183 mol) in water (30 mL) was added to the residue (32.7 g, 0.146 mol) in methanol (50 mL) and the mixture was stirred at room temperature for 17 hours. The methanol was evaporated in vacuo and the residue was diluted with water (10 mL). Potassium hydrogen sulfate (26.6 g, 0.195 mol) in water (70 mL) was added. The solution was evaporated in vacuo and the crude solid was purified by crystallisation using water to afford the title compound as a white solid (75%, 25.8 g).

$^1$H NMR (400 MHz, DMSO-$d_6$): δ ppm 5.40 (s, 2H), 8.85 (s, 1H), 13.50 (br s, 1H).

Preparation 91

Ethyl (2-cyclopropyl-1,3-oxazol-4-yl)acetate

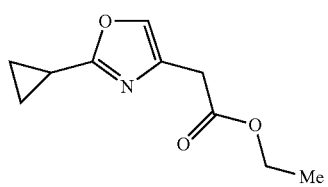 [SMILES: CCOC(=O)Cc1coc(C2CC2)n1]

Ethyl 4-chloroacetoacetate (20.0 g, 122.0 mmol) was added to cyclopropanecarboxamide (3.52 g, 41.5 mmol) in toluene (100 mL) and 1,4-dioxane (100 mL). The mixture was refluxed at 120° C. for 17 hours then evaporated in vacuo. The crude solid was purified by silica gel column chromatography eluting with 80:20 petroleum ether: EtOAc to afford the title compound as a white solid (50%, 4.00 g).

$^1$H NMR (300 MHz, DMSO-$d_6$): δ ppm 0.80-1.00 (m, 4H), 1.20 (t, 3H), 2.10 (m, 1H), 3.50 (s, 2H), 4.10 (q, 2H), 7.80 (s, 1H).

Preparation 92

(2-Cyclopropyl-1,3-oxazol-4-yl)acetic acid

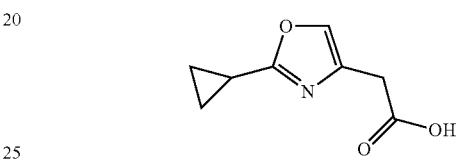

Lithium hydroxide monohydrate (7.83 g, 186.7 mmol) was added to ethyl (2-cyclopropyl-1,3-oxazol-4-yl)acetate (Preparation 91, 7.00 g, 35.9 mmol) in THF (200 mL) and water (100 mL). The mixture was stirred at room temperature for 2 hours then the reaction mixture volume was reduced to one third by evaporation in vacuo. The aqueous residue was acidified using aqueous 1M HCl then extracted with EtOAc (200 mL). The organic phase was evaporated in vacuo and the crude material was triturated with diethyl ether (100 mL) to afford the title compound as a white solid (66%, 4.00 g).

$^1$H NMR (300 MHz, CDCl$_3$): δ ppm 1.05 (m, 4H), 2.10 (m, 1H), 3.60 (s, 2H), 7.40 (s, 1H), 10.00 (br s, 1H).

Preparation 93

Ethyl (4-cyclopropyl-1H-1,2,3-triazol-1-yl)acetate

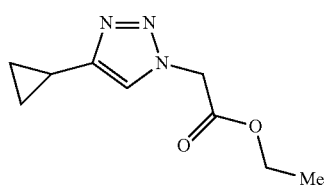 [SMILES: CCOC(=O)Cn1cc(C2CC2)nn1]

Cyclopropylacetylene (15 g, 0.116 mol), ethyl azidoacetate (11.5 g, 0.174 mol), triethylamine (0.32 mL, 2.33 mmol) and copper iodide (442 mg, 2.33 mmol) in acetonitrile (100 mL) were stirred at 25° C. for 18 hours. The mixture was evaporated in vacuo and the residue was partitioned between water (100 mL) and ethyl acetate (100 mL). The organic phase was dried over sodium sulfate, evaporated in vacuo and purified by silica gel column chromatography eluting with EtOAc: Hexane 40: 60 to afford the title compound as a colorless liquid (95%, 21.6 g).

¹H NMR (400 MHz, DMSO-d₆): δ ppm 0.68 (m, 2H), 0.90 (m, 2H), 1.21 (t, 3H), 1.95 (m, 1H), 4.17 (q, 2H), 5.29 (s, 2H), 7.81 (s, 1H).

Preparation 94

(4-Cyclopropyl-1H-1,2,3-triazol-1-yl)acetic acid

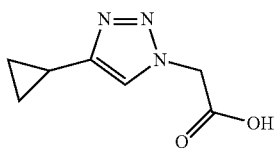 [SMILES: O=C(O)Cn1cc(C2CC2)nn1]

The title compound was prepared according to the method described for Preparation 92 using ethyl (4-cyclopropyl-1H-1,2,3-triazol-1-yl)acetate (Preparation 93) to afford the title compound as a yellow solid (63%, 13.0 g).
LCMS Rt=1.86 minutes MS m/z 168 [M+H]⁺

Preparation 95

[4-Cyano-3-(trifluoromethyl)phenyl]acetic acid

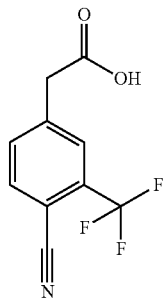 [SMILES: N#Cc1ccc(CC(=O)O)cc1C(F)(F)F]

Lithium diisopropylamide (13.8 mL, 24.8 mmol, 1.8M in THF) was added to 4-methyl-2-(trifluoromethyl)benzonitrile (2.30 g, 12.4 mmol) in THF (20 mL) at −78° C. and stirred for 5 minutes at −78° C. Excess solid carbon dioxide was added then the mixture was stirred at room temperature for 17 hours. Saturated aqueous ammonium chloride (10.5 mL) and EtOAc (20 mL) was added and the aqueous layer was acidified with 1M HCl. The mixture was extracted with EtOAc (3×15 mL) and the combined organic phases were dried over sodium sulphate and evaporated in vacuo to afford the title compound as a brown oil (88%, 2.52 g).
¹H NMR (400 MHz, CDCl₃): δ ppm 3.81 (s, 2H), 7.62 (d, 1H), 7.73 (s, 1H), 7.83 (d, 1H).

Preparation 96

1-Cyclopropyl-5-trifluoromethyl-1H-pyrazole-4-carboxylic acid ethyl ester

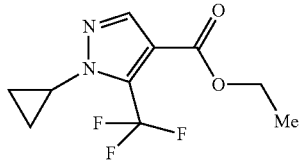 [SMILES: CCOC(=O)c1cnn(C2CC2)c1C(F)(F)F]

Step 1

4,4,4-Trifluoro-3-oxo-butyric acid ethyl ester (16 g, 86.4 mmol) was dissolved in acetic anhydride (33.6 g, 329.6 mmol) and triethyl orthoformate (38.4 g, 260 mmol) was added to the mixture. The resultant mixture was refluxed for 18 hours. The mixture was concentrated under reduced pressure to obtain 20 g of 2-[1-Ethoxy-meth-(E)-ylidene]-4,4,4-trifluoro-3-oxo-butyric acid ethyl ester as crude.

Step 2

This was taken in EtOH (50 mL) and added to a suspension of cyclopropyl hydrazine hydrochloride (9.95 g, 91.7 mmol) and DIPEA (28.3 ml, 166.7 mmol) in EtOH (150 mL) at −20° C. The resultant mixture was slowly warmed to room temperature and stirred for 16 hours. The mixture was concentrated under reduced pressure and residue formed was partitioned between EtOAc (50 mL) and water (50 mL). The organic layer was washed with 2N HCl (25 mL), water (25 mL), brine (25 mL), dried (Na₂SO₄) and evaporated in vacuo. The crude material was purified by silica gel column chromatography eluting with EtOAc:Hexane 5:95 to afford the title compound as an off white sticky solid (1.4 g, 7%).
¹H NMR (400 MHz, DMSO-d₆): δ ppm 1.10-1.21 (m, 4H), 1.26 (t, 3H), 3.90 (m, 1H), 4.26 (q, 2H), 7.98 (s, 1H).

Preparation 97

(1-Cyclopropyl-5-trifluoromethyl-1H-pyrazol-4-yl)-methanol

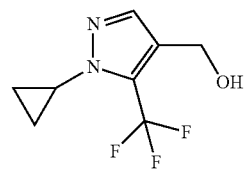 [SMILES: OCc1cnn(C2CC2)c1C(F)(F)F]

A solution of 1-cyclopropyl-5-trifluoromethyl-1H-pyrazole-4-carboxylic acid ethyl ester (Preparation 96, 1.4 g, 5.64 mmol) in dry toluene (25 mL) was cooled to −78° C. and DIBAL-H (11.8 mL of 1.2 M solution in toluene, 14.1 mmol) was added dropwise to it. The reaction mixture was stirred at −78° C. for 2 hours and poured into 2N HCl (10 mL). This was stirred for a further 4 hours at room temperature followed by extraction with EtOAc (2×25 mL) and the combined organic layers were washed with water (2×10 mL), brine (10 mL) dried (Na₂SO₄) and evaporated in vacuo to afford the title compound as off white solid (100%, 1.2 g).
¹H NMR (400 MHz, DMSO-d₆): δ ppm 1.03-1.17 (m, 4H), 3.68-3.73 (m, 1H), 4.42 (d, 2H), 5.15 (t, 1H), 7.51 (s, 1H).
LCMS Rt=2.68 minutes MS m/z 207 [M+H]⁺

Preparation 98

(1-Cyclopropyl-5-trifluoromethyl-1H-pyrazol-4-yl)-acetonitrile

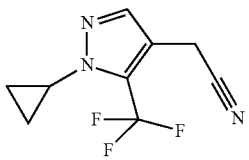 [SMILES: N#CCc1cnn(C2CC2)c1C(F)(F)F]

A solution of (1-cyclopropyl-5-trifluoromethyl-1H-pyrazol-4-yl)-methanol (Preparation 97, 1.2 g, 5.82 mmol) in DCM (15 mL) was cooled to 0° C. and thionyl chloride (0.85 mL, 11.7 mmol) was added. The reaction mixture was stirred at 0° C. for 2 hours and diluted with DCM. The organic layer was washed with water, brine and dried ($Na_2SO_4$) and evaporated in vacuo. The crude residue obtained was dissolved in dioxane (25 mL) and water (25 mL) and tetrabutyl ammonium bromide (1.38 g, 4.28 mmol) was added. The reaction mixture was stirred for 10 minutes followed by the addition of KCN (1.28 g, 19.82 mmol) and resultant mixture was stirred for a further 16 hours at room temperature. The mixture was diluted with EtOAc (50 mL) and washed with water (1×10 mL), brine (1×10 mL), dried ($Na_2SO_4$) and evaporated in vacuo. The crude material was purified by silica gel column chromatography eluting with Hexane:EtOAc 10:90 to afford the title compound as light yellow solid (56%, 700 mg).

$^1$H NMR (400 MHz, $CDCl_3$): δ ppm 1.06-1.13 (m, 2H), 1.24-1.29 (m, 2H), 3.61-3.62 (m, 1H), 3.66 (s, 2H), 7.49 (s, 1H).

Preparation 99

(1-Cyclopropyl-5-trifluoromethyl-1H-pyrazol-4-yl)-acetic acid

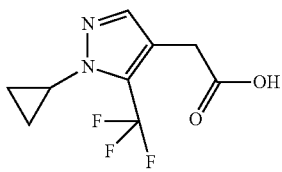 [SMILES: O=C(O)Cc1cnn(C2CC2)c1C(F)(F)F]

To a solution of (1-Cyclopropyl-5-trifluoromethyl-1H-pyrazol-4-yl)-acetonitrile (Preparation 98, 700 mg, 3.25 mmol) in EtOH (15 mL) was added aqueous 1N NaOH (15 mL). The resulting solution was heated at 60° C. for 16 hours. The mixture was concentrated in vacuo and the residue was dissolved in water (10 mL) and washed with EtOAc. The aqueous layer was acidified to pH5 using 1N HCl and extracted with 10% IPA in DCM (4×30 mL). The organic layer was dried ($Na_2SO_4$) and evaporated in vacuo to afford the title compound as a solid (85%, 650 mg).

$^1$H NMR (400 MHz, DMSO-$D_6$): δ ppm 1.04-1.07 (m, 2H), 1.11-1.16 (m, 2H), 3.55 (s, 2H), 3.69-3.73 (m, 1H), 7.47 (s, 1H), 12.45 (br, 1H).

LCMS Rt=1.50 minutes MS m/z 233 [M−H]$^+$

Preparation 100

Ethyl 5-(trifluoromethyl)-1H-pyrazole-4-carboxylate

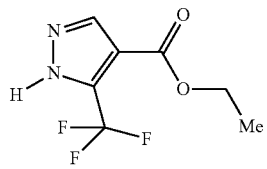 [SMILES: CCOC(=O)c1cn[nH]c1C(F)(F)F]

To a suspension of hydrazine hydrochloride (10 g, 147 mmol) in EtOH (500 mL), DIPEA (45.3 mL, 267 mmol) was added slowly at −20° C. and stirred for 10 minutes. Then 2-[1-ethoxy-meth-(E)-ylidene]-4,4,4-trifluoro-3-oxo-butyric acid ethyl ester (Preparation 96 Step 1, 32 g, 133.33 mmol) was added to above solution and the resulting mixture was stirred at room temperature for 16 hours. The reaction mixture was concentrated under reduced pressure and residue was partitioned between EtOAc (200 mL) and water (50 mL). The organic layer was washed with water (25 mL), dried ($Na_2SO_4$) and evaporated in vacuo. The crude material was purified by silica gel column chromatography eluting with Hexane:EtOAc 90:10 to afford the title compound as off white solid (43%, 13 g).

$^1$H NMR (400 MHz, DMSO-$D_6$): δ ppm 1.26 (t, 3H), 4.25 (q, 2H), 8.57 (s, 1H), 14.10 (br s, 1H).

Preparation 101

1-Cyclopropyl-3-trifluoromethyl-1H-pyrazole-4-carboxylic acid ethyl ester

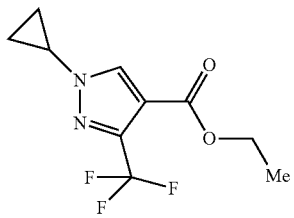 [SMILES: CCOC(=O)c1cn(C2CC2)nc1C(F)(F)F]

Cyclopropyl boronic acid (11 g, 127 mmol), Copper acetate (17.4 g, 95.7 mmol), Pyridine (17.7 g, 223 mmol) and triethylamine (22.4 mL, 160 mmol) were added successively to a solution of ethyl 5-(trifluoromethyl)-1H-pyrazole-4-carboxylate (Preparation 100, 6.63 g, 31.9 mmol) in THF (70 mL) and the resulting mixture was allowed to stir at 60° C. for 36 hours. The reaction mixture was filtered over a celite bed and filtrate was concentrated in vacuo and diluted with EtOAc (200 mL). The organic layer was washed with 1N HCl (1×25 mL), brine (1×25 mL) and dried ($Na_2SO_4$) and evaporated in vacuo. The crude material was purified by silica gel column chromatography eluting with Hexane:EtOAc 85:15 to afford the title compound as brown solid (29%, 2.3 g).

$^1$H NMR (400 MHz, $CDCl_3$): δ ppm 1.08-1.14 (m, 2H), 1.17-1.21 (m, 2H), 1.33 (t, 3H), 3.62-3.67 (m, 1H), 4.30 (q, 2H), 8.01 (s, 1H).

LCMS Rt=3.39 minutes MS m/z 249 [M+H]$^+$

Preparation 102

(1-Cyclopropyl-3-trifluoromethyl-1H-pyrazol-4-yl)-methanol

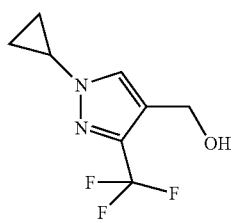 [SMILES: OCc1cn(C2CC2)nc1C(F)(F)F]

A solution of 1-Cyclopropyl-3-trifluoromethyl-1H-pyrazole-4-carboxylic acid ethyl ester (Preparation 101, 3.5 g, 14.11 mmol) in dry toluene (70 mL) was cooled to −78° C. and DIBAL-H (29.4 mL of a 1.2 M solution in toluene, 35.3 mmol) was added dropwise. The reaction mixture was stirred at −78° C. for 2 hours and then poured into 2N HCl (25 mL) followed by further stirring for 2 hours at room temperature. The mixture was extracted with EtOAc (2×50 mL) and the combined organic layers were washed with water (2×15 mL), brine (15 mL) and dried ($Na_2SO_4$) and evaporated in vacuo to afford the title compound as off white solid (100%, 3 g).

$^1$H NMR (400 MHz, $CDCl_3$): δ ppm 1.02-1.07 (m, 2H), 1.11-1.16 (m, 2H), 1.68 (t, 1H), 3.57-3.63 (m, 1H), 4.64 (d, 2H), 7.53 (s, 1H).

LCMS Rt=2.57 minutes MS m/z 207 [M+H]$^+$

Preparation 103

(1-Cyclopropyl-3-trifluoromethyl-1H-pyrazol-4-yl)-acetonitrile

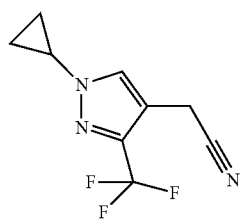 [SMILES: N#CCc1cn(C2CC2)nc1C(F)(F)F]

The title compound was prepared according to the method described for Preparation 98 using (1-Cyclopropyl-3-trifluoromethyl-1H-pyrazol-4-yl)-methanol (Preparation 102) to afford the title compound as yellow solid in 70% yield, 2.2 g.

$^1$H NMR (400 MHz, DMSO-$d_6$): δ ppm 0.98-1.03 (m, 2H), 1.06-1.11 (m, 2H), 3.83-3.88 (m, 1H), 3.91 (s, 2H), 8.08 (s, 1H).

LCMS Rt=3.10 minutes MS m/z 216 [M+H]$^+$

Preparation 104

(1-Cyclopropyl-3-trifluoromethyl-1H-pyrazol-4-yl)-acetic acid

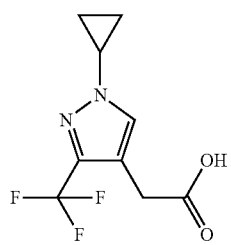 [SMILES: O=C(O)Cc1cn(C2CC2)nc1C(F)(F)F]

The title compound was prepared according to the method described for Preparation 99 using (1-Cyclopropyl-3-trifluoromethyl-1H-pyrazol-4-yl)-acetonitrile (Preparation 103) to afford the title compound as a solid (79%, 1.9 g).

$^1$H NMR (400 MHz, DMSO-$d_6$): δ ppm 0.96-1.07 (m, 4H), 3.49 (s, 2H), 3.76-3.84 (m, 1H), 7.91 (s, 1H), 12.27 (br, 1H).

LCMS Rt=1.41 minutes MS m/z 233 [M−H]$^+$

Preparation 105

[1-Isopropyl-5-(trifluoromethyl)-1H-pyrazol-4-yl]methanol

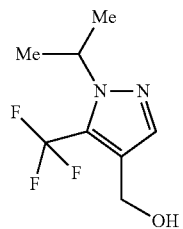

Diisobutylaluminium hydride (99 mL, 120 mmol, 1.2 M solution in toluene) was added to ethyl 1-isopropyl-5-(trifluoromethyl)-1H-pyrazole-4-carboxylate (WO 2007071900, 12 g, 48 mmol) in toluene (220 mL) at −78° C. The reaction mixture was stirred at −78° C. for 2 hours then poured into aqueous HCl (100 mL, 2M). The mixture was stirred for 4 hours at room temperature then extracted with EtOAc (400 mL). The organic phase was washed with water (200 mL), brine (200 mL) and dried over sodium sulphate. The filtrate was evaporated in vacuo to afford the title compound as a colourless oil (100%, 10.5 g).

$^1$H NMR (400 MHz, $CDCl_3$): δ ppm 1.51 (d, 6H), 4.57-4.66 (m, 3H), 7.58 (s, 1H).

Preparation 106

[1-Isopropyl-5-(trifluoromethyl)-1H-pyrazol-4-yl]
acetonitrile

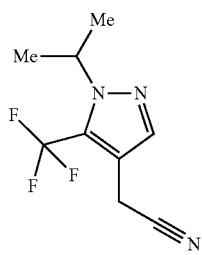 [SMILES: CC(C)n1ncc(CC#N)c1C(F)(F)F]

Thionyl chloride (5.26 mL, 72 mmol) was added to [1-isopropyl-5-(trifluoromethyl)-1H-pyrazol-4-yl]methanol (Preparation 105, 7.5 g, 36 mmol) in DCM (75 mL) at 0° C. and the mixture was stirred for 2 hours. The mixture was diluted with DCM (30 mL) and the organic phase was washed with water (75 mL), brine (75 mL) and dried over sodium sulphate. The filtrate was evaporated in vacuo to afford 4-(chloromethyl)-1-isopropyl-5-(trifluoromethyl)-1H-pyrazole (86%, 7 g).

Tetrabutyl ammonium bromide (7.95 gm, 24.7 mmol) was added to 4-(chloromethyl)-1-isopropyl-5-(trifluoromethyl)-1H-pyrazole (7 g, 31 mmol) in dioxane (75 mL) and water (75 mL) and the mixture was stirred for 10 minutes. Potassium cyanide (7.42 g, 114 mmol) was added and the mixture was stirred for 16 hours at room temperature. The mixture was diluted with EtOAc (100 mL) then the organic phase was washed with water (100 mL), brine (100 mL) and dried over sodium sulphate. The filtrate was evaporated in vacuo and purified by silica gel column chromatography eluting with hexane:EtOAc 90:10 to afford the title compound as a white solid (100%, 7.00 g).

$^1$H NMR (400 MHz, DMSO-d$_6$): δ ppm 1.43 (d, 6H), 3.99 (s, 2H), 4.61 (m, 1H), 7.71 (s, 1H).

Preparation 107

[1-Isopropyl-5-(trifluoromethyl)-1H-pyrazol-4-yl]
acetic acid

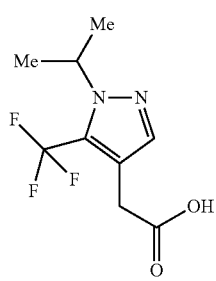

Aqueous sodium hydroxide (150 mL of a 1 M solution) was added to [1-isopropyl-5-(trifluoromethyl)-1H-pyrazol-4-yl]acetonitrile (Preparation 106, 6.2 g, 28.6 mmol) in EtOH (150 mL) and the mixture was heated at 60° C. for 16 hours. The mixture was evaporated in vacuo and the residue was dissolved in water (50 mL) then washed with EtOAc (100 mL). The aqueous phase was acidified to pH 5 using 1N HCl and extracted with 10% IPA in DCM (4×100 mL). The combined organic phases were dried over sodium sulphate and evaporated in vacuo to afford the title compound as a white solid in 75% yield, 5.0 g.

$^1$H NMR (400 MHz, DMSO-d$_6$): δ ppm 1.42 (d, 6H), 3.56 (s, 2H), 4.58 (m, 1H), 7.57 (s, 1H), 12.28 (br s, 1H).

Preparation 108

[1-Isopropyl-3-(trifluoromethyl)-1H-pyrazol-4-yl]
acetic acid

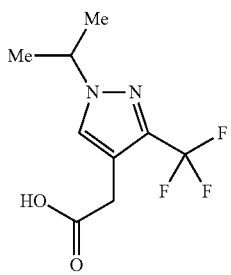 [SMILES: CC(C)n1cc(CC(=O)O)c(C(F)(F)F)n1]

Prepared according to the method described for Preparation 99 using [1-Isopropyl-3-(trifluoromethyl)-1H-pyrazol-4-yl]acetonitrile (Preparation 109).

$^1$H NMR (400 MHz, DMSO-d$_6$): δ ppm 1.42 (d, 6H), 3.50 (s, 2H), 4.52-4.59 (m, 1H), 7.89 (s, 1H).

LCMS (5 minute run) Rt=1.56 minutes MS m/z 235 [M−H]$^-$

Preparation 109

[1-Isopropyl-3-(trifluoromethyl)-1H-pyrazol-4-yl]
acetonitrile

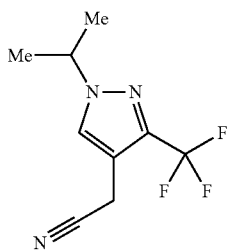 [SMILES: CC(C)n1cc(CC#N)c(C(F)(F)F)n1]

Prepared according to the method described for Preparation 98 using [1-Isopropyl-3-(trifluoromethyl)-1H-pyrazol-4-yl]methanol (Preparation 110).

¹H NMR (400 MHz, DMSO-d₆): δ ppm 1.42 (d, 6H), 3.92 (s, 2H), 4.56-4.63 (m, 1H), 8.06 (s, 1H).

Preparation 110

[1-Isopropyl-3-(trifluoromethyl)-1H-pyrazol-4-yl]methanol

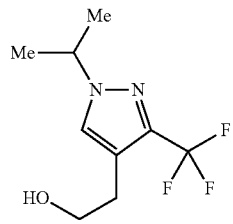 [SMILES: CC(C)n1cc(CCO)c(C(F)(F)F)n1]

To a solution of 1-Isopropyl-3-(trifluoromethyl)-1H-pyrazole-4-carboxylic acid ethyl ester (Preparation 111, 10.2 g, 40.76 mmol) in toluene (200 mL) at −78° C. was added DIBALH (85 mL, 101.91 mmol) dropwise and the reaction allowed to stir at this temperature for 2 hours. 2N HCl was added to quench the reaction followed by extraction into EtOAc. The organic layer was collected, washed with water, brine, dried over sodium sulphate and concentrated in vacuo to afford the title compound (8.3 g) that was taken directly on to the next step.

Preparation 111

1-Isopropyl-3-(trifluoromethyl)-1H-pyrazole-4-carboxylic acid ethyl ester

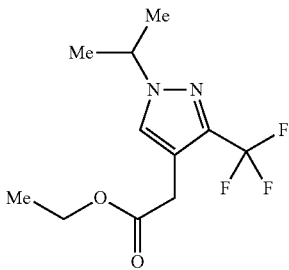 [SMILES: CCOC(=O)Cc1cn(C(C)C)nc1C(F)(F)F]

Prepared according to Preparation 45 using 3-(trifluoromethyl)-1H-pyrazole-4-carboxylic acid ethyl ester (Preparation 112) and isopropyl iodide. Taken directly on to the next step.

Preparation 112

3-(trifluoromethyl)-1H-pyrazole-4-carboxylic acid ethyl ester

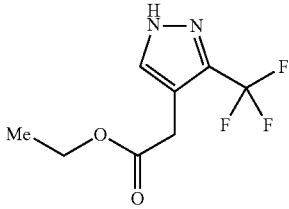 [SMILES: CCOC(=O)Cc1c[nH]nc1C(F)(F)F]

To a suspension of hydrazine hydrochloride (10 g, 146.66 mmol) in ethanol (500 mL) at −20° C. was added DIPEA (45.3 mL, 266.66 mmol) followed by stirring at this temperature for 10 minutes. Ethyl (2Z)-2-(ethoxymethylene)-4,4,4-trifluoro-3-oxobutanoate (Preparation 113, 32 g, 133.33 mmol) was added and the reaction stirred at room temperature for 18 hours. The reaction was concentrated in vacuo and diluted with EtOAc. The organic solution was washed with water, dried over sodium sulphate and concentrated in vacuo. The residue was purified using silica gel column chromatography eluting with 30% EtOAc in hexane to afford the title compound (13 g) that was taken directly on to the next step.

Preparation 113

Ethyl (2Z)-2-(ethoxymethylene)-4,4,4-trifluoro-3-oxobutanoate

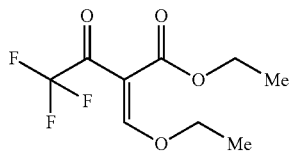

To a solution of ethyl 4,4,4-trifluoro-3-oxobutanoate (20 g, 108.63 mmol) in acetic anhydride (39 mL) was added triethylorthoformate (54.2 mL, 325.89 mmol) and the reaction heated to reflux for 18 hours. The reaction was cooled, concentrated in vacuo and used directly in the next step.

Preparation 114

[3-tert-Butyl-1-(2-methoxyethyl)-1H-1,2,4-triazol-5-yl]acetic acid

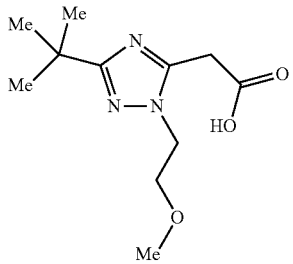 [SMILES: COCCn1nc(C(C)(C)C)nc1CC(=O)O]

Ethyl [3-tert-Butyl-1-(2-methoxyethyl)-1H-1,2,4-triazol-5-yl]acetate (Preparation 115, 23.1 g, 0.086 mol) was dissolved in methanol (150 mL), and 1.9N LiOH (68 mL, 0.13 mol) was added. The mixture was stirred at 0° C. for 30 minutes and concentrated in vacuo at 30° C. Water (70 mL) was added. The resulting mixture was washed with ether (3×100 mL) and neutralized with titrated 2.6N HCl (49.6 mL, 0.13 mol). The resulting precipitate was filtered, washed with water, hexane and dried to afford the title compound (16.54 g, 80%).

¹H NMR (400 MHz, DMSO-d$_6$): δ ppm 1.25 (s, 9H), 3.21 (s, 3H), 3.62 (t, 2H), 3.83 (s, 2H), 4.18 (t, 2H), 12.76 (br s, 1H).

Preparation 115

Ethyl [5-tert-Butyl-1-(2-methoxyethyl)-1H-1,2,4-triazol-3-yl]acetate and Ethyl [3-tert-Butyl-1-(2-methoxyethyl)-1H-1,2,4-triazol-5-yl]acetate

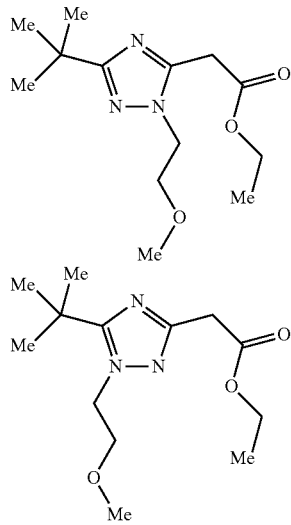

Ethyl (3-tert-Butyl-1H-1,2,4-triazol-5-yl)acetate (Preparation 116, 27.4 g, 0.13 mol) and 1-bromo-2-methoxyethane (13.7 mL, 0.143 mol) was dissolved in DMF (400 mL). K$_2$CO$_3$ (90.0 g, 0.65 mol) was added and the reaction mixture was stirred for 6 hours at 50-60° C. The reaction was cooled to room temperature, diluted with water (400 mL), and extracted with Et$_2$O (3×100 mL). The combined organic extracts were washed with brine (3×200 mL), dried with Na$_2$SO$_4$, and evaporated to afford a mixture of alkylated triazole residues. The mixture was separated using HPLC (Luna 10 u 018(2), 100 A, 21.2×250 mm, H$_2$O/acetonitrile 30-40%) to afford ethyl[3-tert-Butyl-1-(2-methoxyethyl)-1H-1,2,4-triazol-5-yl]acetate (23.14 g, 66%).

¹H NMR (400 MHz, DMSO-d$_6$): δ ppm 1.19 (t, 3H), 1.25 (s, 9H), 3.21 (s, 3H), 3.62 (t, 2H), 3.93 (s, 2H), 4.11 (q, 2H), 4.19 (t, 2H).

Preparation 116

Ethyl (3-tert-Butyl-1H-1,2,4-triazol-5-yl)acetate

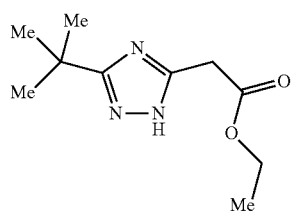 [SMILES: CCOC(=O)Cc1nc(C(C)(C)C)n[nH]1]

Ethyl 3-[(2,2-Dimethylpropanoyl)imino]-3-ethoxypropanoate (Preparation 117, 40 g, 0.165 mol) was dissolved in methanol (250 mL) and hydrazine hydrate (9.6 mL, 0.196 mol) was added at 0° C. The reaction mixture was stirred for 24 hours. The solvents concentrated in vacuo. The residue was dissolved in water (200 mL), and the solution was extracted with chloroform (3×100 mL). The combined organic extracts were dried over MgSO$_4$ and evaporated to afford the title compound (20.7 g, 59%).

¹H NMR (400 MHz, DMSO-d$_6$): δ ppm 1.18 (t, 3H), 1.26 (s, 9H), 3.70 (s, 2H), 4.09 (q, 2H).

Preparation 117

Ethyl 3-[(2,2-Dimethylpropanoyl)imino]-3-ethoxypropanoate

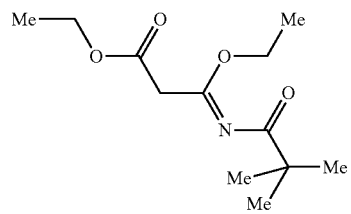 [SMILES: CCOC(=O)C/C(=N/C(=O)C(C)(C)C)OCC]

Ethyl 3-Ethoxy-3-iminopropanoate Hydrochloride (Preparation 118, 50 g, 0.256 mol) was suspended in dichloromethane (600 mL). The suspension was cooled to −15° C. and triethylamine (7.8 mL, 0.56 mol) followed by pivaloyl chloride (31.5 mL, 0.256 mol) were added. The reaction mixture was left for 18 hours at room temperature, then washed with water, dried over MgSO$_4$, and evaporated. The residue was triturated with hexane. The resulting precipitate was filtered and dried to afford the title compound (44 g, 70%). Taken directly on to the next step.

Preparation 118

Ethyl 3-Ethoxy-3-iminopropanoate Hydrochloride

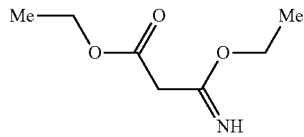 [SMILES: CCOC(=N)CC(=O)OCC]

Dry gaseous HCl was passed through a mixture of ethyl cyanoacetate (18 g, 0.185 mol) and ethanol (9.3 mL) in absolute ether (200 mL) over 1 hour. After standing for 48 hours in a refrigerator, the resulting precipitate was filtered off, washed with anhydrous ether, and dried to afford the title compound that was taken directly on to the next step (29 g, 90%).

Preparation 119

[5-Cyclopropyl-2-(methoxymethyl)-1,3-oxazol-4-yl]acetic Acid

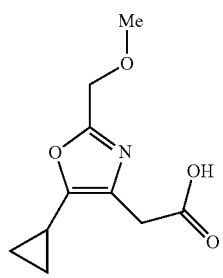 [SMILES: COCc1nc(CC(=O)O)c(C2CC2)o1]

A mixture of ethyl [5-cyclopropyl-2-(methoxymethyl)-1,3-oxazol-4-yl]acetate (Preparation 120, 23.9 g, 0.1 mol) in 10% KOH (100 mL) was stirred at 75° C. for 18 hours. The reaction was cooled and acidified with 10% HCl to pH 3, and extracted with chloroform (3×100 mL). The organic extract was dried over $Na_2SO_4$ and concentrated in vacuo. The residue was dissolved in ether and crystallized in a refrigerator at −20° C. The precipitated crystals were separated by filtration, washed with cold ether, and vacuum-dried to give the title compound as a white crystalline substance in a form of light plates (16.9 g, 93.2%).

$^1$H NMR (400 MHz, DMSO-$d_6$): δ ppm 0.75 (m, 2H), 0.95 (m, 2H), 2.00 (m, 1H), 3.30 (s, 3H), 3.45 (s, 2H), 4.40 (s, 2H), 12.40 (br s, 1H).

Preparation 120

Ethyl [5-cyclopropyl-2-(methoxymethyl)-1,3-oxazol-4-yl]acetate

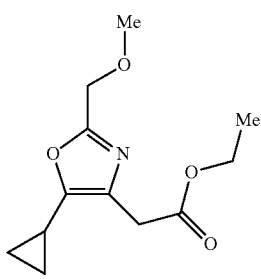 [SMILES: CCOC(=O)Cc1nc(COC)oc1C1CC1]

Ethyl 4-Cyclopropyl-3-[(methoxyacetyl)amino]-4-oxobutanoate (Preparation 121, 25.7 g, 0.1 mol) was dissolved in dry DMF (170 mL). $POCl_3$ (46 g, 0.3 mol) was poured into this solution at 5-15° C., and the mixture was kept this temperature for 60 minutes. The resulting solution was slowly poured in portions into crushed ice (700 g) and stirred until a homogeneous solution was obtained. The solution was neutralized with a 20% aqueous $K_2CO_3$ solution to pH 7-8. The product was extracted with ethyl acetate. The organic extract was washed with brine and concentrated in vacuo to give a dark-brown liquid, which was purified by silica gel column chromatography eluting with EtOAc:Hexane 1:1 to afford the title compound as a colourless liquid (96%). Taken directly on to the next step.

Preparation 121

Ethyl 4-Cyclopropyl-3-[(methoxyacetyl)amino]-4-oxobutanoate

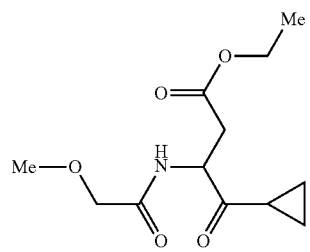 [SMILES: CCOC(=O)CC(NC(=O)COC)C(=O)C1CC1]

DMAP (5 g, 0.041 mol) and cyclopropylcarbonyl anhydride (462.5 g, 3 mol) were added to a suspension of L-N-methoxyethyl aspartic acid monoethyl ester (Preparation 122, 229 g, 1 mol) in pyridine (1.5 L). The obtained mixture was kept at 90° C. for 2 hours, concentrated to dryness at 60° C., and azeotroped with toluene to remove residual pyridine. The residue was purified by silica gel column chromatography eluting with 60% EtOAc in hexane to afford the title compound (85%). Taken directly on to the next step.

Preparation 122

L-N-Methoxyethyl Aspartic Acid Monoethyl Ester

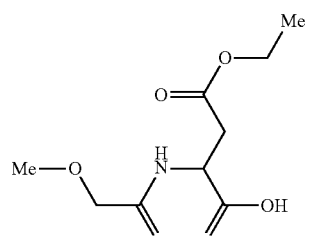

$NaHCO_3$ (252 g, 3 mol) was added to a solution of DL-aspartic acid monoethyl ester hydrochloride (197.6 g, 1 mol) in water (1.7 L), and a solution of 1-[(methoxyacetyl)oxy]pyrrolidine-2,5-dione (Preparation 123, 187 g, 1 mol) in dioxane (1.7 L) was added dropwise at 0° C. The reaction mixture was stirred at room temperature for 20 hours, acidified with 4N HCl to pH 3, and subjected to extraction with chloroform (5×500 mL). The extract was washed with brine, dried over $Na_2SO_4$, and concentrated in vacuo. The residue was recrystallized from ethyl acetate to give the title compound as a white crystalline solid (195.5 g, 85%). Taken directly on to the next step.

Preparation 123

1-[(Methoxyacetyl)oxy]pyrrolidine-2,5-dione

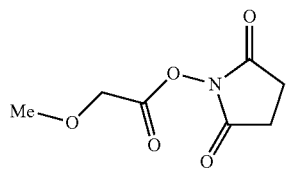 [SMILES: COCC(=O)ON1C(=O)CCC1=O]

A solution of methoxyacetyl chloride (108.5 g, 1 mol) in absolute dichloromethane (170 mL) was added dropwise at 0° C. to a solution of N-hydroxysuccinimide (115 g, 1 mol) and TEA (111 g, 1 mol) in dichloromethane (900 mL). The reaction mixture was stirred at room temperature for 48 hours, and a saturated NaHCO$_3$ solution (500 mL) was added under stirring. The organic layer was separated, and the aqueous layer was subjected to extraction twice with chloroform. The combined organic extract was washed with saturated NaHCO$_3$ solution (200 mL), brine (200 mL), and dried over Na$_2$SO$_4$. The solution was concentrated in vacuo to afford the title compound as a yellow oil (147.8 g, 79%). Taken directly on to the next step.

Preparation 124

(5-isopropyl-1H-pyrazol-1-yl)acetic acid

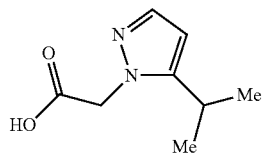 [SMILES: CC(C)c1ccnn1CC(=O)O]

Prepared according to the method described for Preparation 74 using (5-isopropyl-1H-pyrazol-1-yl)acetic acid ethyl ester (Preparation 125) in IMS.
MS m/z 169 [M+H]$^+$ Preparation 125

(5-isopropyl-1H-pyrazol-1-yl)acetic acid ethyl ester

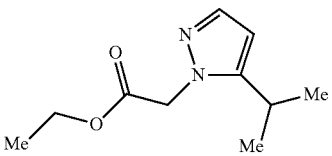 [SMILES: CCOC(=O)Cn1nccc1C(C)C]

Prepared according to the method described for Preparation 75 using 5-isopropyl-1H-pyrazole and ethyl bromoacetate. The residue was purified using silica gel column chromatography eluting with 4:1 hexane:EtOAc. The title compound was isolated as the lower running minor product in 6% yield, and taken directly on to the next step.

Preparation 126

(4-cyclopropyl-1H-pyrazol-1-yl)acetic acid

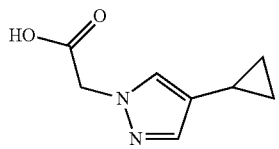 [SMILES: O=C(O)Cn1cc(C2CC2)cn1]

Prepared according to the analogous method described for Preparation 75 using 4-cyclopropyl-1H-pyrazole (Liebigs Annalen der Chemie (1984) (4) 649) followed by the method described for Preparation 76.

Preparation 127

(1E)-1-(dimethylamino)-2,4-dimethylpent-1-en-3-one

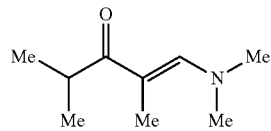

2-Methyl-3-pentanone (5 g, 49.9 mmol) and DMF-DMA (10 mL, 74.9 mmol) were heated together in a sealed tube for 4 days. The reaction was concentrated in vacuo to afford an orange oil that was used directly in the next reaction (1.64 g, 21%).

Preparation 128

3-isopropyl-5-methyl-1H-pyrazole

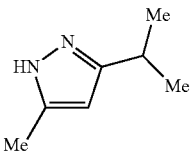

(1E)-1-(dimethylamino)-2,4-dimethylpent-1-en-3-one (Preparation 127, 1.64 g, 10.56 mmol) was heated with hydrazine hydrate (5 mL) at 100° C. for 3 hours. The reaction was allowed to cool and partitioned between EtOAc and water. The organic layer was collected, washed with brine, dried over MgSO₄ and concentrated in vacuo to afford an orange oil that was used directly in the next reaction (1.07 g, 82%).

Preparation 129

Ethyl (3-isopropyl-5-methyl-1H-pyrazol-1-yl)acetate and ethyl (5-isopropyl-3-methyl-1H-pyrazol-1-yl) acetate

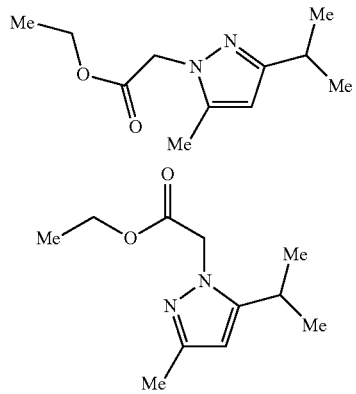

A suspension of 3-isopropyl-5-methyl-1H-pyrazole (Preparation 128, 1.07 g, 8.6 mmol), ethylbromoacetate (1 mL, 9.03 mmol) and potassium carbonate (3.57 g, 25.58 mmol) in DMF (10 mL) was stirred at room temperature for 18 hours. The reaction was diluted with EtOAc and washed with 1N HCl. The organic layer was collected, washed with brine, dried over MgSO₄ and concentrated in vacuo. The residue was purified using silica gel column chromatography eluting with 4:1 Hexane:EtOAc to obtain two regioisomers:

Major higher running peak: ethyl (3-isopropyl-5-methyl-1H-pyrazol-1-yl)acetate (607 mg, 34%).

Minor lower running peak: ethyl (5-isopropyl-3-methyl-1H-pyrazol-1-yl)acetate (102 mg, 6%).

Preparation 130

(3-isopropyl-5-methyl-1H-pyrazol-1-yl)acetic acid

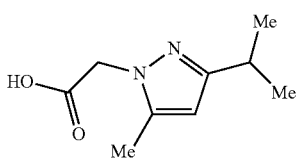 [SMILES: Cc1cc(C(C)C)nn1CC(=O)O]

A mixture of ethyl (3-isopropyl-5-methyl-1H-pyrazol-1-yl)acetate (Preparation 129, 571 mg, 2.72 mmol) and LiOH (342 mg, 8.15 mmol) in IMS (5 mL) and water (4 mL) was stirred at room temperature for 30 minutes. The reaction was acidified with 2M HCl and extracted with EtOAc. The organic layer was collected, washed with brine, dried over MgSO₄ and concentrated in vacuo to afford the title compound as a cream solid (328 mg, 66%).

Preparation 131

(3-isopropyl-1H-pyrazol-1-yl)acetic acid

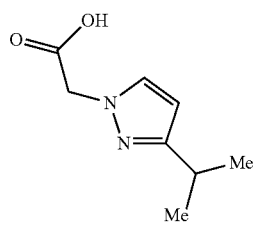 [SMILES: CC(C)c1ccn(CC(=O)O)n1]

Prepared according to the analogous method described for Preparation 75, using 3-isopropyl-1H-pyrazole and ethyl bromoacetate isolating the higher running peak as the desired isomer, followed by the hydrolysis method of Preparation 74.

Preparation 132

[4-(methoxymethyl)-1H-1,2,3-triazol-1-yl]acetic acid

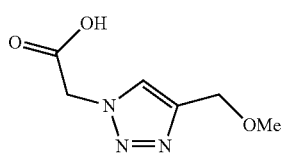 [SMILES: COCc1cn(CC(=O)O)nn1]

Prepared according to the methods described for Preparation 90 using methyl propargylether.

BIOLOGICAL ACTIVITY

Isolated TRK Enzyme assays use the HTRF KinEASE-TK kit (Cisbio Cat#62TK0PEJ) with recombinant His-tagged cytoplasmic domains of each TRK receptor sourced from Invitrogen (see table below). This activity-assay measures the phosphorylation of tyrosine residues within a substrate from the HTRF kit which has been validated by Cisbio for a variety of tyrosine kinases including the TRK receptors.

Assay Details:

| Target | Invitrogen Cat# | Amino acids | FAC enzyme | FAC ATP | Assay Reaction Time |
|---|---|---|---|---|---|
| TRKA | PV3144 (NTRK1) | aa 441-796 | 4 nM | 40 uM | 35 min |
| TRKB | PV3616 (NTRK2) | aa 526-838 | 1 nM | 1.4 uM | 40 min |
| TRKC | PV3617 (NTRK3) | aa 510-825 | 10 nM | 15 uM | 30 min |

0.5 mM stock solutions of test compounds are prepared and serially diluted in 100% DMSO. A standard curve using the compound of Example 135 disclosed in WO2005/116035 of 150 uM is also prepared on each test plate. High percentage effect (HPE) is defined by 150 uM (using the compound of Example 135 as disclosed in WO2005/116035) and 0% effect (ZPE) is defined by 100% DMSO. Greiner low volume black plates containing 0.2 ul of serially diluted compound, standard and HPE/ZPE are created using the Bravo nanoliter dispenser.

1× enzyme buffer is prepared from 5× Enzymatic Buffer from the Cisbio KinEASE TK kit using MilliQ water. The buffer is then supplemented with 10 mM MgCI and 2 mM DTT (both from Sigma). In the case of TRKB, the buffer is also supplemented with 125 nM Supplement Enzymatic Buffer (SEB) from the Cisbio kit.

2× FAC of enzyme and 2× FAC ATP diluted in 1× complete enzyme buffer is incubated at room temperature for 20 minutes to preactivate the enzyme. Following this preactivation step, 5 ul/well of enzyme+ATP mix is added using a Multidrop Micro to the assay plate, spotted with 0.2 ul 100% DMSO compound. This is left for 20 mins at room temperature before adding 5 ul of 2 uM TK-substrate-Biotin (from the Cisbio kit) diluted in 1× enzyme buffer (1 uM FAC) using the Multidrop Micro. The reaction is incubated at room temperature for the optimized assay reaction time (see table). The reaction is stopped by adding 10 ul/well HTRF Detection Buffer containing 0.25 uM Streptavidin-XL665 (0.125 uM FAC) and 1:200 TK Antibody-Cryptate using a Multidrop.

After the Detection Reagent addition, plates are covered and incubated at room temperature for 60 minutes. HTRF signal is read using an Envision reader, measured as a ratio of emissions at two different wavelengths, 620 nm and 665 nm. Any compound that inhibits the action of the TRK kinase will have a lower fluorescence ratio value 665/620 nM than compounds which do not inhibit the TRK kinase. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Cell Based Assays were carried out using Cell lines from DiscoveRx utilising their PathHunter technology and reagents in an antagonist assay:

| Target | DiscoveRx cell line Cat# | Cognate Neurotrophin |
|---|---|---|
| TRKA | 93-0462C3 | NGF |
| TRKA co expressed with p75 | 93-0529C3 | NGF |
| TRKB | 93-0463C3 | BDNF |
| TRKB co expressed with p75 | 93-0530C3 | BDNF |
| TRKC | 93-0464C3 | NT3 |
| TRKC co expressed with p75 | 93-0531C3 | NT3 |

The assays are based upon DiscoveRx's proprietary Enzyme Fragment Complementation (EFC) technology. In the case of the TRK cell lines, the enzyme acceptor (EA) protein is fused to a SH2 protein and the TRK receptor of interest has been tagged with a Prolink tag.

Upon neurotrophin binding, the TRK receptor becomes phosphorylated, and the tagged SH2 protein binds. This results in functional complementation and restored β-Galactosidase activity which is can be measured using the luminescent Galacton Star substrate within the PathHunter reagent kits.

Generally, small molecule inhibitors bind to the kinase domain so are not competing with the neurotrophin (agonist) which binds to an extracellular site. This means that the $IC_{50}$ is a good measure of affinity and should be unaffected by concentration neurotrophin stimulant.

Cryopreserved PathHunter cells are used from either in-house produced batches or bulk batches bought directly from DiscoveRx. Cryopreserved cells are resuscitated, spun 1000 rpm for 4 min to remove freezing media, and resuspended in MEM+0.5% horse serum (both Invitrogen) to $5e^5$ cells/ml. The cells are then plated using a Multidrop into Greiner white tissue culture treated plates at 20 ul/well and incubated for 24 h at 37° C., 5% $CO_2$, high humidity. On the day of the assay, the cell plates are allowed to cool to room temperature for 30 min prior to the assay.

4 mM stock solutions of test compounds are prepared and serially diluted in 100% DMSO. A standard curve using the compound of Example 135, WO2005/116035 at a top concentration of 150 uM is also prepared on each test plate. High percentage effect (HPE) is defined by 150 uM of the compound of Example 135, WO2005/116035 and 0% effect (ZPE) is defined by 100% DMSO. Plates containing 1 ul of serially diluted compound, standard and HPE/ZPE are diluted 1/66 in assay buffer (PBS minus $Ca^{2+}$, minus $Mg^{2+}$ with 0.05% pluronic F127) using a Wellmate. Using a Platemate Plus, 5 ul of 1/66 diluted test compounds is then transferred to the cell plate and allowed to reach equilibrium by incubating for 30 min at room temperature before addition of agonist stimulus: 10 ul/well of 2 nM (0.571 nM FAC) of the cognate neurotrophin (Peprotech) diluted in agonist buffer (HBSS with 0.25% BSA). Final assay concentration of the test compounds is 8.66 µM, (the compound of Example 135, WO2005/116035 FAC is 0.325 uM). The plates are left at room temperature for a further 2 hours before addition of 10 ul of the DiscoveRx PathHunter detection reagent (made up by adding 1 part Galacton Star, 5 parts Emerald II and 19 parts Cell Assay Buffer as per the manufacturer's instructions).

After reagent addition, plates are covered and incubated at room temperature for 60 minutes. Luminescence signal is read using an Envision. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Brain Penetration Assays

In Vitro

MDCK-BCRP: MDCK-BCRP data may be collected according to the method described in "A 96-Well Efflux Assay To Identify ABCG2 Substrates Using a Stably Transfected MDCK II Cell Line" http://pubs.acs.org/doi/full/10.1021/mp050088t Yongling Xiao, Ralph Davidson, Arthur Smith, Dennis Pereira, Sabrina Zhao, John Soglia, David Gebhard, Sonia de Morais, and David B. Duignan, Mol. Pharm., 2006, 3 (1), pp 45-54.

MDCK-MDR1: MDCK-MDR1 data may be collected according to the method described in "Are MDCK Cells Transfected with the Human MDR1 Gene a Good Model of the Human Intestinal Mucosa?" http://www.springerlink-.com/content/qfhqlqbr4fnp3khf/fulltext.pdf Fuxing Tang, Kazutoshi Horie, and Ronald T. Borchardt, Pharmaceutical Research, Vol. 19, No. 6, June 2002.

In Vivo

Brain penetration may be measured according to the method described in "Assessing brain free fraction in early drug discovery". Read, K; Braggio, S., Expert Opinion Drug Metab Toxicol. (2010) 6 (3) 337-344.

Below are TrkA $IC_{50}$ data generated using the PV3144 TrkA enzyme assay. Where more than one reading was taken, the arithmetic mean is presented.

| Example | Trka enzyme (IC$_{50}$) | Example | Trka enzyme (IC$_{50}$) | Example | Trka enzyme (IC$_{50}$) |
|---|---|---|---|---|---|
| 1 | 6.32 nM | 45 | 1570 nM | 89 | 82.4 nM |
| 2 | 5.58 nM | 46 | 3080 nM | 90 | 19.6 nM |
| 3 | 7.85 nM | 47 | 187 nM | 91 | 15 nM |
| 4 | 5.33 nM | 48 | 33.8 nM | 92 | 39.8 nM |
| 5 | 4.41 nM | 49 | 180 nM | 93 | 38.7 nM |
| 6 | 6.53 nM | 50 | 133 nM | 94 | 20 nM |
| 7 | 6.61 nM | 51 | 68.2 nM | 95 | 2.92 nM |
| 8 | 38.5 nM | 52 | 137 nM | 96 | 13.8 nM |
| 9 | 97.8 nM | 53 | 110 nM | 97 | 31.1 nM |
| 10 | 14 nM | 54 | 176 nM | 98 | 40.6 nM |
| 11 | 79.3 nM | 55 | 73.8 nM | 99 | 42.9 nM |
| 12 | 9.54 nM | 56 | 177 nM | 100 | 2370 nM |
| 13 | 9.86 nM | 57 | 1680 nM | 101 | 51.7 nM |
| 14 | 9.89 nM | 58 | 6520 nM | 102 | 7450 nM |
| 15 | 12.4 nM | 59 | 63.9 nM | 103 | 15.2 nM |
| 16 | 18.2 nM | 60 | 44.7 nM | 104 | 13.8 nM |
| 17 | 106 nM | 61 | 65.9 nM | 105 | 108 nM |
| 18 | 36.4 nM | 62 | 54.3 nM | 106 | 17.9 nM |
| 19 | 26.4 nM | 63 | 28.8 nM | 107 | 64 nM |
| 20 | 31.7 nM | 64 | 105 nM | 108 | 640 nM |
| 21 | 27.1 nM | 65 | 37 nM | 109 | 87.1 nM |
| 22 | 9.64 nM | 66 | 37.6 nM | 110 | 3330 nM |
| 23 | 192 nM | 67 | 101 nM | 111 | 96.8 nM |
| 24 | 124 nM | 68 | 201 nM | 112 | 5110 nM |
| 25 | 21.4 nM | 69 | 77.6 nM | 113 | 20.4 nM |
| 26 | 108 nM | 70 | 65.6 nM | 114 | 289 nM |
| 27 | 89.7 nM | 71 | 149 nM | 115 | 42 nM |
| 28 | 10.6 nM | 72 | 125 nM | 116 | 11.3 nM |
| 29 | 106 nM | 73 | 88.3 nM | 117 | 39.2 nM |
| 30 | 13.3 nM | 74 | 233 nM | 118 | 9150 nM |
| 31 | 9.66 nM | 75 | 44.9 nM | 119 | 4900 nM |
| 32 | 11.4 nM | 76 | 121 nM | 120 | 39.5 nM |
| 33 | 3.11 nM | 77 | 33.7 nM | 121 | 14.3 nM |
| 34 | 17.1 nM | 78 | 15.8 nM | 122 | 1220 nM |
| 35 | 87.9 nM | 79 | 26.1 nM | 123 | 59.5 nM |
| 36 | 44.7 nM | 80 | 357 nM | 124 | 198 nM |
| 37 | 51.7 nM | 81 | 67 nM | 125 | 707 nM |
| 38 | 147 nM | 82 | 6.16 nM | 126 | 28.6 nM |
| 39 | 181 nM | 83 | 344 nM | 127 | 41.8 nM |
| 40 | 1730 nM | 84 | 141 nM | 128 | 147 nM |
| 41 | 3330 nM | 85 | 23.3 nM | 129 | 96.2 nM |
| 42 | 179 nM | 86 | 93.2 nM | 130 | 161 nM |
| 43 | 118 nM | 87 | 29 nM | 131 | 92.8 nM |
| 44 | 531 nM | 88 | 68.4 nM | 132 | 505 nM |
| 133 | 4340 nM | 178 | 22 nM | 223 | 27.8 nM |
| 134 | 284 nM | 179 | 163 nM | 224 | 15.4 nM |
| 135 | 2600 nM | 180 | 1080 nM | 225 | 46.3 nM |
| 136 | 268 nM | 181 | 536 nM | 226 | 11.3 nM |
| 137 | 9800 nM | 182 | 26.1 nM | 227 | 24.3 nM |
| 138 | 45.3 nM | 183 | 17.7 nM | 228 | 18.5 nM |
| 139 | 100 nM | 184 | 3180 nM | 229 | 200 nM |
| 140 | 207 nM | 185 | 1860 nM | 230 | 18.1 nM |
| 141 | 20.2 nM | 186 | 13.3 nM | 231 | 12.8 nM |
| 142 | 29.9 nM | 187 | 9800 nM | 232 | 11.3 nM |
| 143 | 986 nM | 188 | 477 nM | 233 | 24.4 nM |
| 144 | 22.2 nM | 189 | 13.6 nM | 234 | 16.5 nM |
| 145 | 305 nM | 190 | 775 nM | 235 | 2.87 nM |
| 146 | 59.4 nM | 191 | 7.41 nM | 236 | 43.1 nM |
| 147 | 4310 nM | 192 | 9800 nM | 237 | Not tested |
| 148 | 424 nM | 193 | 10100 nM | 238 | Not tested |
| 149 | 200 nM | 194 | 13.8 nM | 239 | Not tested |
| 150 | 3080 nM | 195 | 203 nM | 240 | 24 nM |
| 151 | 408 nM | 196 | 1280 nM | | |
| 152 | 2150 nM | 197 | 525 nM | | |
| 153 | 83.9 nM | 198 | 105 nM | | |
| 154 | 1100 nM | 199 | 186 nM | | |
| 155 | 2390 nM | 200 | 174 nM | | |
| 156 | 342 nM | 201 | 314 nM | | |
| 157 | 420 nM | 202 | 437 nM | | |
| 158 | 9800 nM | 203 | 71.3 nM | | |
| 159 | 271 nM | 204 | 227 nM | | |
| 160 | 8990 nM | 205 | 33 nM | | |
| 161 | 103 nM | 206 | 20.7 nM | | |
| 162 | 56 nM | 207 | 179 nM | | |
| 163 | 10.7 nM | 208 | 29.7 nM | | |
| 164 | 33 nM | 209 | 264 nM | | |
| 165 | 5.68 nM | 210 | 45.6 nM | | |
| 166 | 955 nM | 211 | 93.3 nM | | |
| 167 | 181 nM | 212 | 479 nM | | |
| 168 | 14.7 nM | 213 | 252 nM | | |
| 169 | 83.6 nM | 214 | 93.1 nM | | |
| 170 | 6510 nM | 215 | 62 nM | | |
| 171 | 36.1 nM | 216 | 20.4 nM | | |
| 172 | 8.49 nM | 217 | 418 nM | | |
| 173 | 3.85 nM | 218 | 425 nM | | |
| 174 | 51.4 nM | 219 | 15.2 nM | | |
| 175 | 5.3 nM | 220 | 160 nM | | |
| 176 | 904 nM | 221 | 138 nM | | |
| 177 | 102 nM | 222 | 16.4 nM | | |

All publications cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention.

Accordingly, the invention is limited only by the following claims.

The invention claimed is:

1. A compound of Formula I:

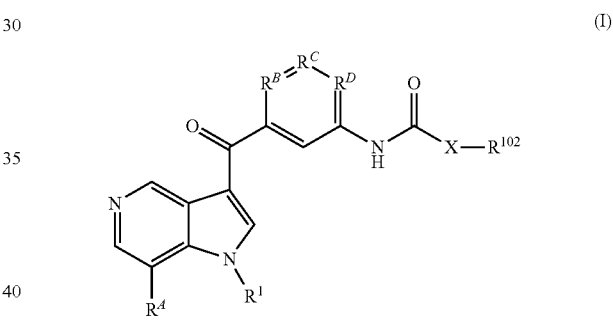

or a pharmaceutically acceptable salt thereof, wherein $R^A$ is H or F;

One of $R^B$, $R^C$ and $R^D$ is N and the others are CH, CCN or C($C_{1-4}$ alkoxy);

X is a bond or $CH_2$;

$R^1$ is selected from $C_{2-4}$ alkyl optionally substituted by OH, or oxetanyl; and $R^{102}$ is 5- or 6-membered unsaturated ring optionally substituted by 1 or 2 substituents independently selected from halo, =O, CN, $C_{1-4}$ alkyl optionally substituted by one or more F, OH or $C_{1-3}$ alkoxy optionally substituted by one or more F, and $C_{3-6}$ cycloalkyl.

2. The compound according to claim 1 or a pharmaceutically acceptable salt thereof wherein $R^1$ is selected from:

3. The compound according to claim 1 or a pharmaceutically acceptable salt thereof wherein $R^{102}$ is a ring system which ring is selected from:

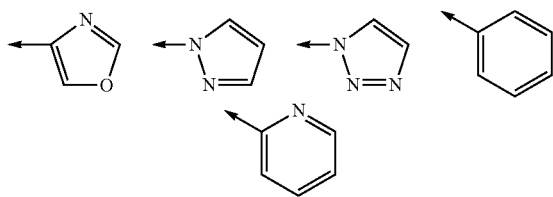

and which ring is optionally substituted by 1 or 2 substituents independently selected from F, Cl, =O, CN, $CF_3$, $OCF_3$, $CH_3$, isopropyl, $OCH_3$, cyclopropyl, and

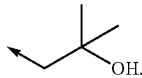

4. The compound according to claim 1 or a pharmaceutically acceptable salt thereof wherein $R^B$ and $R^D$ are CH and $R^C$ is N.

5. The compound according to claim 1, or a pharmaceutically acceptable salt thereof wherein X is $CH_2$.

6. The compound according to claim 1, or a pharmaceutically acceptable salt thereof wherein $R^1$ is 1-hydroxy-2-methylpropan-2-yl.

7. A compound of Formula:

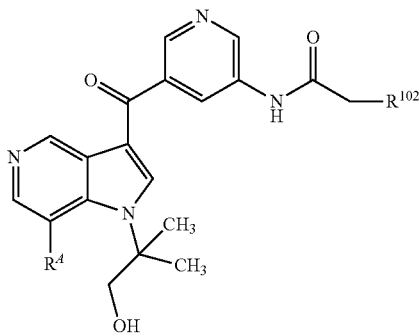

or a pharmaceutically acceptable salt thereof, wherein
  $R^A$ is H or F;
  and $R^{102}$ is selected from phenyl, pyridyl and pyrazolyl, each of which is substituted by 1 or 2 substituents independently selected from cyclopropyl, methyl, $CF_3$ and Cl.

8. The compound according to claim 7 or a pharmaceutically acceptable salt thereof wherein $R^{102}$ is selected from phenyl, pyridin-2-yl and pyrazol-1-yl, each of which is substituted by 1 or 2 substituents independently selected from cyclopropyl, methyl, $CF_3$ and Cl.

9. The compound according to claim 8 or a pharmaceutically acceptable salt thereof wherein $R^{102}$ is selected from 4-chlorophenyl, 3-$CF_3$-phenyl, 4-$CF_3$-phenyl, 5-chloropyridin-2-yl, 4-$CF_3$-pyrazol-1-yl, 3-cyclopropylpyrazol-1-yl and 5-methyl-3-$CF_3$-pyrazol-1-yl.

10. A compound selected from:
  N-{5-[7-Fluoro-1-(2-hydroxy-1,1-dimethyl-ethyl)-1H-pyrrolo[3,2-c]pyridine-3-carbonyl]-pyridin-3-yl}-2-(5-methyl-3-trifluoromethyl-pyrazol-1-yl)-acetamide;
  2-(3-Cyclopropyl-pyrazol-1-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
  2-(5-Chloro-pyridin-2-yl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
  N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-pyrazol-1-yl)-acetamide;
  N-{5-[7-Fluoro-1-(2-hydroxy-1,1-dimethyl-ethyl)-1H-pyrrolo[3,2-c]pyridine-3-carbonyl]-pyridin-3-yl}-2-(3-trifluoromethyl-phenyl)-acetamide;
  2-(4-Chloro-phenyl)-N-{5-[7-fluoro-1-(2-hydroxy-1,1-dimethyl-ethyl)-1H-pyrrolo[3,2-c]pyridine-3-carbonyl]-pyridin-3-yl}-acetamide;
  N-{5-[7-Fluoro-1-(2-hydroxy-1,1-dimethyl-ethyl)-1H-pyrrolo[3,2-c]pyridine-3-carbonyl]-pyridin-3-yl}-2-(4-trifluoromethyl-phenyl)-acetamide; and
  2-(5-Chloro-pyridin-2-yl)-N-{5-[1-(2-hydroxy-1,1-dimethyl-ethyl)-1H-pyrrolo[3,2-c]pyridine-3-carbonyl]-pyridin-3-yl}-acetamide or a pharmaceutically acceptable salt thereof.

* * * * *